(12) United States Patent
Kasina et al.

(10) Patent No.: US 8,815,879 B2
(45) Date of Patent: *Aug. 26, 2014

(54) SUBSTITUTED 4-(SELENOPHEN-2(OR-3)-YLAMINO)PYRIMIDINE COMPOUNDS AND METHODS OF USE THEREOF

(71) Applicant: Kasina Laila Innova Pharmaceuticals Private Limited, Vijayawada (IN)

(72) Inventors: Sudhakar Kasina, Mercer Island, WA (US); Ganga Raju Gokaraju, Vijayawada (IN); Venkateswarlu Somepalli, Vijayawada (IN); Rama Raju Gokaraju, Vijayawada (IN); Venkata Kanaka Ranga Raju Gokaraju, Vijayawada (IN); Kiran Bhupathiraju, Vijayawada (IN); Trimurtulu Golakoti, Vijayawada (IN); Krishanu Sengupta, Vijayawada (IN); Venkata Krishna Raju Alluri, Vijayawada (IN)

(73) Assignee: Kasina Laila Innova Pharmaceuticals Private Limited, Vijayawada, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/896,538

(22) Filed: May 17, 2013

(65) Prior Publication Data

US 2013/0266563 A1    Oct. 10, 2013

Related U.S. Application Data

(63) Continuation of application No. PCT/IN2011/000801, filed on Nov. 17, 2011.

(30) Foreign Application Priority Data

Nov. 18, 2010    (IN) ............................ 3468/CHE/2010

(51) Int. Cl.
*A61K 31/517*    (2006.01)
*C07D 239/72*    (2006.01)

(52) U.S. Cl.
USPC ................... 514/266.24; 514/234.5; 544/293; 544/119

(58) Field of Classification Search
USPC ................... 514/266.24, 234.5; 544/293, 119
See application file for complete search history.

(56) References Cited

U.S. PATENT DOCUMENTS

| | | | |
|---|---|---|---|
| 6,620,804 B2 | 9/2003 | Chang et al. | |
| 6,919,338 B2 | 7/2005 | Mortlock et al. | |
| 7,417,055 B2 | 8/2008 | Cannizzaro et al. | |
| 2008/0021031 A1 | 1/2008 | Shia et al. | |
| 2009/0163494 A1 | 6/2009 | Hong et al. | |
| 2010/0004208 A1 | 1/2010 | Chaplin et al. | |
| 2010/0272678 A1 | 10/2010 | Gokaraju et al. | |
| 2013/0287767 A1* | 10/2013 | Gokaraju et al. | .......... 424/133.1 |

OTHER PUBLICATIONS

International Search Report issued for PCT/IN2011/000801 dated May 23, 2012.
Aumann, et al., "On the stability of 2-aminoselenophene-3-carboxylates: potential dual-acting selenium-containing allosteric enhancers of A1 adenosine receptor binding", Org. Biomol. Chem., 2007,5, 1276-1281, Mar. 15, 2007.
International Search Report issued for PCT/IN2011/000832 dated Jul. 7, 2012.

* cited by examiner

*Primary Examiner* — Rei-tsang Shiao
(74) *Attorney, Agent, or Firm* — Kramer Amado, P.C.

(57) ABSTRACT

Selenophene compounds of formula (I) are described herein. In the compounds of Formula (I), ring A is a 6-membered aromatic fused ring, optionally containing one, two or three nitrogen atoms; a 5-membered heteroaromatic fused ring; or a mono- or bicyclic saturated heterocyclic fused ring having at least one ring member selected from the group consisting of N, O, S, SO and $SO_2$; Y in ring B is nitrogen or substituted carbon; X is $NR^6$, O, S, S(O), or $S(O)_2$. $R^1, R^2, R^3, R^4$, and $R^6$ are defined in the specification. Selenophene compounds of formula (I) may be used in methods of treating cell proliferative disorders, particularly cancer. Pharmaceutical compositions containing selenophene compounds of formula (I) may be used for treatment, inhibition, or control of cancer.

Formula I

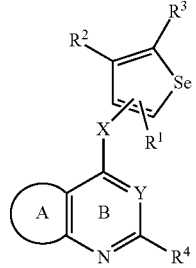

39 Claims, 1 Drawing Sheet

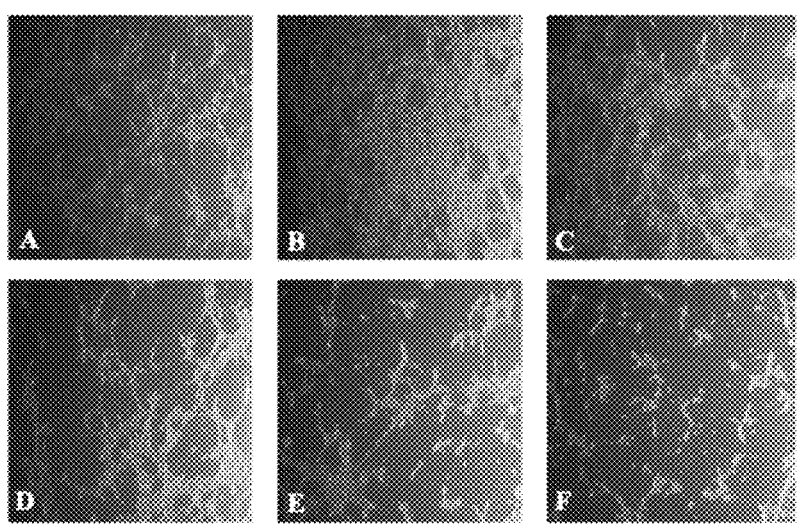

SUBSTITUTED 4-(SELENOPHEN-2(OR-3)-YLAMINO)PYRIMIDINE COMPOUNDS AND METHODS OF USE THEREOF

RELATED APPLICATIONS

This application is a continuation-in-part of parent International Application No. PCT/IN2011/000801, filed on Nov. 17, 2011, now published as WO 2012/066578. International Application No. PCT/IN2011/000801 claims priority to Indian Patent Application No. 3468/CHE/2010, filed on Nov. 18, 2010. The entire disclosure of each prior application is hereby incorporated by reference in its entirety.

FIELD OF THE DISCLOSURE

The disclosure relates to substituted selenophene compounds; processes for their preparation; methods of treating cancer; and methods of making pharmaceutical compositions for the treatment or inhibition or control of cancer.

BACKGROUND

Cancer is a disease resulting from an abnormal growth of tissue. Certain cancers have the potential to invade into local tissues and also metastasize to distant organs. This disease can develop in a wide variety of different organs, tissues and cell types. Therefore, the term "cancer" refers to a collection of over a thousand different diseases. Over 4.4 million people worldwide were diagnosed with breast, colon, ovarian, lung, or prostate cancer and over 2.5 million people died of these devastating diseases. In the United States alone, over 1.25 million new cases and over 500,000 deaths from cancer were in 2005. The majority of these new cases will be cancers of the colon (~100,000), lung (~170,000), breast (~210,000) and prostate (~230,000). Both the incidence and prevalence of cancer is predicted to increase by approximately 15% over the next ten years, reflecting an average growth rate of 1.4% (American Cancer Society, Cancer Facts and Figures 2005; http://www.cancer.org).

Cancer treatments are of two major types, either curative or palliative. The main curative therapies for cancer are surgery and radiation. These options are generally successful only if the cancer is found at an early localized stage. Once the disease has progressed to locally advanced cancer or metastatic cancer, these therapies are less effective and the goal of therapy aims at symptom palliation and maintaining good quality of life. The most prevalent treatment protocols in either treatment mode involve a combination of surgery, radiation therapy and/or chemotherapy.

Cytotoxic drugs (also known as cytoreductive agents) are used in the treatment of cancer, either as a curative treatment or with the aim of prolonging life or palliating symptoms. Cytotoxics may be combined with radiotherapy and/or surgery, as neo-adjuvant treatment (initial chemotherapy aimed at shrinking the tumor, thereby rendering local therapy such as surgery and radiation more effective) or as adjuvant chemotherapy (used in conjunction or after surgery and/or localized therapy). Combinations of different drugs are frequently more effective than single drugs: they may provide an advantage in certain tumors of enhanced response, reduced development of drug resistance and/or increased survival. It is for these reasons that the use of combined cytotoxic regimens in the treatment of many cancers is very common. Cytotoxic agents in current use employ different mechanisms to block proliferation and induce cell death. They can be generally categorized into the following groups based on their mechanism of action: the microtubule modulators that interfere with the polymerization or depolymerization of microtubules (e.g. docetaxel, paclitaxel, vinblastine, vinorelbine); anti-metabolites including nucleoside analogs and other inhibitors of key cellular metabolic pathways (e.g. capecitabine, gemcitabine, methotrexate); agents that interact directly with DNA (e.g. carboplatin, cyclophosphamide); anthracycline DNA intercalators that interfere with DNA polymerase and Topoisomerase II (e.g. doxorubicin, epirubicin); and the non-anthracycline inhibitors of Topoisomerase activity (e.g. topotecan, irinotecan, and etoposide). Even though different cytotoxic drugs act via different mechanisms of action, each generally leads to at least transient shrinkage of tumors. Cytotoxic agents continue to represent an important component in an oncologist's arsenal of weapons for use in fighting cancer. The majority of drugs currently undergoing late Phase II and Phase III clinical trials are focusing on known mechanisms of action (tubulin binding agents, anti-metabolites, DNA processing), and on incremental improvements in known drug classes (for example the taxanes or the camptothecins). A small number of cytotoxic drugs based on novel mechanisms have recently emerged. Modes of action for these cytotoxics include inhibition of enzymes involved in DNA modification (e.g. histone deacetylase (HDAC)), inhibition of proteins involved in microtubule movement and cell cycle progression (e.g. kinesins, aurora kinase), and novel inducers of the apoptotic pathway (e.g. bcl-2 inhibitors).

Even though cytotoxic agents remain in the forefront of approaches to treat patients with advanced solid tumors, their limited efficacy and narrow therapeutic indices result in significant side effects. Moreover, basic research into cancer has led to the investigation of less toxic therapies based on the specific mechanisms central to tumor progression. Such studies could lead to effective therapy with improvement of the quality of life for cancer patients. Thus, a new class of therapeutic agents has emerged, referred to as cytostatics. Cytostatics direct their action on tumor stabilization and are generally associated with a more limited and less aggravating side effect profile. Their development has resulted from the identification of specific genetic changes involved in cancer progression and an understanding of the proteins activated in cancer such as tyrosine kinases and serine/threonine kinases.

EGFR overexpression occurs frequently in human epithelial malignancies and its activation plays a significant role in the development and progression of human cancers, since EGFR signaling pathways are associated with cell proliferation, survival promotion and apoptosis inhibition. Therefore, EGFR is a very attractive molecular target for cancer therapy. Over the past 20 years, numerous small molecular inhibitors and monoclonal antibodies targeting EGFR have been successfully developed. The 4-anilino quinazolines derivatives, Iressa (Gefitinib) and Tarceva (Erlotinib), are two selective EGFR inhibitors approved by the FDA in 2003 and 2004 for locally advanced or metastatic non-small-cell lung cancer (NSCLC) therapy. The structures of Iressa and Tarceva are depicted below. Clinical data show that 10-20% of all NSCLC patients partially respond to these two EGFR inhibitors, but only Erlotinib prolongs the survival of patients with recurrent NSCLC. Moreover, most of the patients who responded to initial treatment eventually developed resistance to the EGFR inhibitors. Thus there is an urgent unmet medical need to design and develop new, broad therapeutic index and more potent anti-tumor active compounds.

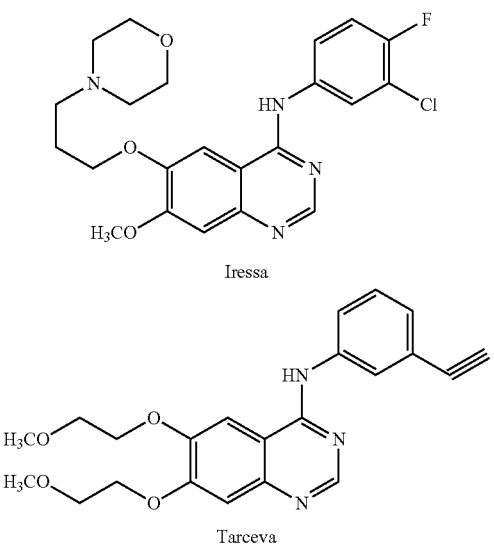

Iressa

Tarceva

The technical problem to be solved according to the present disclosure may therefore be seen in providing novel compounds having good anti-cancer activity or an inhibitory activity on EGFR tyrosine kinases or other kinases, thus offering new therapeutic options for the treatment of diseases, in particular cancer and other proliferative disorders.

SUMMARY

The present disclosure provides substituted 4-(selenophen-2(or 3)-ylamino)pyrimidine compounds of formula (I) and pharmaceutically acceptable salts thereof:

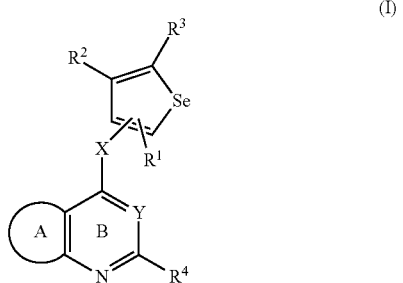

wherein:
ring A is a 6-membered aromatic fused ring, optionally containing one, two or three nitrogen atoms; a 5-membered heteroaromatic fused ring containing at least one heteroatom selected from the group consisting of sulfur, oxygen, nitrogen and selenium, with the proviso that no more than one oxygen or sulfur or selenium atom is present; or a mono- or bicyclic saturated heterocyclic fused ring having 3 to 10 carbon atoms and at least one ring member selected from the group consisting of N, O, S, SO and $SO_2$;
wherein ring A is optionally substituted by at least one group independently selected from the group consisting of hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondary-alkyl, $C_{1-6}$tertiary-alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino $C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl, and a aryl, heteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino $C_{1-6}$alkyl, di($C_{1-6}$alkyl)amino$C_{1-6}$alkyl, $C_{1-6}$alkylsulfinyl, and $C_{1-6}$alkylsulfonyl;
Y in ring B is N or C—$R^5$, wherein $R^5$ is selected from hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondary-alkyl, $C_{1-6}$tertiary-alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino $C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl;
X is attached to the C2 carbon of the selenophene ring or to the C3 carbon of the seleneophene ring, and X is selected from the group consisting of $NR^6$, O, S, S(O), and $S(O)_2$; wherein $R^6$ is selected from hydrogen, amino, $C_{1-6}$alkyl, and halo$C_{1-6}$alkyl;
$R^1$, $R^2$, $R^3$ and $R^4$ are independently selected from the group consisting of hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondary-alkyl, $C_{1-6}$tertiary-alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl) aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino $C_{1-6}$alkyl, amino $C_{1-6}$alkoxy, $C_{1-6}$alkylamino$C_{1-6}$alkyl, di($C_{1-6}$alkyl) amino $C_{1-6}$alkyl, $C_{1-6}$alkylsulfinyl, $C_{1-6}$alkylsulfonyl, and a aryl, heteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$ alkyl, di($C_{1-6}$alkyl)amino$C_{1-6}$alkyl, $C_{1-6}$alkylsulfinyl, and $C_{1-6}$alkylsulfonyl.

Various embodiments disclosed herein provide the geometrical isomers, optical isomers, diastereomers, and hydrates of the compounds of formula (I).

Various embodiments disclosed herein provide a process for preparing the compounds of formula (I). In certain embodiments, a selenophene compound of formula (I) according to claim 1 or a salt thereof is prepared by reacting a compound of formula II with a compound of formula III or a compound of formula IV in the presence of a solvent and optionally in the presence of a base selected from the group consisting of organic and inorganic bases. In various embodiments, Y in formula II is N or $CR^5$, and ring A in formula II is a fused benzene, pyridine, pyrazine, pyrimidine, pyridazine, thiophene, furan, pyrrole, selenophene, oxazole, isoxazole, imidazole, pyrazole, thiazole, or isothiazole ring.

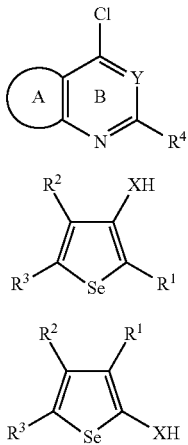

Formula II

Formula III

Formula IV

In other embodiments, a selenophene compound of formula (I) according to claim 1 or a salt thereof is prepared by reacting a compound of formula V with dimethylformamide-dimethylacetal or triethylorthoformate or trimethylorthoformate in the presence of a protic solvent; and the reacting the product with a compound of formula IIIa or IVa. In various embodiments, ring A in formula V is a fused benzene, pyridine, pyrazine, pyrimidine, pyridazine, thiophene, furan, pyrrole, selenophene, oxazole, isoxazole, imidazole, pyrazole, thiazole, or isothiazole ring.

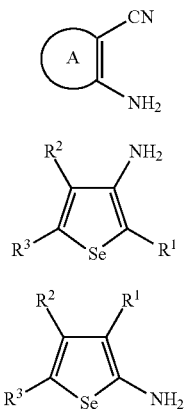

Formula V

Formula IIIa

Formula IVa

Various embodiments disclosed herein provide a selenophene compound having formula (VI), where X, Y, and $R^1$-$R^4$ are as defined in the compound of Formula I:

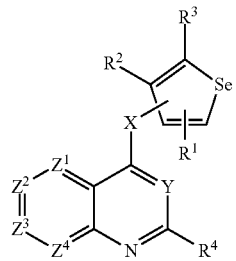

VI wherein:
$Z^1$, $Z^2$, $Z^3$, and $Z^4$ are independently selected from the group consisting of N and C—$R^7$, wherein each $R^7$ is independently selected from the group consisting of hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondary-alkyl, $C_{1-6}$tertiary-alkyl, $C_{2-6}$ alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl, phenyl, benzyl, a five-membered heteroaromatic ring containing at least one heteroatom selected from the group consisting of sulfur, oxygen, nitrogen and selenium, and a group having the following formula:

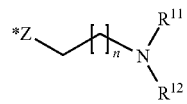

wherein n is 0 to 5;
* indicates a point of attachment to the benzene ring;
Z is selected from the group consisting of $CH_2$, O, S, or NH; and
$R^{11}$ and $R^{12}$ are independently selected from the group consisting of hydrogen, $C_{1-6}$alkyl, halo$C_{1-6}$alkyl, halo$C_{1-6}$alkoxy, and $C_{3-7}$cycloalkyl; or $R^{11}$ and $R^{12}$, together with the nitrogen atom to which they are attached, form a 5- to 7-membered heterocycloalkyl ring;
wherein phenyl and said five-membered heteroaromatic ring are optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$ alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino $C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, or $C_{1-6}$alkylsulfonyl; and
wherein said five-membered heteroaromatic ring contains no more than one oxygen or sulfur or selenium atom.

In various embodiments of the compound of formula VI, $Z^1$, $Z^2$, $Z^3$, and $Z^4$ are each C—$R^7$, i.e., $Z^1$, $Z^2$, $Z^3$, and $Z^4$, together with the atoms to which $Z^1$ and $Z^4$ are attached, define a benzene ring. Alternatively, $Z^1$, $Z^2$, $Z^3$, and $Z^4$ are independently selected from the group consisting of N and C—$R^7$, with the proviso that at least one of $Z^1$, $Z^2$, $Z^3$, and $Z^4$ is N, i.e., $Z^1$, $Z^2$, $Z^3$, and $Z^4$ define a pyridine, pyrazine, pyrimidine, pyridazine or triazine ring.

In some embodiments of the compound of formula VI, $Z^1$, $Z^2$, $Z^3$, and $Z^4$ are independently selected from the group consisting of N and C—R, with the proviso that two of $Z^1$, $Z^2$, $Z^3$, and $Z^4$ are N. In some embodiments, $Z^1$ and $Z^4$ are each N, i.e., $Z^1$, $Z^2$, $Z^3$, and $Z^4$ define a pyrazine ring. In other embodiments, either both $Z^1$ and $Z^3$ or both $Z^2$ and $Z^4$ are N, defining a pyrimidine ring. Alternatively, $Z^1$, $Z^2$, $Z^3$, and $Z^4$ define a pyridazine ring, where $Z^1$ and $Z^2$ are N; $Z^2$ and $Z^3$ are N; or $Z^3$ and $Z^4$ are N.

Various embodiments disclosed herein provide a selenophene compound having formula (VII), where X, Y, and $R^1$-$R^4$ are as defined in the compound of Formula I, and $Z^5$, $Z^6$, and $Z^7$ are as defined above with regard to the compound of formula II:

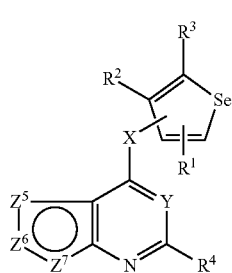

VII

In some embodiments of the compound of formula VII, $Z^5$, $Z^6$, and $Z^7$ are independently selected from the group consisting of S and C—$R^7$, with the proviso that one of $Z^5$, $Z^6$, and $Z^7$ is S, i.e., $Z^5$, $Z^6$, and $Z^7$ define a thiophene ring. In other embodiments of the compound of formula II, $Z^5$, $Z^6$, and $Z^7$ are independently selected from the group consisting of O and C—$R^7$, with the proviso that one of $Z^5$, $Z^6$, and $Z^7$ is O, i.e., $Z^5$, $Z^6$, and $Z^7$ define a furan ring. In certain embodiments, $Z^5$, $Z^6$, and $Z^7$ are independently selected from the group consisting of NH and C—$R^7$, with the proviso that one of $Z^5$, $Z^6$, and $Z^7$ is NH, i.e., $Z^5$, $Z^6$, and $Z^7$ define a pyrrole ring. In some embodiments, $Z^5$, $Z^6$, and $Z^7$ are independently selected from the group consisting of Se and C—$R^7$, with the proviso that one of $Z^5$, $Z^6$, and $Z^7$ is Se, i.e., $Z^5$, $Z^6$, and $Z^7$ define a selenophene ring.

In certain embodiments of the compound of formula VII, $Z^5$ is oxygen or nitrogen, $Z^6$ is C—$R^7$, and $Z^7$ is oxygen or nitrogen; with the proviso that $Z^5$ and $Z^7$ are not both nitrogen or both oxygen, i.e., $Z^5$, $Z^6$, and $Z^7$ define an oxazole ring. In other embodiments, one of $Z^5$, $Z^6$, and $Z^7$ is O; one of $Z^5$, $Z^6$, and $Z^7$ is N; and one of $Z^5$ and $Z^7$ is C—$R^7$, with the proviso that the ring contains an N—O bond, i.e., $Z^5$, $Z^6$, and $Z^7$ define an isoxazole ring.

In certain embodiments of the compound of formula VII, $Z^5$ is N or NH, $Z^6$ is C—$R^7$, and $Z^7$ is N or NH; where $Z^5$ and $Z^7$ are not both N or both NH, i.e., $Z^5$, $Z^6$, and $Z^7$ define an imidazole ring. In other embodiments, one of $Z^5$, $Z^6$, and $Z^7$ is N; one of $Z^5$, $Z^6$, and $Z^7$ is NH; and one of $Z^5$ and $Z^7$ is C—$R^7$, with the proviso that the ring contains an N—NH bond, i.e., $Z^5$, $Z^6$, and $Z^7$ define a pyrazole ring. In some embodiments, one of $Z^5$ and $Z^7$ is N; one of $Z^5$ and $Z^7$ is S; and $Z^6$ is C—$R^7$, with the proviso that the ring contains both S and N, i.e., $Z^5$, $Z^6$, and $Z^7$ define an thiazole ring. In other embodiments, one of $Z^5$, $Z^6$, and $Z^7$ is S; one of $Z^5$, $Z^6$, and $Z^7$ is N; and one of $Z^5$ and $Z^7$ is C—$R^7$, with the proviso that the ring contains an S—N bond, i.e., $Z^5$, $Z^6$, and $Z^7$ define an isothiazole ring.

Various embodiments disclosed herein provide pharmaceutical compositions comprising at least one 4-(selenophen-2(or 3)-ylamino) pyrimidine compound selected from the above formula (I) and derivatives thereof, in combination with at least one pharmaceutically acceptable excipient/carrier/diluents.

Various embodiments disclosed herein provide pharmaceutical compositions comprising at least one 4-(selenophen-2(or 3)-ylamino)pyrimidine compound selected from the above formula (I) and derivatives thereof, in combination with at least one pharmaceutically acceptable excipient/carrier/diluents and at least one anti-tumor agent.

Various embodiments disclosed herein provide a method of treating or inhibiting or controlling a cell proliferative disorder, particularly cancer in a patient in need of such treatment, comprising administering to the patient an effective amount of a compound of formula (I) or their compositions as defined above.

Various embodiments disclosed herein provide a method of treating or controlling tumor or cancer growth by blocking angiogenesis or by inhibiting vascular capillary formation with the administration of at least one selenophene compound of formula (I) or their salts or their compositions as defined above.

DESCRIPTION OF THE DRAWINGS

FIG. 1: Compound 27 inhibits capillary-like endothelial tube formation in vitro. Human umbilical vein endothelial cells (HUVECs) were laid on Cultrex coated plates in presence of either 10 ng/ml human recombinant Fibroblast Growth Factor (FGF) alone (B) or concomitantly with Compound 27 at 0.5, 1.0, 2.5 and 5 µg/ml C, D, E, and F, respectively. The cells in presence of treatments were allowed to form endothelial capillary tubes for 16 h at 37° C. Panel A represents capillary-like endothelial tube formation in 0.1% DMSO treated vehicle control wells.

DETAILED DESCRIPTION

The subject matter disclosed herein will now be described in detail in connection with certain preferred and optional embodiments, so that various aspects thereof may be more fully understood and appreciated.

The present compounds utilize a selenophene ring as a back bone in place of a benzene ring in 4-phenylaminoquinazoline to significantly increase activity for possible cure in the early stage diagnosis and to significantly increase efficacy in the treatment of late stage cancer. The reason that the selenophene ring system was chosen in place of an aromatic phenyl ring system is because selenium being larger atom in a five membered ring could resemble phenyl ring in the shape and size and attain phenyl ring structure in space. The receptors involved in recognizing the 4-phenylaminoquinazoline for example in gefetinib may also be recognized by the 4-selenophenylaminoquinazoline for biological response. In addition, selenium as an organometallic compound may have anticancer properties. Selenium is a well-recognized essential trace element in human, with doses of 55-90 µg required to maintain a healthy diet in humans (K. M. Aumann et al., *Org. Biomol. Chem.*, 2007, 5, 1276-1281). The selenium therefore, can be incorporated as an organometallic compound via aromatic selenophene ring system replaced for an aromatic phenyl system with significantly increased efficacy.

The proposed novel analogs with substitutents on the selenophene ring system will attain conformation that fits to the receptors on the tumor cell membrane in a Specific Conformational Perturbation (SCP) to afford physiological response. With this new design, all the molecules in a prearranged specific conformation will bind to the receptors one hundred percent of the time.

This would in turn afford high specificity with a larger window of the Therapeutic Index (TI). In general, for the treatment of cancer patients, a larger therapeutic index is preferred. This is because; one would like to start the therapeutic regimen with a very high Maximum Tolerated Dose (MTD) such that the cancer cells would be hit hard in the first chemotherapeutic treatment itself. Otherwise, the surviving cancer cells would repair the DNA damage and subsequently metastasize to the other tissues or organs. In addition, the cancer cells that survived from the first treatment would become resistant to the second or subsequent chemotherapy again, if needed. And besides, due to weakness of the immune system from the first chemotherapy, a suboptimal dose would be given in the second treatment that would contribute to toxicity more than the benefit.

As a part of developing novel anti-cancer compounds, twenty nine 4-selenophen-2(or 3)-ylaminopyrimidine compounds of formula (I) have been prepared and tested for their efficacy against three cancer cell lines. It was found that these 4-selenophen-2(or 3)-ylaminoquinazoline compounds of the formula (I) showed good inhibition against A549 (lung), DU145 (prostate), and HT29 (colon) cancer cell lines in vitro. The inventors found very surprisingly that 4-selenophen-2(or 3)-ylaminoquinazoline analog (compound 5) of formula (I) showed approximately four times better potency in vitro compared to gefitinib (Iressa) in the inhibition of A549 lung cancer cell line. Similarly, the 4-selenophen-2(or 3)-ylaminoquinazoline analog (Compound 5) showed in A549 cell line, an $IC_{50}$ value of 4.6 µM compared to 16.6 µM exhibited by gefitinib. It was also found that 4-selenophen-2(or 3)-ylaminoquinazoline analog (compound 1) of formula (I) showed approximately two times better potency in vitro compared to gefitinib (Iressa) in the cell proliferation inhibition of A549 lung cancer cell line. This analog (Compound 1) showed in the same lung cancer cell line, an $IC_{50}$ value of 9.08 µM compared to 16.6 µM exhibited by gefitinib. Hence, the novel analogs (Compound 1 and compound 5) are significantly better than the marketed drug gefitinib (Iressa), in terms of in vitro efficacy. Thus more surprisingly, these two analogs (compound 1 and compound 5) similarly showed several times better potency in vitro compared to gefitinib (Iressa) in the inhibition of DU145 (prostate) and HT29 (colon) cancer cell lines and these results are summarized in Table 1.

As it can be seen from Table 2, compound 21 was sixteen, fifteen, and seventeen times, more potent than Iressa in Breast (MDA-MB-231), Hepatocellular (HepG2) and Cervical (HeLa) carcinoma cells, respectively. Likewise, Compound 27 is equally more potent than Iressa in the same three carcinoma cell lines tested in vitro.

As it is shown in FIG. 1, it is evident that compound 27 is functioning as anti-angiogenic by significantly inhibiting endothelial capillary formation in a dose dependent manner.

Even though selected compounds have been used to for purposes of demonstration, the disclosure encompasses all compounds of the formula (I) and their derivatives.

Accordingly, the disclosure provides substituted 4-(selenophen-2(or 3)-ylamino) pyrimidine compounds represented by the following formula (I) and pharmaceutically acceptable salts thereof.

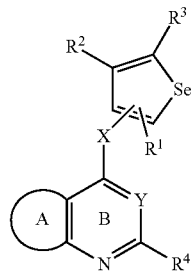

formula (I)

wherein:

A ring is aryl or heteroaryl or heterocycloalkyl; the aryl is fused benzene ring and heteroaryl is 6-membered aromatic fused ring containing one, two or three nitrogen atoms; or the heteroaryl is 5-membered aromatic fused ring containing one or more heteroatoms selected from sulfur, oxygen, nitrogen and selenium, providing that no more than one oxygen or sulfur or selenium atom is present; such rings include pyridine, pyridazine, pyrazine, pyrimidine, thiophene, furan, pyrrole, selenophene, pyrazole, imidazole, oxazole, isoxazole, thiazole and isothiazole; heterocycloalkyl in general represents a mono- or bicyclic, saturated heterocyclic radical having a total number of 3 to 10 carbon atoms and up to 2 heteroatoms and/or heterogroups independently selected from the group consisting of N, O, S, SO and $SO_2$;

A ring is optionally substituted by one, two or more groups independently selected from hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondary-alkyl, $C_{1-6}$tertiary-alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino $C_{1-6}$alkoxy, $C_{1-6}$alkylamino$C_{1-6}$alkyl, di($C_{1-6}$alkyl)amino $C_{1-6}$alkyl, $C_{1-6}$alkylsulfinyl, $C_{1-6}$alkylsulfonyl, and a aryl, heteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino $C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl;

Y is N or C—$R^5$, wherein $R^5$ is selected from hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondary-alkyl, $C_{1-6}$tertiary-alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino $C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl;

X may be attached to either 2$^{nd}$ or 3$^{rd}$ position of the selenophene ring;

X is selected from NR$^6$, O, S, S(O), S(O$_2$); wherein R$^6$ is selected from hydrogen, amino, C$_{1-6}$alkyl, haloC$_{1-6}$alkyl;

R$^1$, R$^2$, R$^3$, and R$^4$ selected from hydrogen, halogen, hydroxy, formyl, carboxylic acid, amino, nitro, cyano, sulfonic acid, thiole, trihalomethyl, sulfonamide, C$_{1-6}$alkyl, C$_{1-6}$secondary-alkyl, C$_{1-6}$tertiary-alkyl, C$_{2-6}$alkenyl, C$_{2-6}$alkynyl, C$_{1-4}$alkylcarbonyl, C$_{1-6}$alkoxycarbonyl, aminocarbonyl, C$_{1-6}$alkylaminocarbonyl, di(C$_{1-6}$alkyl)aminocarbonyl, haloC$_{1-6}$alkyl, hydroxyC$_{1-6}$alkyl, C$_{1-6}$alkoxy, haloC$_{1-6}$alkoxy, hydroxyC$_{1-6}$alkoxy, C$_{3-7}$cycloalkyl, C$_{3-7}$cycloalkoxy, C$_{1-6}$alkylamino, di(C$_{1-6}$alkyl)amino, aminoC$_{1-6}$alkyl, aminoC$_{1-6}$alkoxy, C$_{1-6}$alkylaminoC$_{1-6}$alkyl, di(C$_{1-6}$alkyl)aminoC$_{1-6}$alkyl, C$_{1-6}$alkylsulfinyl, C$_{1-6}$alkylsulfonyl, and a aryl, heteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, C$_{1-6}$alkyl, C$_{2-6}$alkenyl, C$_{2-6}$alkynyl, C$_{1-4}$alkylcarbonyl, C$_{1-4}$alkoxycarbonyl, aminocarbonyl, C$_{1-6}$alkylaminocarbonyl, di(C$_{1-6}$alkyl) aminocarbonyl, haloC$_{1-6}$alkyl, hydroxyC$_{1-6}$alkyl, C$_{1-6}$alkoxy, haloC$_{1-6}$alkoxy, hydroxyC$_{1-6}$alkoxy, C$_{3-7}$cycloalkyl, C$_{3-7}$cycloalkoxy, C$_{1-6}$alkylamino, di(C$_{1-6}$alkyl)amino, aminoC$_{1-6}$alkyl, amino C$_{1-6}$alkoxy, C$_{1-6}$alkylaminoC$_{1-6}$alkyl, di(C$_{1-6}$alkyl)aminoC$_{1-6}$alkyl, C$_{1-6}$alkylsulfinyl, C$_{1-6}$alkylsulfonyl;

In a preferred embodiment, the disclosure provides substituted 4-(selenophen-2(or 3)-ylamino)pyrimidine compounds represented by the following formula (I),

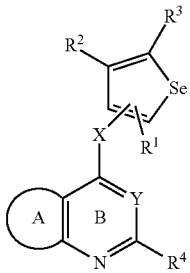

formula (I)

Wherein the X may be attached to either 2$^{nd}$ or 3$^{rd}$ position of the selenophene ring and is selected from the following;

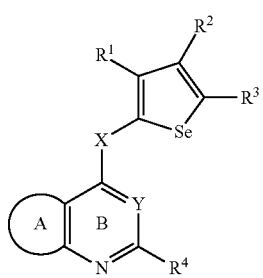 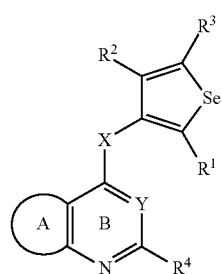

In another embodiment, the disclosure provides selenophene compounds of formula (I), wherein X is NR$^6$;

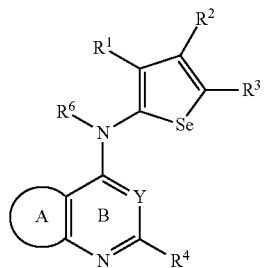 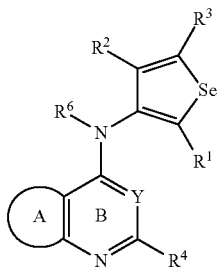

wherein R$^6$ is selected from hydrogen, amino, C$_{1-6}$alkyl, haloC$_{1-6}$alkyl;

In another embodiment, the disclosure provides selenophene compounds of formula (I), wherein X is O;

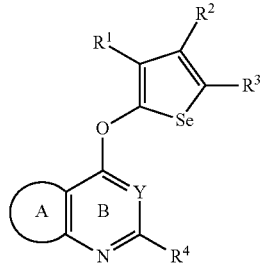 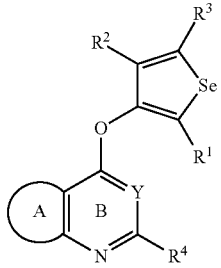

In another embodiment, the disclosure provides selenophene compounds of formula (I), wherein Y is N;

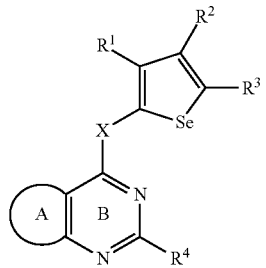 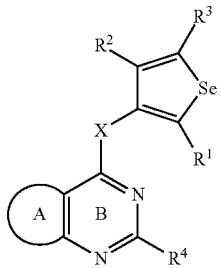

In another embodiment, the disclosure provides selenophene compounds of formula (I), wherein Y is C—R$^5$;

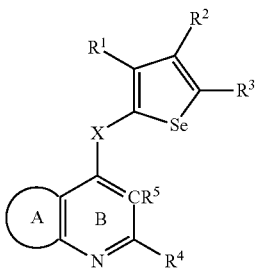 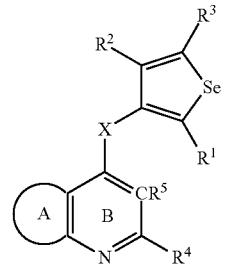

wherein R$^5$ is selected from hydrogen, halogen, hydroxy, formyl, carboxylic acid, amino, nitro, cyano, sulfonic acid, thiole, trihalomethyl, sulfonamide, C$_{1-6}$alkyl, C$_{1-6}$secondary-alkyl, $C_{1-6}$tertiary-alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl;

In another embodiment, the disclosure provides substituted 4-(selenophen-2(or 3)-ylamino)pyrimidine compounds represented by the formula (I), wherein A ring is optionally substituted aryl or optionally substituted heteroaryl; the optionally substituted aryl group is 6-membered aromatic ring and the resultant fused system is substituted or unsubstituted 4-selenophen-2(or 3)-ylaminoquinazoline. For example the 6-membered aromatic ring is substituted or unsubstituted benzene. The 6-membered aromatic ring is selected from substituted or unsubstituted benzene ring having the following structure;

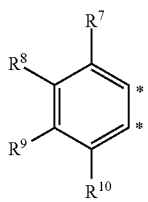

wherein * indicates the point of attachment to B ring of formula I and is selected from the following;

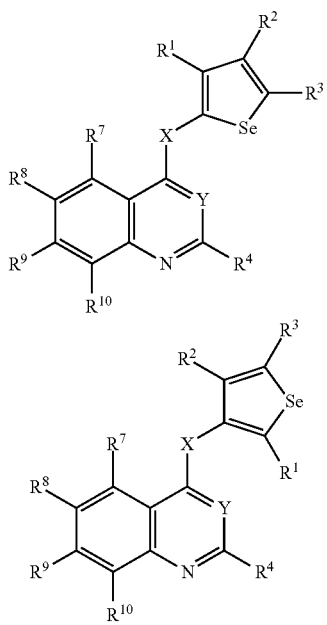

wherein:
$R^7, R^8, R^9$ and $R^{10}$
is independently selected from hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondary-alkyl, $C_{1-6}$tertiary-alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl, and a phenyl, benzyl, a five membered heteroaromatic ring containing one or more heteroatoms selected from sulfur, oxygen, nitrogen and selenium, providing that no more than one oxygen or sulfur or selenium atom is present; phenyl or 5-membered heteroaromatic ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl;

optionally
at least one of $R^7, R^8, R^9$ and $R^{10}$ may be selected from the following formula;

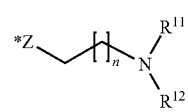

wherein:
n is an integer selected from 0, 1 to 5; preferably 2;
* indicates the point of attachment to the benzene ring;
Z is selected from $CH_2$, O, S, or NH;
$R^{11}$ and $R^{12}$
is independently selected from hydrogen, $C_{1-6}$alkyl, halo$C_{1-6}$alkyl, halo$C_{1-6}$alkoxy, $C_{3-7}$cycloalkyl;
optionally $R^{11}$ and $R^{12}$
are joined, and taken together with the atoms to which they are attached, form a 5- to 7-membered heterocycloalkyl ring;

In another embodiment, the disclosure provides substituted 4-(selenophen-2(or 3)-ylamino)pyrimidine compounds represented by the formula (I), wherein A ring is selected from pyridine and the resultant fused system is substituted or unsubstituted 4-(selenophen-2(or 3)-ylaminopyridino)pyrimidine. The pyridine ring is selected from the following;

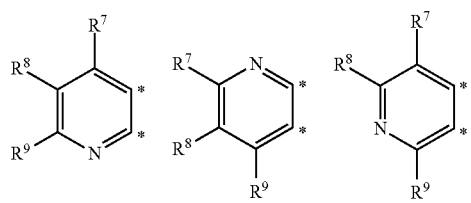

-continued

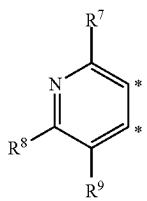

wherein:

* indicates the point of attachment to B ring of formula I; the bond which is fused to ring B is either 2,3 or 3, 2 or 3, 4 or 4,3 of pyridine and is selected from the following;

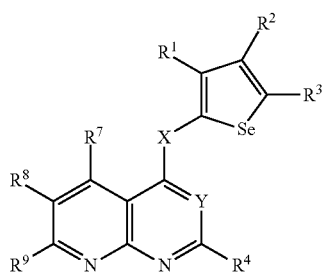

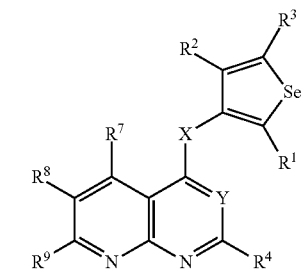

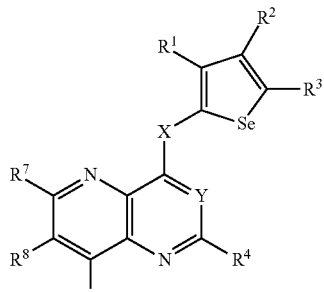

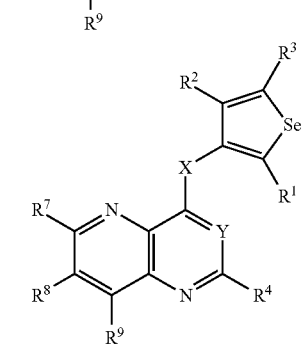

-continued

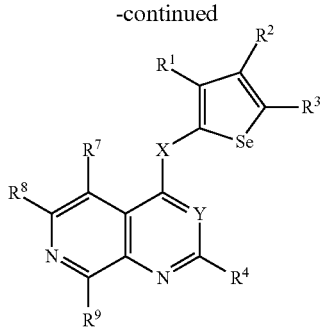

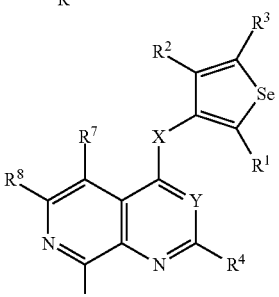

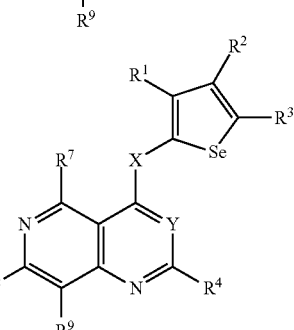

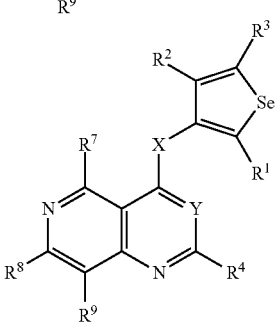

$R^7$, $R^8$, and $R^9$
is independently selected from the groups specified above;

In another embodiment, the disclosure provides substituted 4-(selenophen-2(or 3)-ylamino)pyrimidine compounds represented by the formula (I), wherein A ring is selected from pyrazine and the resultant fused system is substituted or unsubstituted 4-(selenophen-2(or 3)-ylaminopyrazino)pyrimidine. The pyrazine ring is selected from the following;

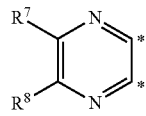

wherein:
* indicates the point of attachment to B ring of formula I and is selected from the following;

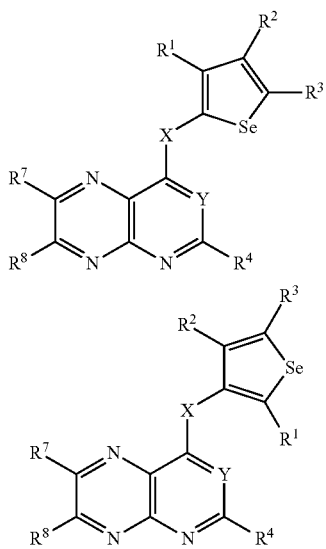

$R^7$, and $R^8$ is independently selected from the groups specified above;

In another embodiment, the disclosure provides substituted 4-(selenophen-2(or 3)-ylamino)pyrimidine compounds represented by the formula (I), wherein A ring is selected from pyrimidine and the resultant fused system is substituted or unsubstituted 4-(selenophen-2(or 3)-ylaminopyrimidino) pyrimidine. The pyrimidine ring is selected from the following;

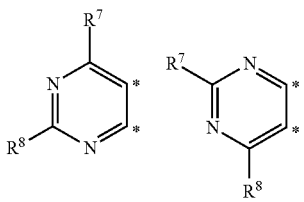

wherein:

* indicates the point of attachment to B ring of formula I; the bond which is fused to ring B is either 4, 5 or 5,4 of pyrimidine and is selected from the following;

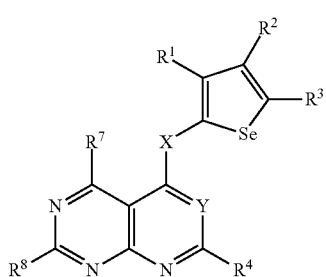

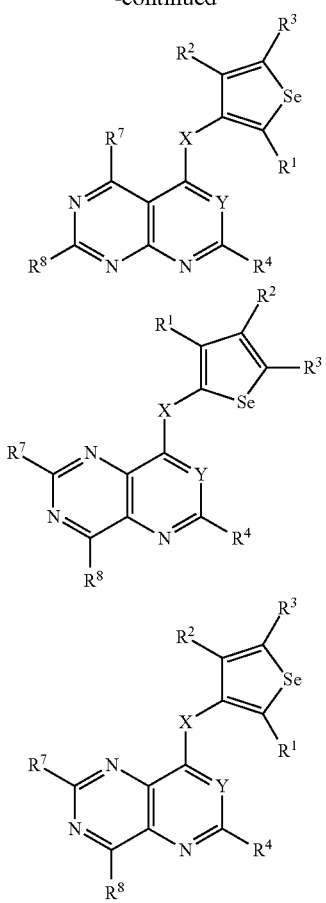

$R^7$, and $R^8$ is independently selected from the groups specified above;

In another embodiment, the disclosure provides substituted 4-(selenophen-2(or 3)-ylamino)pyrimidine compounds represented by the formula (I), wherein A ring is selected from pyridazine and the resultant fused system is substituted or unsubstituted 4-(selenophen-2(or 3)-ylaminopyridazino) pyrimidine. The pyridazine ring is selected from the following;

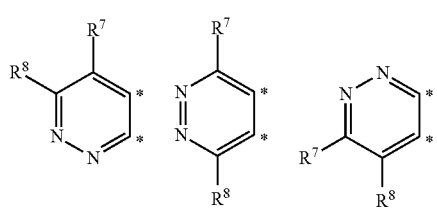

wherein:

* indicates the point of attachment to B ring of formula I; the bond which is fused to ring B is either 3, 4 or 4, 5 or 4,3 of pyridazine and is selected from the following;

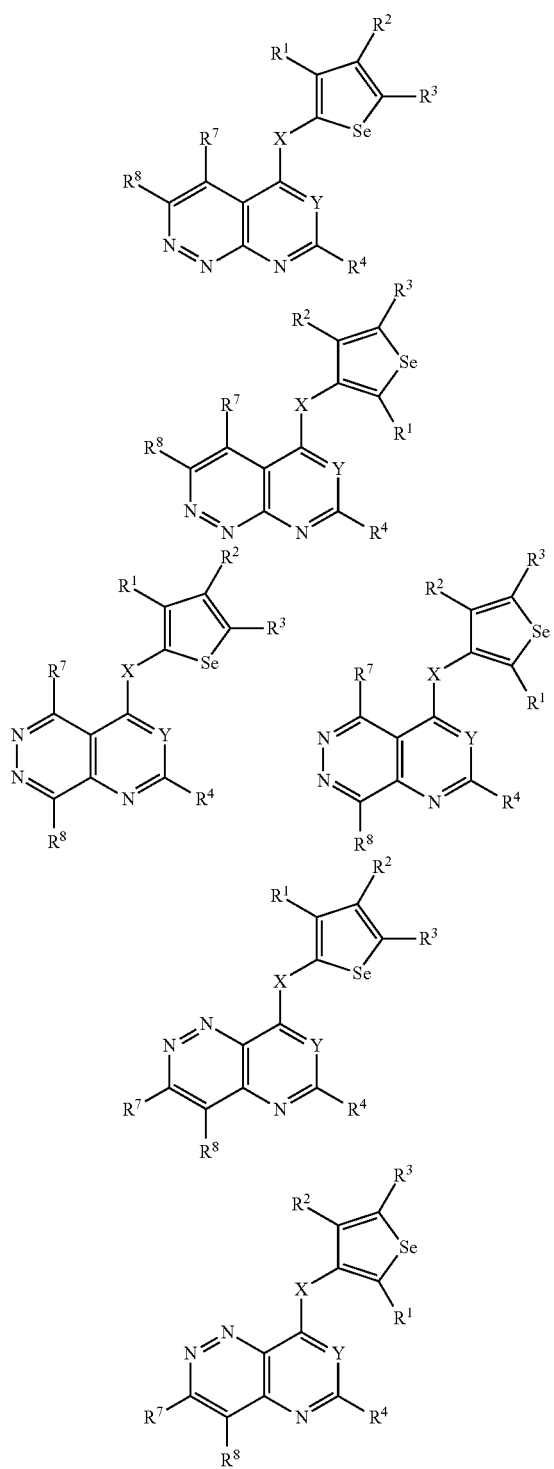

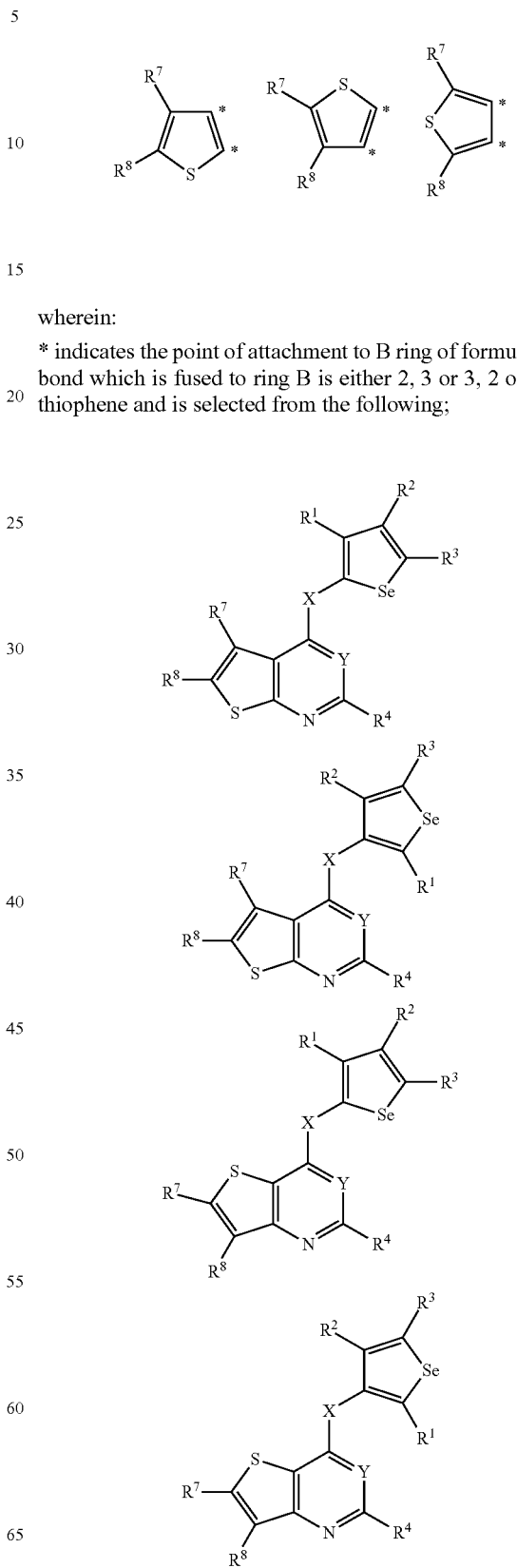

R[7], and R[8]
is independently selected from the groups specified above;

In another embodiment, the disclosure provides substituted 4-(selenophen-2(or 3)-ylamino)pyrimidine compounds represented by the formula (I), wherein A ring is selected from thiophene and the resultant fused system is substituted or unsubstituted 4-(selenophen-2(or 3)-ylaminothieno)pyrimidine. The thiophene ring is selected from the following;

wherein:
* indicates the point of attachment to B ring of formula I; the bond which is fused to ring B is either 2, 3 or 3, 2 or 3,4 of thiophene and is selected from the following;

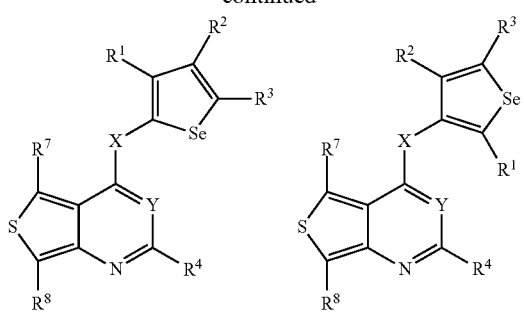

R⁷, and R⁸
is independently selected from the groups specified above;

In another embodiment, the disclosure provides substituted 4-(selenophen-2(or 3)-ylamino)pyrimidine compounds represented by the formula (I), wherein A ring is selected from furan and the resultant fused system is substituted or unsubstituted 4-(selenophen-2(or 3)-ylaminofurano)pyrimidine. The furan ring is selected from the following;

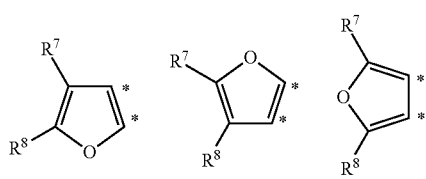

wherein:
* indicates the point of attachment to B ring of formula I; the bond which is fused to ring B is either 2, 3 or 3, 2 or 3,4 of furan and is selected from the following;

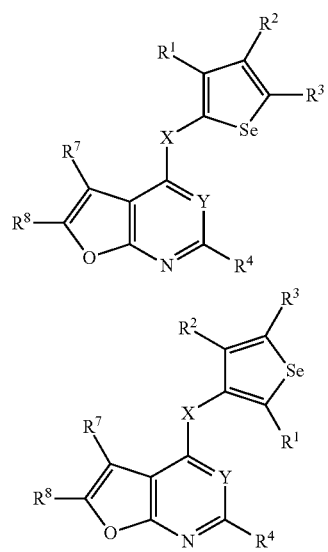

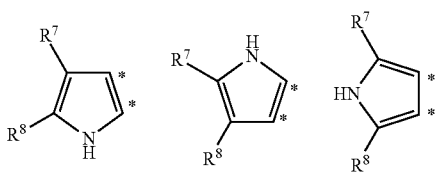

R⁷, and R⁸
is independently selected from the groups specified above;

In another embodiment, the disclosure provides substituted 4-(selenophen-2(or 3)-ylamino)pyrimidine compounds represented by the formula (I), wherein A ring is selected from pyrrole and the resultant fused system is substituted or unsubstituted 4-(selenophen-2(or 3)-ylaminopyrrolo)pyrimidine. The pyrrole ring is selected from the following;

wherein:
* indicates the point of attachment to B ring of formula I; the bond which is fused to ring B is either 2, 3 or 3, 2 or 3,4 of pyrrole and is selected from the following;

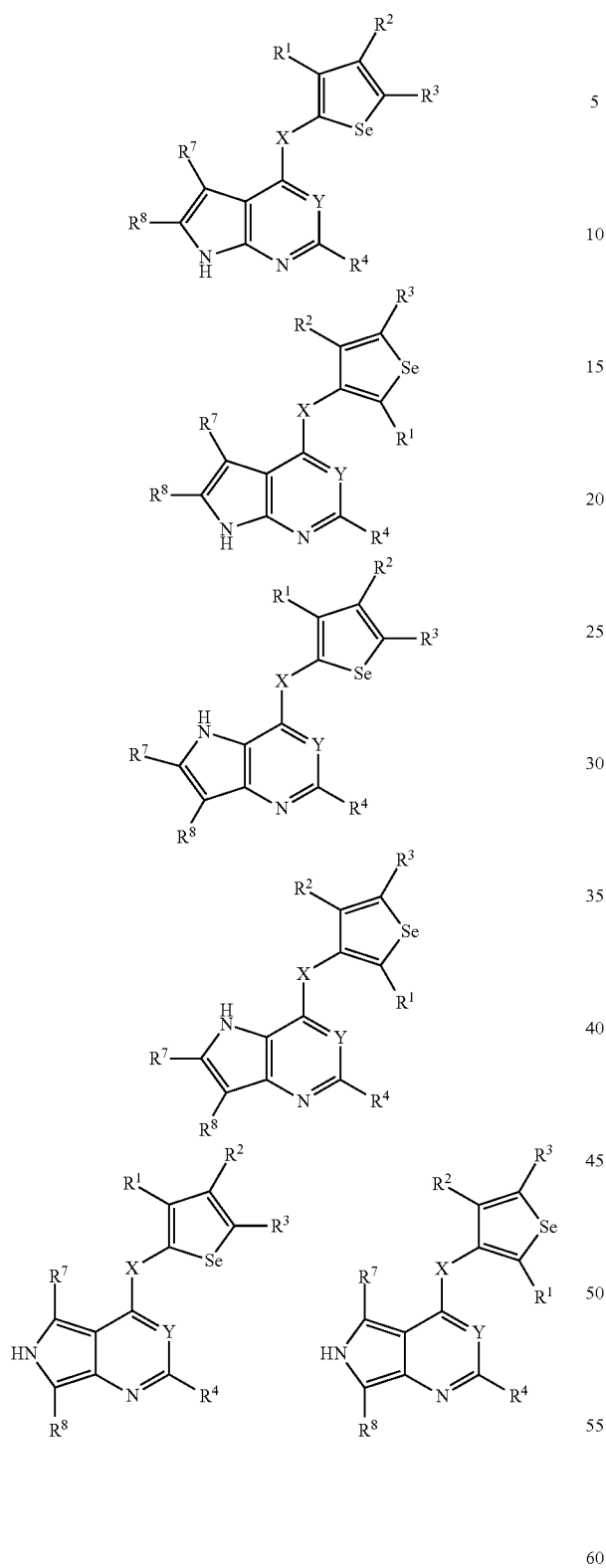

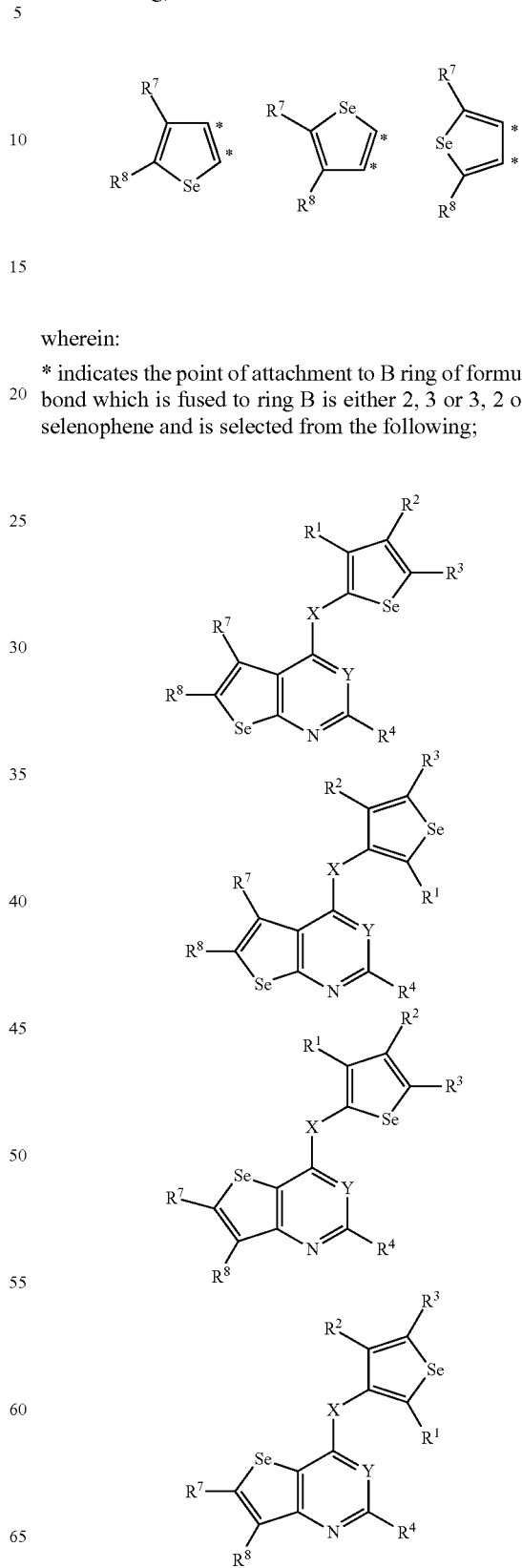

$R^7$, and $R^8$
is independently selected from the groups specified above;

In another embodiment, the disclosure provides substituted 4-(selenophen-2(or 3)-ylamino)pyrimidine compounds represented by the formula (I), wherein A ring is selected from selenophene and the resultant fused system is substituted or unsubstituted 4-(selenophen-2(or 3)-ylaminoselenopheno)pyrimidine. The selenophene ring is selected from the following;

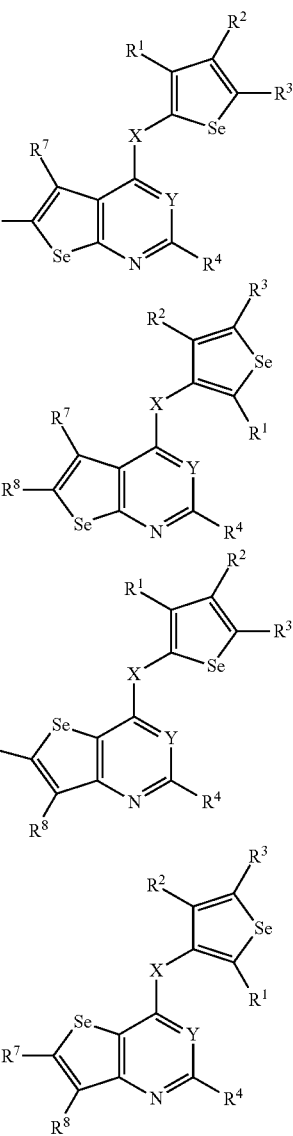

wherein:
* indicates the point of attachment to B ring of formula I; the bond which is fused to ring B is either 2, 3 or 3, 2 or 3,4 of selenophene and is selected from the following;

-continued

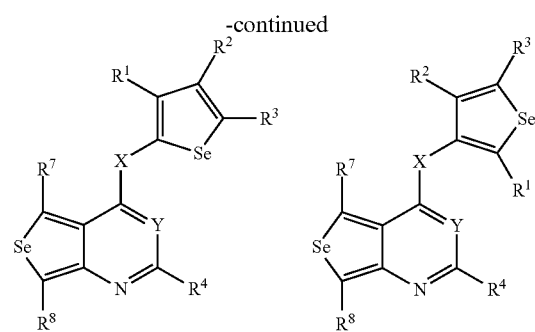

R⁷, and R⁸ is independently selected from the groups specified above;

In another embodiment, the disclosure provides substituted 4-(selenophen-2(or 3)-ylamino)pyrimidine compounds represented by the formula (I), wherein A ring is selected from oxazole and the resultant fused system is substituted or unsubstituted 4-(selenophen-2(or 3)-ylaminooxazolo)pyrimidine. The oxazole ring is selected from the following;

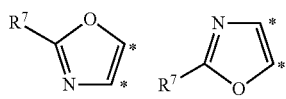

wherein:

* indicates the point of attachment to B ring of formula I; the bond which is fused to ring B is either 4, 5 or 5,4 of oxazole and is selected from the following;

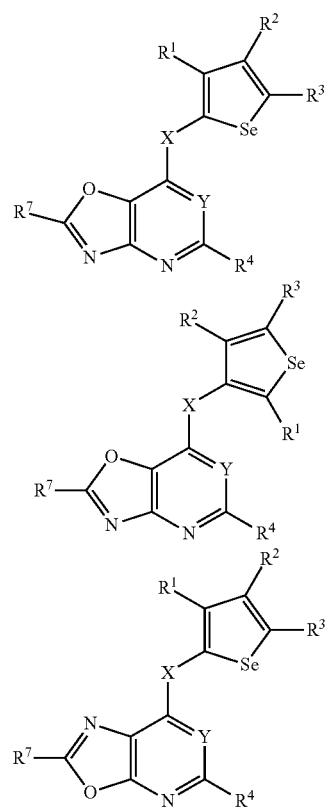

-continued

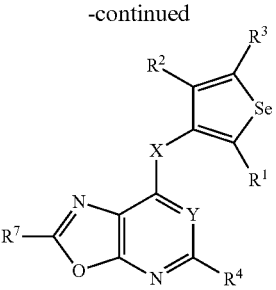

R⁷ is independently selected from the groups specified above;

In another embodiment, the disclosure provides substituted 4-(selenophen-2(or 3)-ylamino)pyrimidine compounds represented by the formula (I), wherein A ring is selected from isoxazole and the resultant fused system is substituted or unsubstituted 4-(selenophen-2(or 3)-ylaminoisoxazolo)pyrimidine. The isoxazole ring is selected from the following;

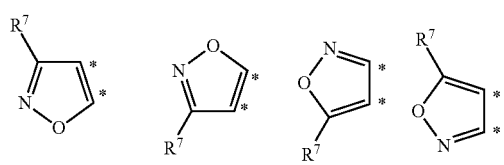

wherein:

* indicates the point of attachment to B ring of formula I; the bond which is fused to ring B is either 5, 4 or 4, 5 or 4, 3 or 3,4 of isoxazole and is selected from the following;

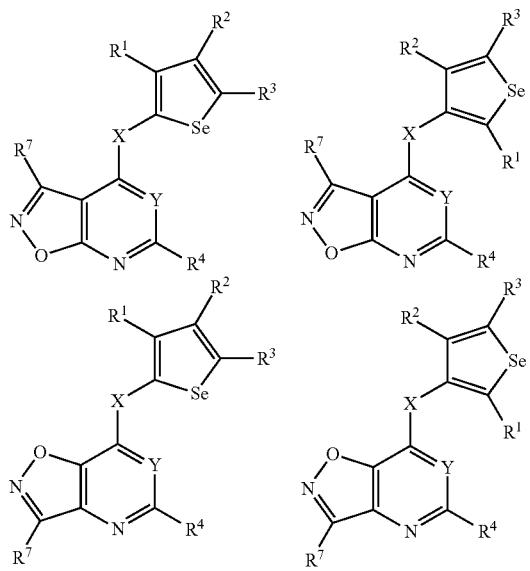

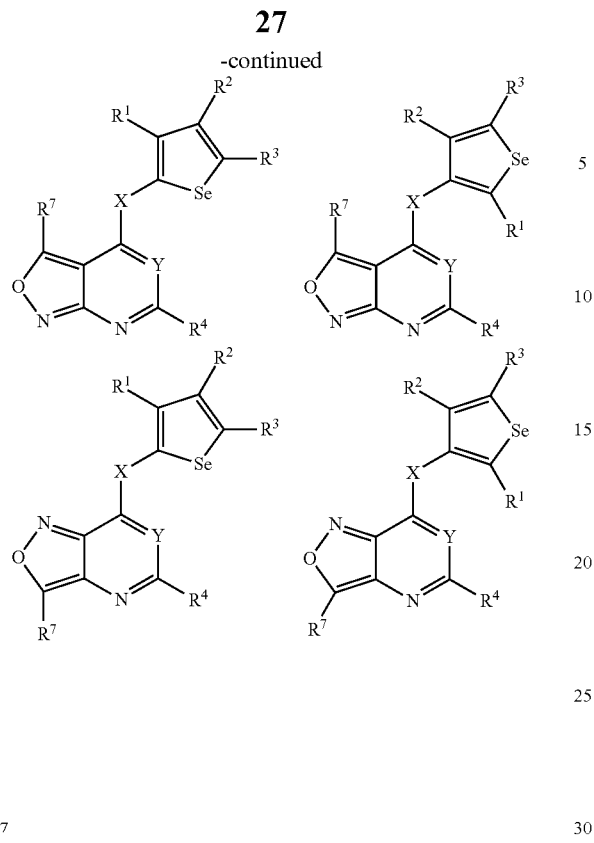

R[7]
is independently selected from the groups specified above;

In another embodiment, the disclosure provides substituted 4-(selenophen-2(or 3)-ylamino)pyrimidine compounds represented by the formula (I), wherein A ring is selected from imidazole and the resultant fused system is substituted or unsubstituted 4-(selenophen-2(or 3)-ylaminoimidazolo) pyrimidine. The imidazole ring is selected from the following;

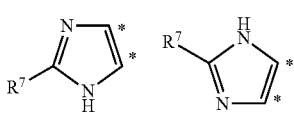

wherein:
* indicates the point of attachment to B ring of formula I; the bond which is fused to ring B is either 5, 4 or 4,5 of imidazole and is selected from the following;

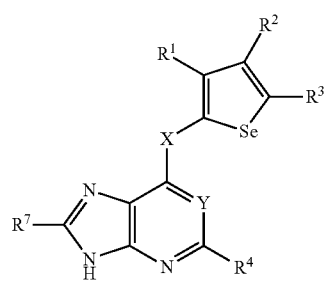

R[7]
is independently selected from the groups specified above;

In another embodiment, the disclosure provides substituted 4-(selenophen-2(or 3)-ylamino)pyrimidine compounds represented by the formula (I), wherein A ring is selected from pyrazole and the resultant fused system is substituted or unsubstituted 4-(selenophen-2(or 3)-ylaminopyrazolo)pyrimidine. The pyrazole ring is selected from the following;

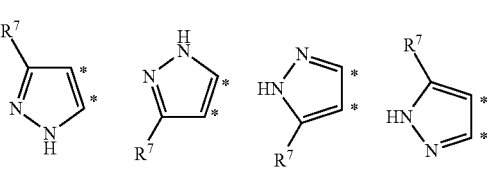

wherein:
* indicates the point of attachment to B ring of formula I; the bond which is fused to ring B is either 5, 4 or 4, 5 or 4, 3 or 3,4 of pyrazole and is selected from the following;

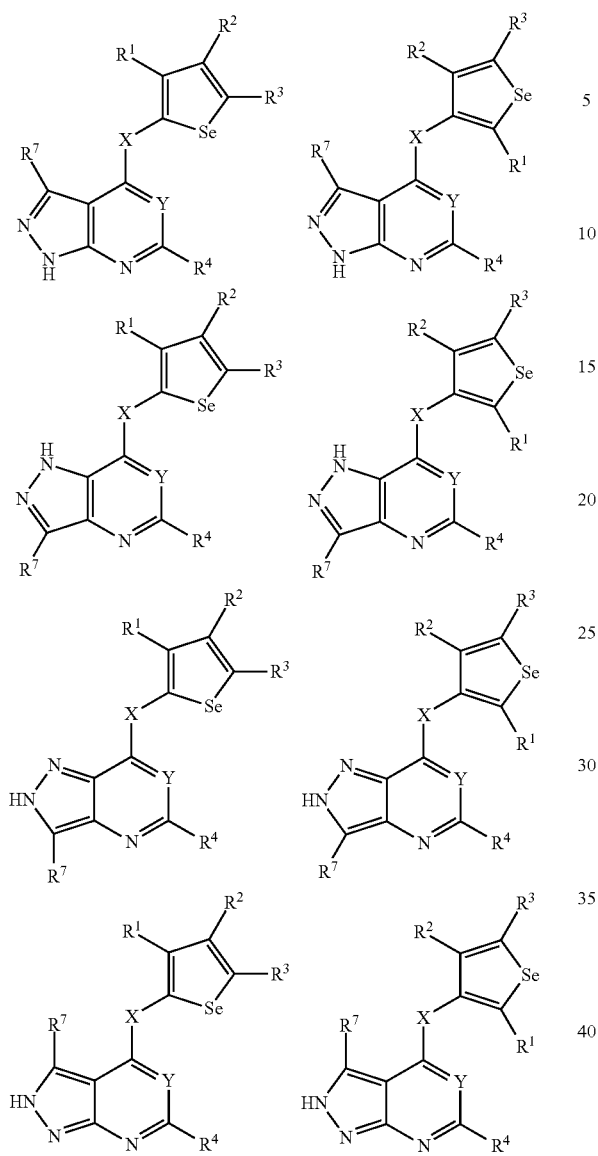

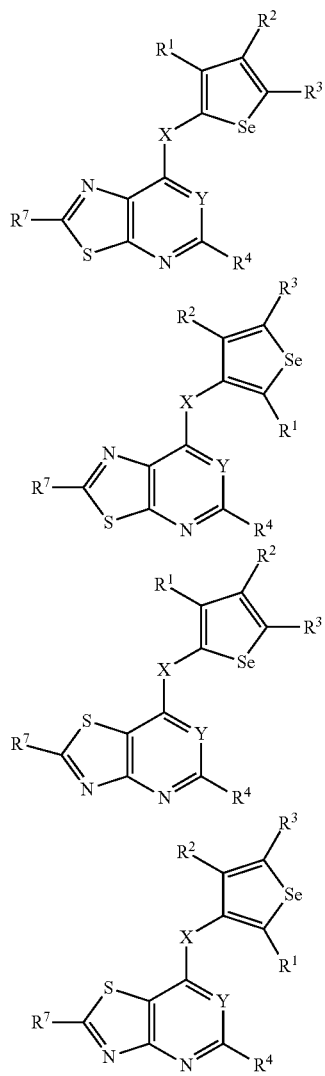

R⁷ is independently selected from the groups specified above;

In another embodiment, the disclosure provides substituted 4-(selenophen-2(or 3)-ylamino)pyrimidine compounds represented by the formula (I), wherein A ring is selected from thiazole and the resultant fused system is substituted or unsubstituted 4-(selenophen-2(or 3)-ylaminothiazolo)pyrimidine. The thiazole ring is selected from the following;

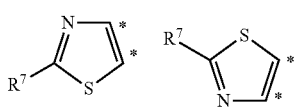

wherein:

* indicates the point of attachment to B ring of formula I; the bond which is fused to ring B is either 5, 4 or 4,5 of thiazole and is selected from the following;

R⁷ is independently selected from the groups specified above;

In another embodiment, the disclosure provides substituted 4-(selenophen-2(or 3)-ylamino)pyrimidine compounds represented by the formula (I), wherein A ring is selected from isothiazole and the resultant fused system is substituted or unsubstituted 4-(selenophen-2(or 3)-ylaminoisothiazolo)pyrimidine. The isothiazole ring is selected from the following;

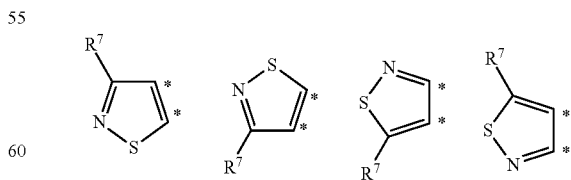

wherein:

* indicates the point of attachment to B ring of formula I; the bond which is fused to ring B is either 5, 4 or 4, 5 or 4, 3 or 3,4 of isothiazole;

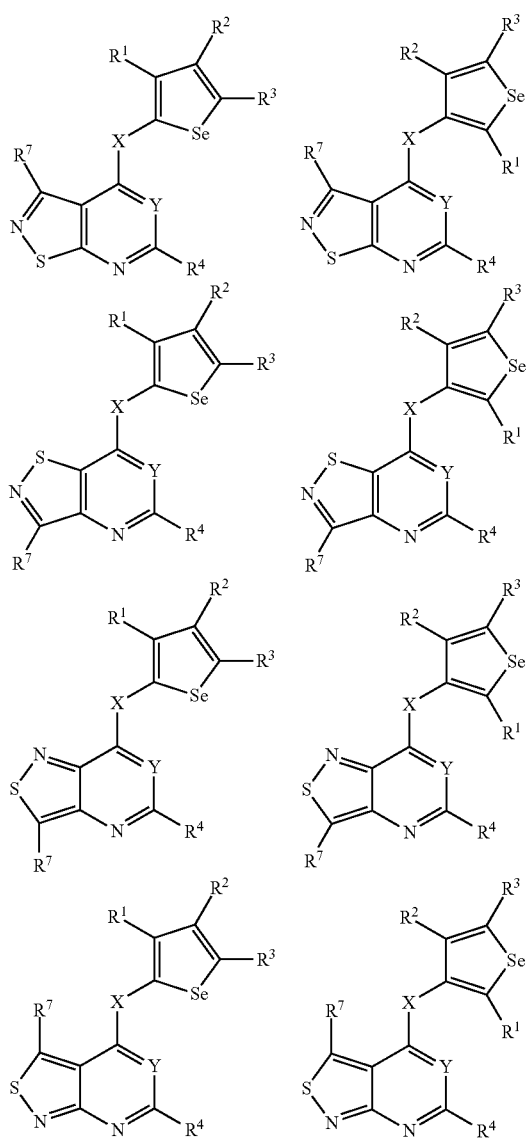

R⁷
is independently selected from the groups specified above;
Unless otherwise stated, the following definitions apply for the substituents and residues used throughout this specification and claims:

Alkyl in general represents a normal alkyl, secondary alkyl or tertiary alkyl having 1 to 6 carbon atoms. Non-limiting examples include methyl, ethyl, n-propyl, iso-propyl, n-butyl, isobutyl, sec-butyl, tert-butyl, pentyl, isopentyl, neopentyl, hexyl, isohexyl. The same applies to radicals such as alkylcarbonyl, alkoxy, alkylamino, dialkylamino, alkylsulfonyl, haloakyl and the like.

Alkenyl in general represents a straight-chain or branched unsaturated hydrocarbon radical having 2 to 6 carbon atoms and one carbon-carbon double bond. Non-limiting examples include —CH=CH₂, —CH=CHCH₃, —C(CH₃)=CH₂, —CH₂CH=CH₂, CH=C(CH₃)₂, —C(CH₃)=CHCH₃, —CH₂CH=CHCH₃, —CH₂C(CH₃)=CH₂, —CH₂CH₂CH=CH₂, —CH₂CH=CHCH₂CH₃, —CH₂CH₂CH=CHCH₃, —CH₂CH=C(CH₃)₂, —CH₂CH₂C(CH₃)=CH₂, —CH=CHCH₂CH₂CH₃ etc.

Alkynyl in general represents a straight-chain or branched unsaturated hydrocarbon radical having 2 to 6 carbon atoms and one carbon-carbon triple bond. Non-limiting examples include —C≡CH, —C≡CCH₃, —CH₂C≡CH, —C≡CCH₂CH₃, —CH₂CH₂C≡CH, —CH₂C≡CCH₃ etc.

Alkoxy illustratively and preferably represents methoxy, ethoxy, n-propoxy, isopropoxy, n-butoxy and tert-butoxy etc.

Alkylcarbonyl in general represents a straight-chain or branched alkyl radical having 1 to 6 carbon atoms which is bonded via a carbonyl group to the rest of the molecule. Non-limiting examples include acetyl, n-propionyl, n-butyryl, isobutyryl, pivaloyl.

Alkoxycarbonyl illustratively and preferably represents methoxycarbonyl, ethoxycarbonyl, n-propoxycarbonyl, isopropoxycarbonyl, n-butoxycarbonyl and tert-butoxycarbonyl etc.

Alkylsulfonyl in general represents a straight-chain or branched alkyl radical having 1 to 6 carbon atoms which is bonded via a sulfonyl (—SO₂—) group to the rest of the molecule. Non-limiting examples include methylsulfonyl, ethylsulfonyl, n-propylsulfonyl, isopropylsulfonyl, n-butylsulfonyl, tert-butylsulfonyl etc.

Monoalkylamino in general represents an amino radical having one alkyl residue attached to the nitrogen atom. Non-limiting examples include methylamino, ethylamino, n-propylamino, isopropylamino, n-butylamino, tert-butylamino. The same applies to radicals such as monoalkyl aminocarbonyl etc.

Dialkylamino in general represents an amino radical having two independently selected alkyl residues attached to the nitrogen atom. Non-limiting examples include N,N-dimethylamino, NN-diethylamino, NN-diisopropylamino, N-ethyl-N-methylamino, N-methyl-N-n-propylamino, N-iso-propyl-N-n-propylamino, N-tert-butyl-N-methylamino.

Monoalkylaminocarbonyl illustratively and preferably represents methylaminocarbonyl, ethylaminocarbonyl, n-propylaminocarbonyl, isopropylaminocarbonyl, n-butylaminocarbonyl and tert-butylaminocarbonyl etc.

Dialkylaminocarbonyl illustratively and preferably represents N,N-dimethylaminocarbonyl, N,N-diethylaminocarbonyl, N,N-diisopropylaminocarbonyl, N-ethyl-N-methylaminocarbonyl, N-methyl-N-n-propylaminocarbonyl, N-isopropyl-N-n-propylaminocarbonyl and N-tert-butyl-N-methyl-aminocarbonyl etc.

Alkylcarbonylamino in general represents a straight-chain or branched alkyl radical having 1 to 6 carbon atoms which is bonded via a carbonylamino (—CO—NH—) group to the rest of the molecule and which is attached to the carbon atom of that group. Non-limiting examples include acetylamino, n-propionylamino, n-butyrylamino, isobutyrylamino, pivaloylamino etc.

Alkoxycarbonylamino illustratively and preferably represents methoxycarbonylamino, ethoxycarbonylamino, n-propoxycarbonylamino, isopropoxycarbonylamino, n-butoxycarbonylamino and tert.-butoxycarbonylamino etc.

Cycloalkyl in general represents a mono-, bi- or tricyclic saturated hydrocarbon radical having 3 to 7 carbon atoms. Preference is given to monocyclic cycloalkyl radicals having 3 to 7 carbon atoms. Non-limiting examples include cyclopropyl, cyclobutyl, cyclopentyl, cyclohexyl, cycloheptyl, bicyclo[2.2.1]heptyl, adamantly etc.

Heterocycloalkyl in general represents a mono- or bicyclic, saturated heterocyclic radical having a total number of 3 to 10 carbon atoms and up to 2 heteroatoms and/or hetero-groups independently selected from the group consisting of N, O, S, SO and SO₂, which ring system can be bonded via a ring carbon atom or, if possible, via a ring nitrogen atom. Non-limiting examples include aziridinyl, azetidinyl, oxetanyl, thietanyl, pyrrolidinyl, pyrazolidinyl, tetrahydrofuranyl, thiolanyl, sulfolanyl, 1,3-dioxolanyl, 1,3-oxazolidinyl, 1,3-thiazolidinyl, piperidinyl, piperazinyl, tetrahydropyranyl, tetrahydrothiopyranyl, 1,3-dioxanyl, 1,4-dioxanyl, morpholinyl, thiomorpholinyl, 1,1-dioxidothiomo[phi]holinyl, perhydroazepinyl, perhydro-1,4-diazepinyl, perhydro-1,4-oxazepinyl, perhydroazocinyl, octahydropyrrolo[3,4-b]pyrrolyl, octahydroisoindolyl, octahydropyrrolo[3,4-b]pyridyl, octahydropyrrolo[1,2-a]pyrazinyl, decahydroisochinolinyl, 7-azabicyclo[2.2.1]heptyl, 3-azabicyclo[3.2.0]heptyl, 7-azabicyclo-[4.1.0]heptyl, 2,5-diazabicyclo[2.2.1]heptyl, 2-oxa-5-azabicyclo[2.2.1]heptyl, 2-azabicyclo[2.2.2]octyl, 3-azabicyclo[3.2.1]octyl, 8-azabicyclo[3.2.1]octyl, 8-oxa-3-azabicyclo[3.2.1]octyl, 3-oxa-9-azabicyclo[3.3.1]nonyl. Particular preference is given to 5- to 7-membered monocyclic heterocycloalkyl radicals having up to 2 heteroatoms selected from the group consisting of N, O and S, such as illustratively and preferably tetrahydrofuranyl, 1,3-dioxolanyl, pyrrolidinyl, tetrahydropyranyl, 1,4-dioxanyl, piperidinyl, piperazinyl, morpholinyl, thiomorpholinyl, perhydroazepinyl, perhydro-1,4-diazepinyl and perhydro-1,4-oxazepinyl.

Heteroaryl in general represents a monocyclic, aromatic heterocyclic radical having 5 or 6 ring atoms, including up to 3 heteroatoms independently selected from the group consisting of N, O, S and Se, which ring system can be bonded via a ring carbon atom or, if possible, via a ring nitrogen atom. Preference is given to 6-membered heteroaryl radicals having up to 2 nitrogen atoms, such as pyridyl, pyrimidyl, pyridazinyl and pyrazinyl, and to 5-membered heteroaryl radicals having up to 3 heteroatoms selected from the group consisting of N, O, S and Se, such as illustratively and preferably thienyl, furyl, pyrrolyl, selenophenyl, thiazolyl, oxazolyl, isothiazolyl, isoxazolyl, pyrazolyl, imidazolyl, oxadiazolyl, thiadiazolyl, triazolyl.

Halogen represents fluorine, chlorine, bromine and iodine.

The compounds according to this disclosure can also be present in the form of their salts, hydrates and/or solvates.

Salts for the purposes of the present disclosure are preferably pharmaceutically acceptable salts of the compounds according to the disclosure.

Pharmaceutically acceptable salts include acid addition salts of mineral acids, carboxylic acids and sulfonic acids, for example salts of hydrochloric acid, hydrobromic acid, nitric acid, sulfuric acid, phosphoric acid, methanesulfonic acid, ethanesulfonic acid, toluenesulfonic acid, benzenesulfonic acid, formamidinesulfonic acid, naphthalenedisulfonic acid, formic acid, acetic acid, propionic acid, lactic acid, tartaric acid, malic acid, citric acid, fumaric acid, maleic acid and benzoic acid.

Pharmaceutically acceptable salts also include salts of customary bases, such as for example and preferably alkali metal salts (for example sodium and potassium salts), alkaline earth metal salts (for example calcium and magnesium salts), and ammonium salts derived from ammonia or organic amines, such as illustratively and preferably ethylamine, diethylamine, triethylamine, ethyldiisopropylamine, monoethanolamine, diethanolamine, triethanol amine, dicyclohexylamine, dimethylaminoethanol, dibenzylamine, N-methylmorpholine, N-methylpiperidine, dehydroabietylamine, arginine, lysine, ethylenediamine and polyamines such as putrescine and cadaverine.

Hydrates of the compounds of the disclosure or their salts are stoichiometric compositions of the compounds with water, such as, for example, hemi-, mono-, or dihydrates.

Solvates of the compounds of the disclosure or their salts are stoichiometric compositions of the compounds with organic solvents.

The compounds of this disclosure may, either by nature of asymmetric centers or by restricted rotation, be present in the form of isomers (enantiomers, diastereomers). Any isomer may be present in which the asymmetric center is in the (R)-, (S)-, or (R,S) configuration.

It will also be appreciated that when two or more asymmetric centers are present in the compounds of the disclosure, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the disclosure.

Geometrical isomers by nature of substituents about a double bond or a ring may be present in cis (=Z-) or trans (=E-) form, and both isomeric forms are encompassed within the scope of this disclosure.

All isomers, whether separated, pure, partially pure, or in racemic mixture, of the compounds of this disclosure are encompassed within the scope of this disclosure. The purification of said isomers and the separation of said isomeric mixtures may be accomplished by standard techniques known in the art. For example, diastereomeric mixtures can be separated into the individual isomers by chromatographic processes or crystallization, and racemates can be separated into the respective enantiomers either by chromatographic processes on chiral phases or by optical resolution.

In addition, all possible tautomeric forms of the compounds described above are included according to the present disclosure.

Some examples of compounds of formula (I) for treating or preventing a cell proliferative disorder such as cancer are shown below and their preparation is described in examples 1-29:

3-(6,7-Dimethoxyquinazolin-4-ylamino)-5-tert-butylselenophene-2-carboxamide;
3-(6,7,8-Trimethoxyquinazolin-4-ylamino)-5-tert-butylselenophene-2-carboxamide;
3-(6-(3-Morpholinopropoxy)-7-methoxyquinazolin-4-ylamino)-5-tert-butylselenophene-2-carboxamide;
[5-(tert-Butyl)-2-nitroselenophene-3-yl][7-methoxy-6-(3-morpholinopropoxy)quinazolin-4-yl]amine;
3-(7-(3-Morpholinopropoxy)-6-methoxyquinazolin-4-ylamino)-5-tert-butylselenophene-2-carboxamide;
3-(6,7-Bis(2-methoxyethoxy)quinazolin-4-ylamino)-5-tert-butylselenophene-2-carboxamide;
3-(6-(3-Morpholinopropoxy)-7-methoxyquinazolin-4-ylamino)-5-phenyl-selenophene-2-carboxamide;
3-(6-Aminoquinazolin-4-ylamino)-5-tert-butylselenophene-2-carboxamide;
3-(6-(2-Chloroacetamido)quinazolin-4-ylamino)-5-tert-butylselenophene-2-carboxamide;
Methyl 4-(6-(3-morpholinopropoxy)-7-methoxyquinazolin-4-ylamino)-5-methyl-selenophene-2-carboxylate;
4-(6-(3-Morpholinopropoxy)-7-methoxyquinazolin-4-ylamino)-5-methylselenophene-2-carboxamide;
5-tert-Butyl-3-(pyridino[2,3-d]pyrimidin-4-ylamino)selenophene-2-carboxamide;
3-(5-Ethyl-6-methylthiopheno[2,3-d]pyrimidin-4-ylamino)-5-tert-butylselenophene-2-carboxamide;
3-(6-(Methylthio)thiopheno[3,2-d]pyrimidin-4-ylamino)-5-tert-butyl-selenophene-2-carboxamide;
3-(6-Phenylfuro[2,3-d]pyrimidin-4-ylamino)-5-tert-butylselenophene-2-carboxamide;

3-(6-tert-Butylfuro[2,3-d]pyrimidin-4-ylamino)-5-tert-butylselenophene-2-carboxamide;
Methyl 4-(5,6-dimethyl-7H-pyrrolo[2,3-d]pyrimidin-4-ylamino)-5-methylselenophene-2-carboxylate;
3-(6-tert-Butylselenopheno[3,2-d]pyrimidin-4-ylamino)-5-tert-butylselenophene-2-carboxamide;
3-(5-Ethyl-6-methylselenopheno[2,3-d]pyrimidin-4-ylamino)-5-tert-butylselenophene-2-carboxamide;
3-(2-(Methylthio)thiazolo[4,5-d]pyrimidin-7-ylamino)-5-tert-butylseleno-phene-2-carboxamide;
3-(N-(6,7-Dimethoxyquinazolin-4-yl)-N-methylamino)-5-tert-butylseleno-phene-2-carboxamide;
3-(N-(6-(3-Morpholinopropoxy)-7-methoxyquinazolin-4-yl)-N-methylamino)-5-tert-butylselenophene-2-carboxamide;
3-(N-(6-(3-Morpholinopropoxy)-7-methoxyquinazolin-4-yl)-N-(2-chloroethyl)amino)-5-tert-butylselenophene-2-carboxamide;
3-(6,7-Dimethoxy-2-methylquinazolin-4-ylamino)-5-tert-butylselenophene-2-carboxamide;
Methyl 4-(6,7-dimethoxy-2-methylquinazolin-4-ylamino)-5-methylselenophene-2-carboxylate;
3-(6-(3-Morpholinopropoxy)-7-methoxy-2-methylquinazolin-4-ylamino)-5-tert-butylselenophene-2-carboxamide;
(3-Ethynylphenyl)-5,6,7,8-tetrahydropyrimidino[5',6'-5,4]selenopheno[2,3-c]pyridin4-ylamine;
3-(2-(4-Chlorophenyl)-6,7-dimethoxyquinazolin-4-ylamino)-5-tert-butylselenophene-2-carboxamide;
3-(6,7-Dimethoxyquinazolin-4-yloxy)-5-tert-butylselenophene-2-carboxamide.

Synthesis of Selenophene Compounds of Formula (I)

The present disclosure also relates to a process for preparing the compounds of formula (I), wherein all the groups are as defined earlier.

The compounds of formula (I) may be synthesized by reacting a compound of formula II with 3-XH selenophenyl compound of formula III as shown in scheme A:

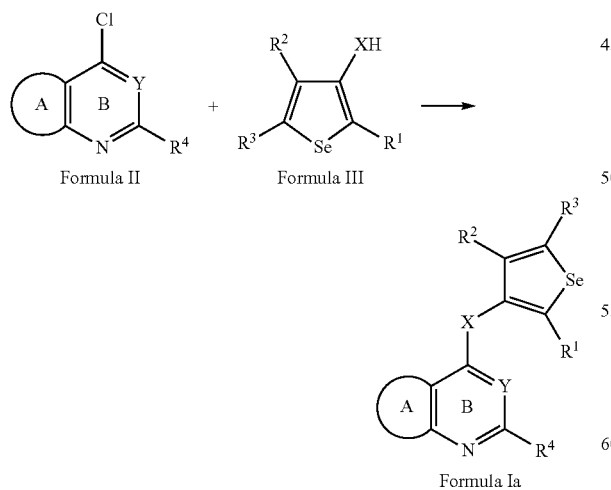

As shown in scheme A, a compound of formula II, wherein ring A is aromatic/heteroaromatic ring is reacted with 3-XH-selenophenyl compound of formula III in the presence of a solvent such as isopropyl alcohol, ethanol, dimethyl formamide and optionally in the presence of a base, to yield a compound of formula Ia. The base may be organic or inorganic, such as pyridine, triethyl amine, sodium hydroxide or potassium hydroxide.

The compounds of formula (I) may be synthesized by reacting a compound of formula II with 2-XHselenophenyl compound of formula IV as shown in scheme B:

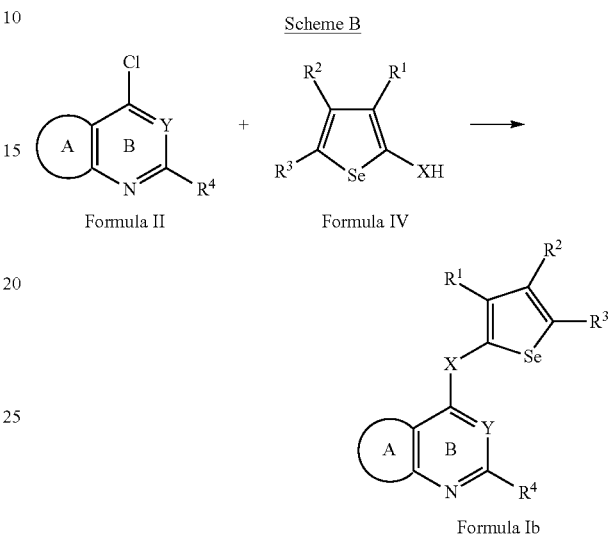

As shown in scheme B, a compound of formula II, is reacted with 2-XHselenophenyl compound of formula IV in the presence of a solvent such as isopropyl alcohol, ethanol, dimethyl formamide and optionally in presence of a base, to yield a compound of formula Ib. The base may be organic or inorganic, such as pyridine, triethyl amine, sodium hydroxide or potassium hydroxide.

The X in formula III and in formula IV is selected from NH or O.

Alternatively, the compounds of formula (I) in which X is NH; Y is N and $R^4$ is H can be made by reacting a compound of formula V with 3-aminoselenophenyl compound of formula III as shown in scheme C:

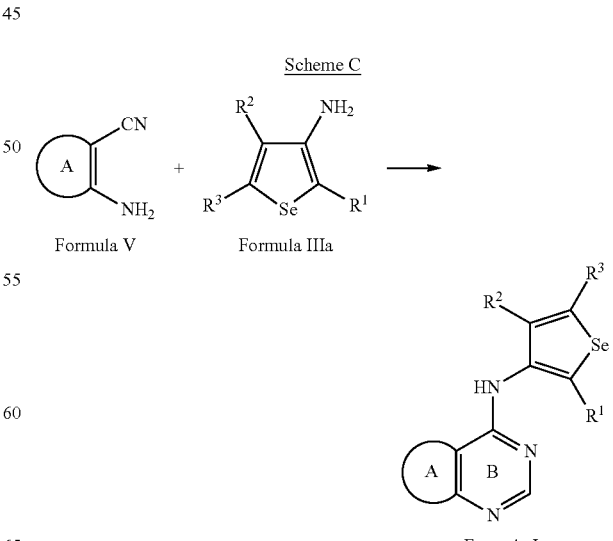

As an alternative to the procedure depicted in Scheme A, a compound of formula V, wherein ring A aromatic/heteroaromatic ring is reacted with dimethylformamide-dimethylacetal in the presence of a solvent, such as toluene, acetonitrile or acetic acid or a mixture thereof to yield [(dimethylamino)methylidene]amino-substituted compound, which is subsequently cyclized with 3-selenophenyl compound of formula IIIa in a solvent, such as toluene, acetonitrile, acetic acid or a mixture thereof to yield a compound of formula Ic as shown in scheme C. In addition, a compound of formula V, wherein ring A aromatic/heteroaromatic ring is reacted with triethyl orthoformate or trimethyl orthoformate in the presence of a solvent, such as toluene, acetonitrile or acetic acid or a mixture thereof, which is subsequently cyclized with 3-selenophenyl compound of formula IIIa in a solvent, such as toluene, acetonitrile, acetic acid or a mixture thereof to yield a compound of formula Ic.

Alternatively, the compounds of formula (I) in which X is NH; Y is N and $R^4$ is H can be made by reacting a compound of formula V with 2-aminoselenophenyl compound of formula IVa as shown in scheme D:

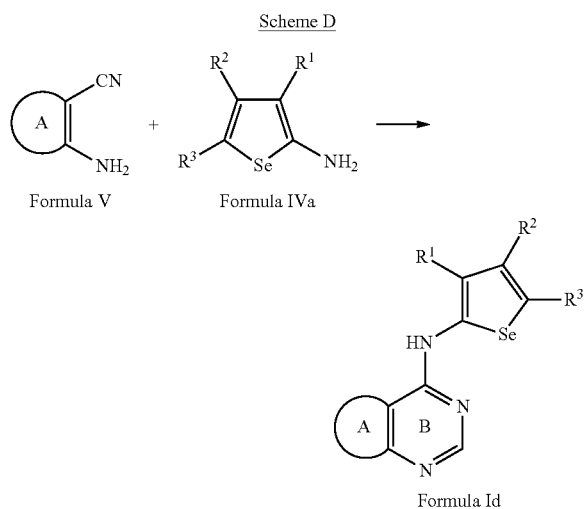

Formula V    Formula IVa

Formula Id

As an alternative to the procedure depicted in scheme B, a compound of formula V, wherein ring A is benzene (substituted 2-aminobenzonitrile) or any aromatic/heteroaromatic ring is reacted with dimethylformamide-dimethylacetal in the presence of a solvent such as toluene, acetonitrile or acetic acid or a mixture thereof to yield [(dimethylamino)methylidene]amino-substituted compound, which is subsequently cyclized with 2-selenophenyl compound (Aumann, K. M. et. al., Org. Biomol. Chem., 2007, 5, 1276-1281) of formula IVa in a solvent, such as toluene, acetonitrile, acetic acid or a mixture thereof to yield a compound of formula Id as shown in scheme D. In addition, a compound of formula V, is reacted with triethyl orthoformate or trimethyl orthoformate in the presence of a solvent such as toluene, acetonitrile or acetic acid or a mixture thereof, which is subsequently cyclized with 2-selenophenyl compound of formula IVa in a solvent, such as toluene, acetonitrile, acetic acid or a mixture thereof to yield a compound of formula Id.

Y in formula II is N or $CR^5$ and ring A in formula II or in formula V, is selected from benzene, pyridine, pyrazine, pyrimidine, pyridazine, thiophene, furan, pyrrole, selenophene, oxazole, isoxazole, imidazole, pyrazole, thiazole, and isothiazole.

The synthetic process of some of the compounds of formula (I) is demonstrated as shown below.

Synthesis of 4-(selenophen-3-ylamino)quinazolines

The synthesis of selenophene compounds of formula (I), more specifically the synthesis of 4-(selenophen-3-ylamino)quinazolines is achieved by the steps shown in scheme E.

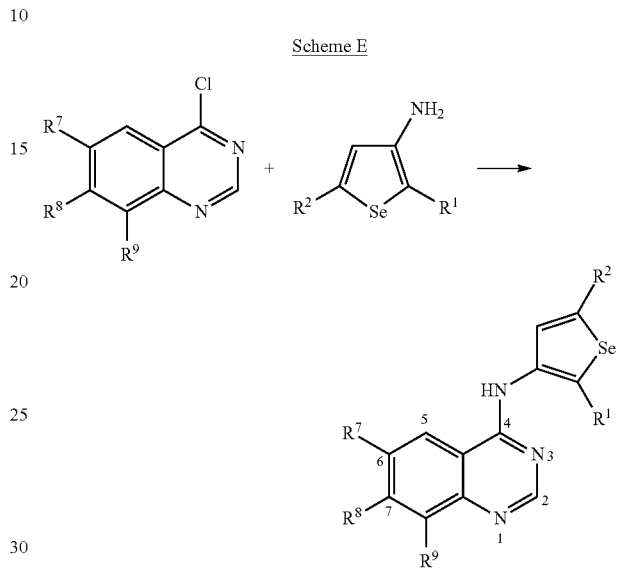

As shown in scheme E, 4-chloroquinazolines (Gazit, A. et. al., Bioorg. Med. Chem., 1996, 4, 1203-1207; Furuta, T. et al., J. Med. Chem., 2006, 49, 2186-2192; Liu, G. et. al., Bioorg. Med. Chem., 2007, 15, 6608-6617; Wang, J.-Q. et. al., Bioorg. Med. Chem. Lett., 2006, 16, 4102-4106; Ple, P. A. et. al., J. Med. Chem., 2004, 47, 871-887; Marzaro, G. et. al., Tetrahedron, 2010, 66, 962-968; Knesl, P. et. al., Molecules, 2006, 11, 286-297; Shaul, M. et. al., Bioorg. Med. Chem., 2004, 12, 3421-3429; Fernandes, C. et. al., Bioorg. Med. Chem., 2007, 15, 3974-3980) are reacted with 3-aminoselenophenes (Hesse, S. et. al., Synthesis, 2009, 1204-1208; Thomae, D. et al., Synthesis, 2008, 1600-1606) in a protic solvent such as isopropyl alcohol, ethanol, dimethylformamide and optionally in presence of a base, to yield 4-selenophen-3-ylaminoquinazolines. The base may be organic or inorganic, such as pyridine, triethyl amine, sodium hydroxide etc. Using this process the following 4-selenophen-3-ylaminoquinazolines were synthesized.

| Compd. | Chemical structure |
|---|---|
| 1 | 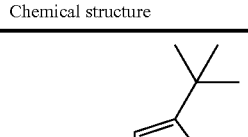 |

| Compd. | Chemical structure |
|---|---|
| 2 | 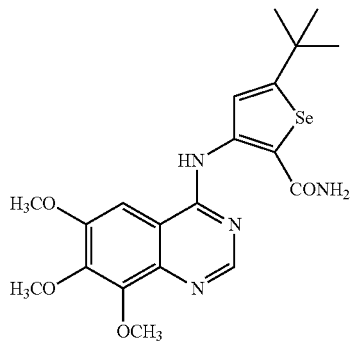 [SMILES: COc1cc2c(Nc3cc(C(C)(C)C)[se]c3C(N)=O)ncnc2c(OC)c1OC] |
| 3 | 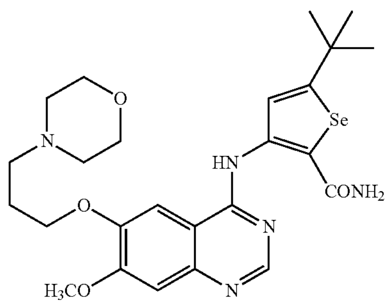 [SMILES: COc1cc2ncnc(Nc3cc(C(C)(C)C)[se]c3C(N)=O)c2cc1OCCCN1CCOCC1] |
| 4 | 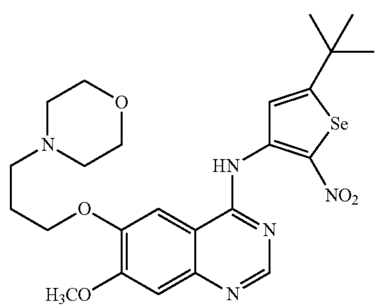 [SMILES: COc1cc2ncnc(Nc3cc(C(C)(C)C)[se]c3[N+](=O)[O-])c2cc1OCCCN1CCOCC1] |
| 5 | 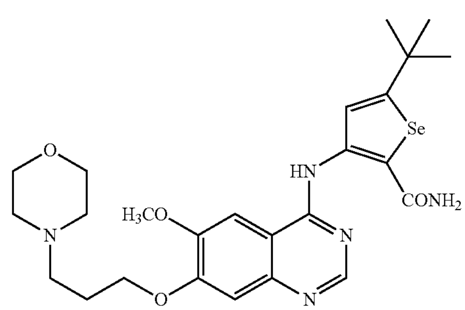 [SMILES: COc1cc2c(Nc3cc(C(C)(C)C)[se]c3C(N)=O)ncnc2cc1OCCCN1CCOCC1] |
| 6 | 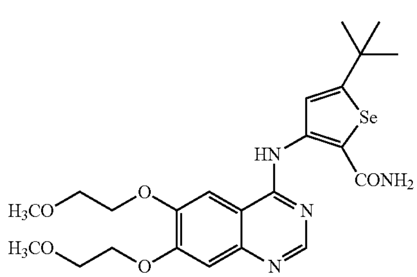 [SMILES: COCCOc1cc2ncnc(Nc3cc(C(C)(C)C)[se]c3C(N)=O)c2cc1OCCOC] |

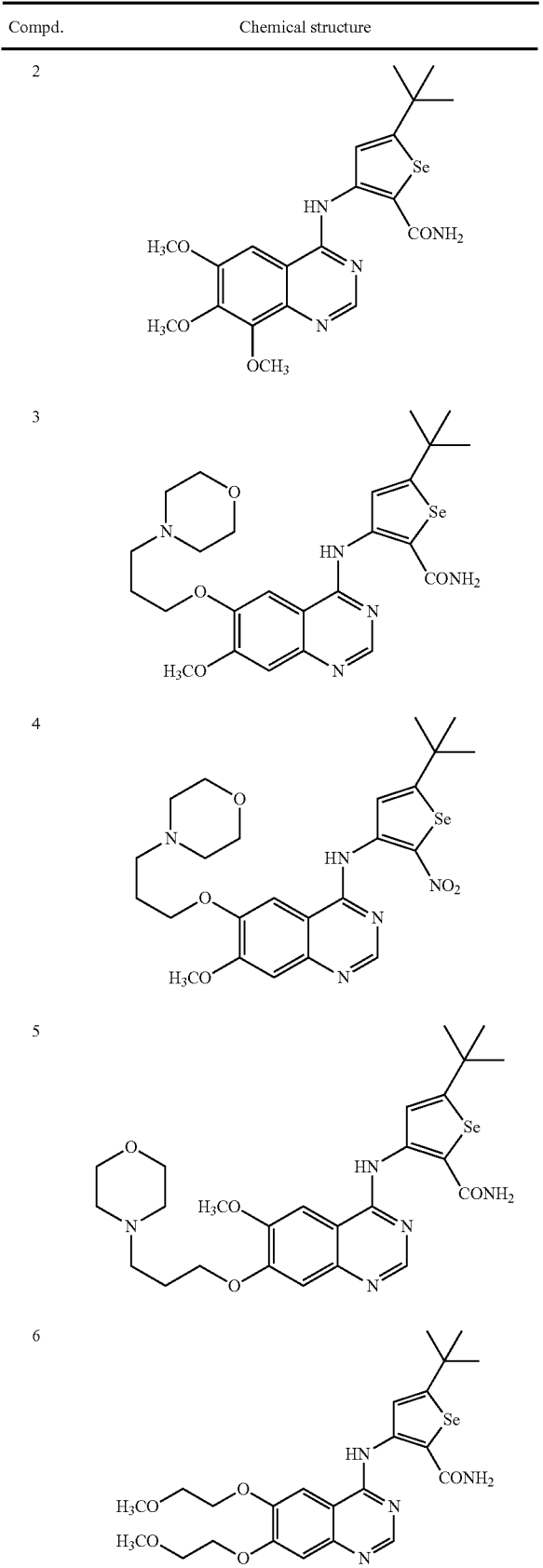

| Compd. | Chemical structure |
|---|---|
| 7 | 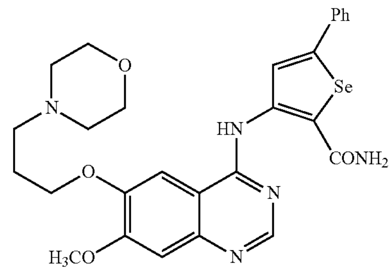 [SMILES: COc1cc2ncnc(Nc3cc(-c4ccccc4)[se]c3C(N)=O)c2cc1OCCCN1CCOCC1] |
| 8 | 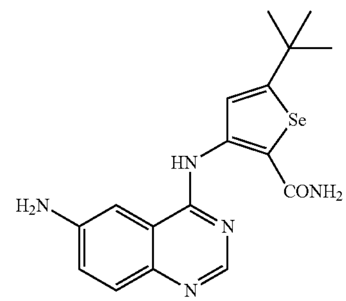 [SMILES: CC(C)(C)c1cc(Nc2ncnc3ccc(N)cc23)c(C(N)=O)[se]1] |
| 9 | 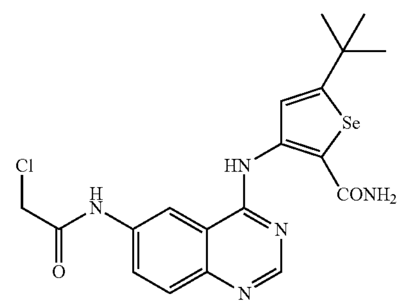 [SMILES: CC(C)(C)c1cc(Nc2ncnc3ccc(NC(=O)CCl)cc23)c(C(N)=O)[se]1] |

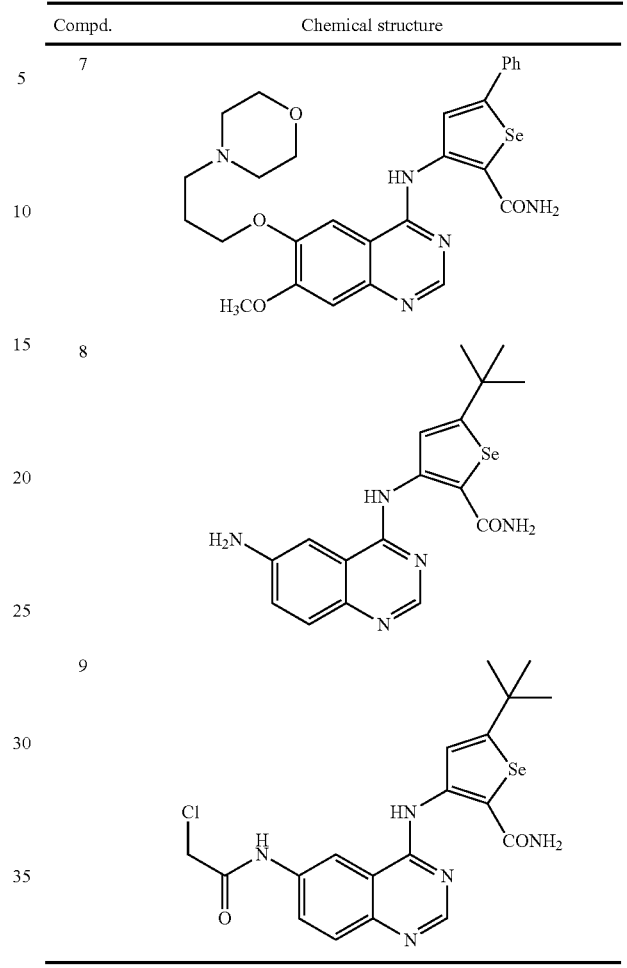

Another method for the synthesis of selenophene compounds of formula (I), more specifically the synthesis of 4-selenophen-3-ylaminoquinazolines is achieved by the steps shown in scheme F.

Scheme F

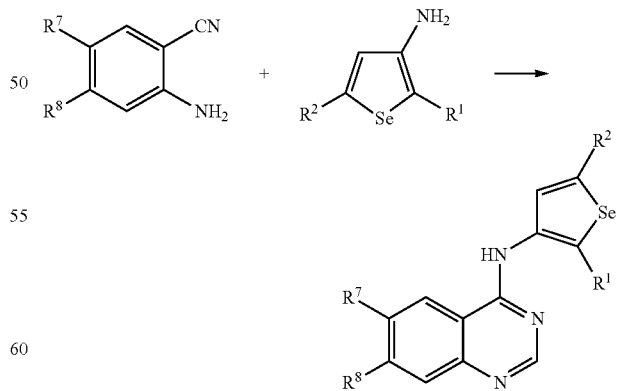

As shown in scheme F, 2-aminobenzonitriles are reacted with N,N-dimethylformamide-dimethylacetal or triethyl orthoformate, followed by treatment with 3-aminoselenophenes in toluene/acetic acid to yield 4-selenophen-3- ylaminoquinazolines. Using this process the following 4-selenophenylaminoquinazolines were synthesized.

| Compd. | Chemical structure |
|--------|--------------------|
| 10 | 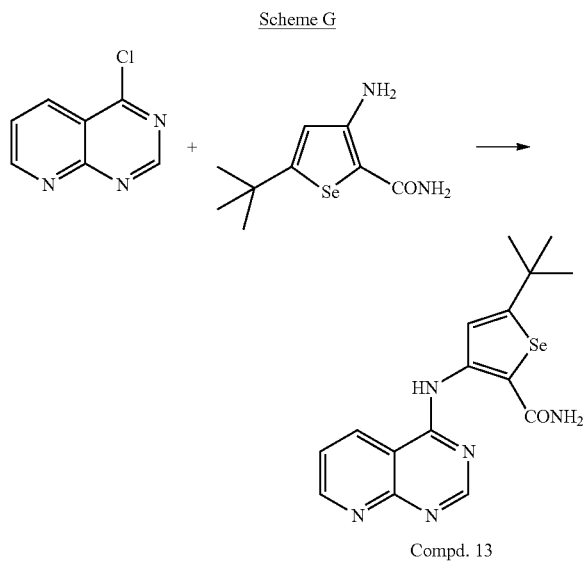 |
| 11 | 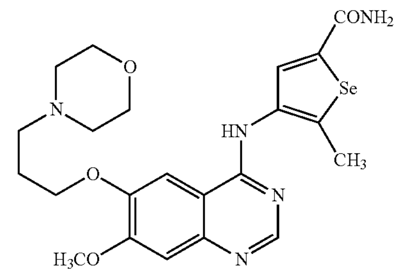 [SMILES: COc1cc2ncnc(Nc3cc(C(N)=O)[se]c3C)c2cc1OCCCN1CCOCC1] |

Synthesis of 4-(selenophen-3-ylaminopyrido)pyrimidines

The synthesis of selenophene compounds of formula (I), more specifically the synthesis of 4-(selenophen-3-ylaminopyrido)pyrimidine is achieved by the steps shown in scheme G.

Scheme G

Compd. 13

As shown in scheme G, 4-chloropyrido[2,3-d]pyrimidine (Robins, R. K. et. al., *J. Am. Chem. Soc.*, 1955, 77, 2256-2260) is reacted with 5-tert-butyl-3-aminoselenophene-2-carboxamide in a protic solvent such as isopropyl alcohol to yield 5-(tert-butyl)-3-(pyridino[3,2-e]pyrimidin-4-ylamino) selenophene-2-carboxamide.

Synthesis of 4-(selenophen-3-ylaminothiopheno)pyrimidines

The synthesis of selenophene compounds of formula (I), more specifically the synthesis of 4-(selenophen-3-ylaminothiopheno)pyrimidine is achieved by the steps shown in scheme H.

Scheme H

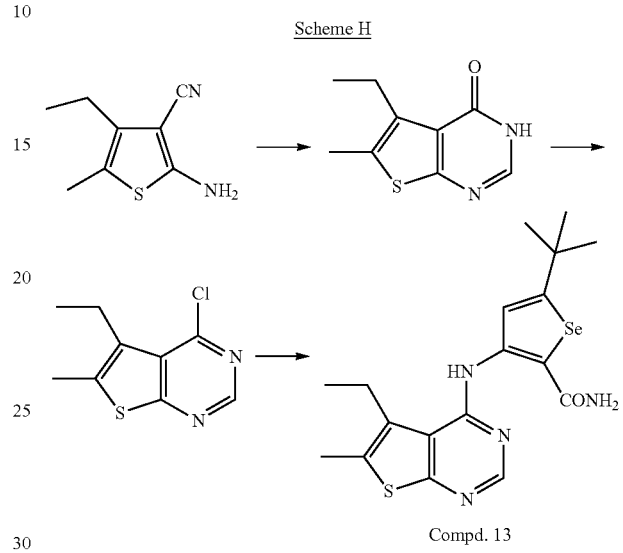

Compd. 13

As shown in scheme H, cyclisation of 2-amino-4-ethyl-5-methylthiophene-3-carbonitrile using formic acid/sulfuric acid and further treatment with thionyl chloride gave 4-chloro-5-ethyl-6-methylthiopheno[2,3-d]pyrimidine (Horiuchi, T. et. al., *Bioorg. Med. Chem. Lett.,* 2009, 19, 305-308) in good yield. Treatment of this 4-chlorocompound with 3-amino-5-tert-butylselenophene-2-carboxamide in the presence of DMF/NaOH gave 5-(tert-butyl)-3-[5-ethyl-6-methylthiopheno[3,2-e]pyrimidin-4-yl)amino]-selenophene-2-carboxamide.

The synthesis of selenophene compounds of formula (I), more specifically the synthesis of 4-(selenophen-3-ylaminothiopheno)pyrimidine is achieved by the steps shown in scheme I.

Scheme I

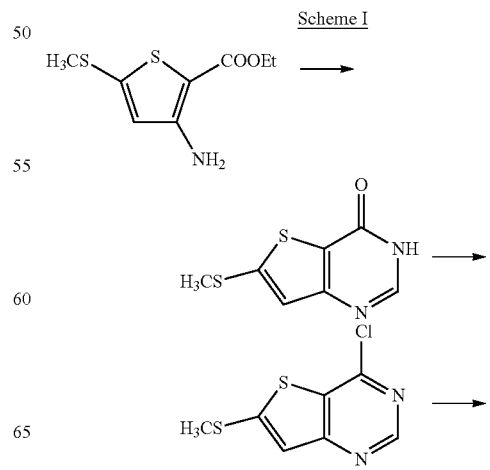

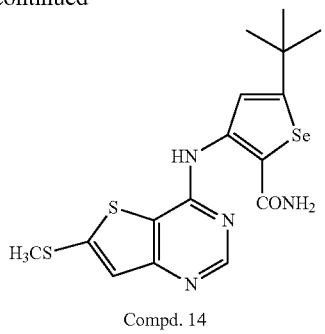

Compd. 14

As shown in scheme I, cyclisation of ethyl 3-amino-5-(methylthio)-thiophene-2-carboxylate using formamide and further treatment with phosphorous oxychloride gave 4-chloro-6-(methylthio)thieno[3,2-d]pyrimidine in good yield. Treatment of this 4-chlorocompound with 3-amino-5-tert-butylselenophene-2-carboxamide in the presence of DMF/NaOH gave 3-(6-(methylthio)thieno[3,2-d]pyrimidin-4-ylamino)-5-tert-butylselenophene-2-carboxamide.

Synthesis of 4-(selenophen-3-ylaminofurano)pyrimidines

The synthesis of selenophene compounds of formula (I), more specifically the synthesis of 4-(selenophen-3-ylaminofurano)pyrimidine is achieved by the steps shown in scheme J.

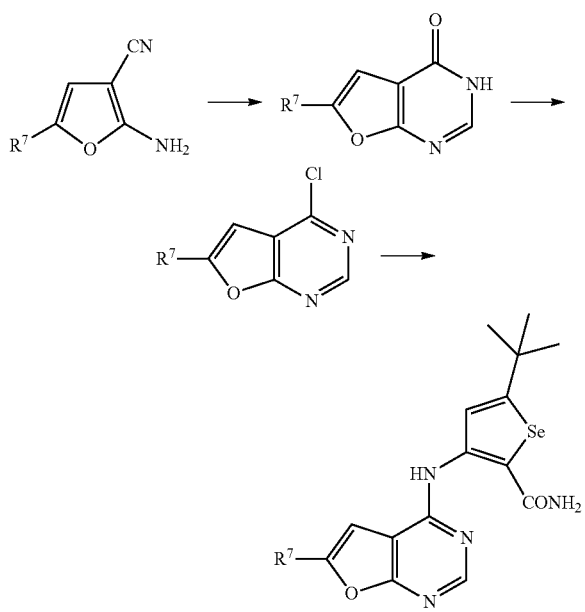

Scheme J

As shown in scheme J, cyclisation of 2-amino-5-substituted-furan-3-carbonitriles (Foley, L. H. *Tetrahedron Lett.*, 1994, 35, 5989-5992; Matsuda, T. et. al., *Chem. Pharm. Bull.*, 1985, 33, 937-943) using formic acid/acetic anhydride and further treatment with phosphorous oxychloride gave 4-chloro-6-substitutedfuro[2,3-d]pyrimidines in good yields. Treatment of these 4-chlorocompounds with 3-amino-5-tert-butylselenophene-2-carboxamide in the presence of DMF/ NaOH gave 4-selenophen-3-ylaminofuranopyrimidines. Using this process the following 4-selenophen-3-ylaminofuranopyrimidines were synthesized.

| Compd. | Chemical structure |
|---|---|
| 15 | 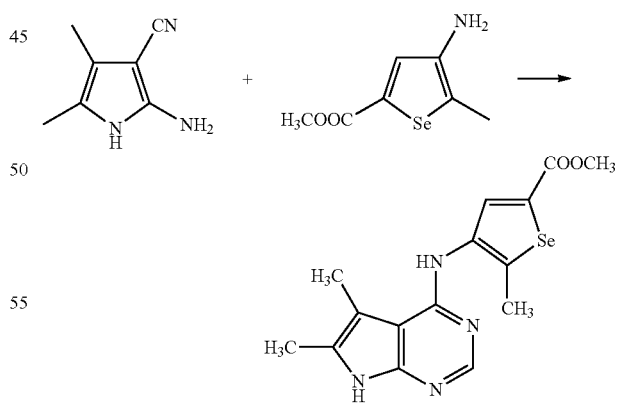 |
| 16 | 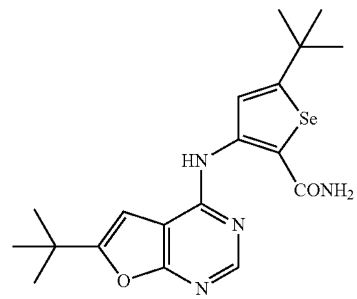 [SMILES: CC(C)(C)c1cc2c(Nc3cc(C(C)(C)C)[se]c3C(N)=O)ncnc2o1] |

Synthesis of 4-(selenophen-3-ylaminopyrrolo)pyrimidines

The synthesis of selenophene compounds of formula (I), more specifically the synthesis of 4-(selenophen-3-ylaminopyrrolo)pyrimidine is achieved by the steps shown in scheme K.

Scheme K

Compd. 17

As shown in scheme K, 2-amino-4,5-dimethyl-1H-pyrrole-3-carbonitrile (Fischer, R. W. et. al., *Org. Proc. Res. Dev.*, 2001, 5, 581-586) is reacted with N,N-dimethylformamide-dimethylacetal in the presence of toluene/acetic acid, followed by methyl 4-amino-5-methylselenophene-2-carboxylate in acetic acid to yield methyl 4-(5,6-dimethyl-7H-pyrrolo[2,3-d]pyrimidin-4-ylamino)-5-methylselenophene-2-carboxylate.

Synthesis of
4-(selenophen-3-ylaminoselenopheno)pyrimidines

The synthesis of selenophene compounds of formula (I), more specifically the synthesis of 4-(selenophen-3-ylaminoselenopheno)pyrimidine is achieved by the steps shown in scheme L.

Scheme L

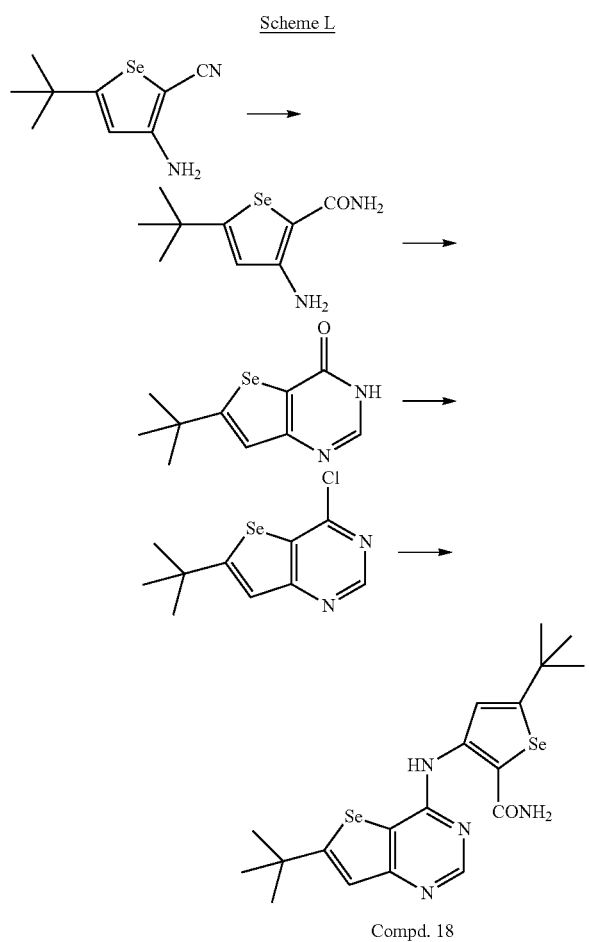

Compd. 18

As shown in scheme L, 3-amino-5-(tert-butyl)selenophene-2-carbonitrile is treated with 10% aqueous NaOH solution/ethanol to give 3-amino-5-(tert-butyl)selenophene-2-carboxamide. Which is cyclised using formic acid/sulfuric acid to give 6-(tert-butyl)-3-hydroselenopheno[3,2-d]pyrimidin-4-one and further treatment with thionyl chloride gave 6-(tert-butyl)-4-chloroselenopheno[3,2-d]pyrimidine (Hesse, S. et. al., *Synthesis*, 2009, 1204-1208) in good yield. Treatment of this 4-chlorocompound with 3-amino-5-tert-butylselenophene-2-carboxamide in the presence of DMF/NaOH gave 5-(tert-butyl)-3-{[6-(tert-butyl)selenopheno[2,3-e]pyrimidin-4-yl]amino}selenophene-2-carboxamide.

The synthesis of selenophene compounds of formula (I), more specifically the synthesis of 4-(selenophen-3-ylaminoselenopheno)pyrimidine is achieved by the steps shown in scheme M.

Scheme M

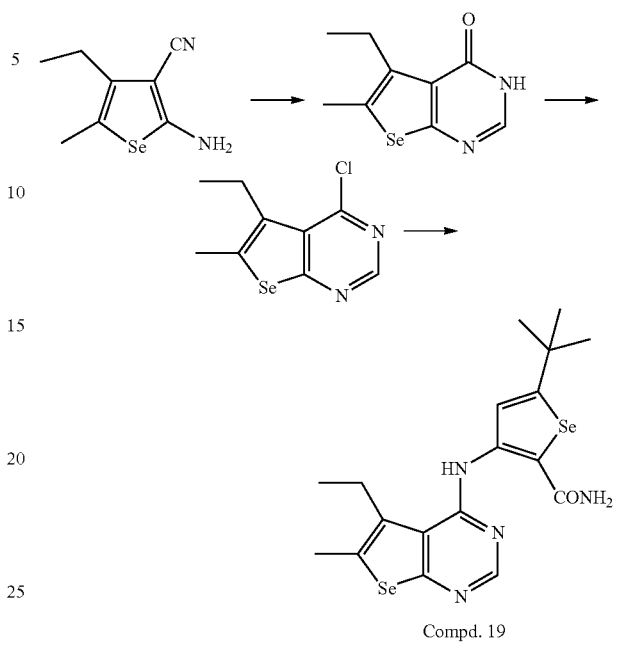

Compd. 19

As shown in scheme M, cyclisation of 2-amino-4-ethyl-5-methylselenophene-3-carbonitrile using formic acid/sulfuric acid and further treatment with phosphorous oxychloride gave 4-chloro-5-ethyl-6-methylselenopheno[2,3-d]pyrimidine in good yield. Treatment of this 4-chlorocompound with 3-amino-5-tert-butylselenophene-2-carboxamide in the presence of DMF/NaOH gave 3-(5-ethyl-6-methylselenopheno[2,3-d]pyrimidin-4-ylamino)-5-tert-butylselenophene-2-carboxamide.

Synthesis of
4-(selenophen-3-ylaminothiazolo)pyrimidines

The synthesis of selenophene compounds of formula (I), more specifically the synthesis of 4-(selenophen-3-ylaminothiazolo)pyrimidine is achieved by the steps shown in scheme N.

Scheme N

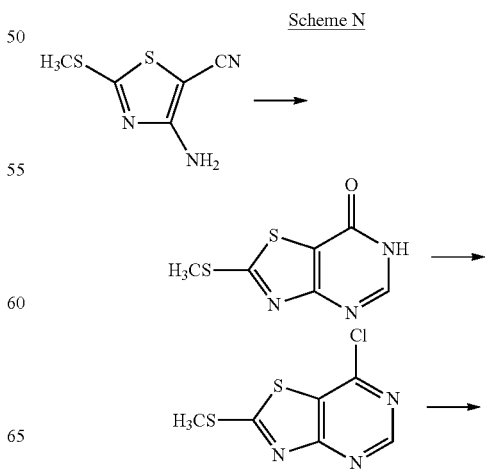

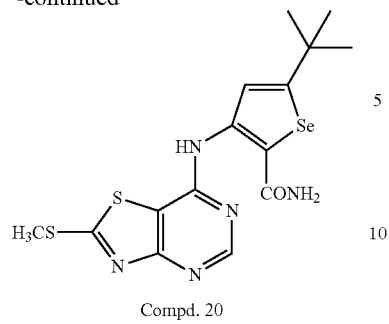

Compd. 20

As shown in scheme N, cyclisation of 4-amino-2-(methylthio)thiazole-5-carbonitrile (Thomae, D. et. al., *Tetrahedron,* 2008, 64, 9309-9314) using formic acid/sulfuric acid and further treatment with phosphorous oxychloride gave 7-chloro-2-(methylthio)thiazolo[4,5-d]pyrimidine (Lin, R. et. al., *Bioorg. Med. Chem. Lett.,* 2009, 19, 2333-2337) in good yield. Treatment of this chlorocompound with 3-amino-5-tert-butylselenophene-2-carboxamide in the presence of DMF/NaOH gave 3-(2-(methylthio)thiazolo[4,5-d]pyrimidin-7-ylamino)-5-tert-butylselenophene-2-carboxamide.

Synthesis of N-substituted compounds

The synthesis of selenophene compounds of formula (I), more specifically the synthesis of N-substituted analogs are achieved by the steps shown in scheme O.

Scheme O

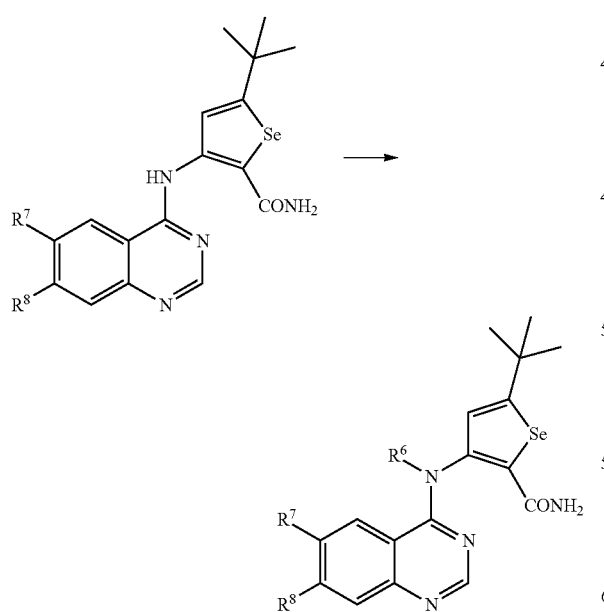

As shown in scheme O, treatment of NH compound with iodomethane or dimethyl sulfate or 1-bromo-2-chloroethane in presence of a base provide the N-substituted analogs. Using this process the following compounds were synthesized.

| Compd. | Chemical structure |
|---|---|
| 21 | 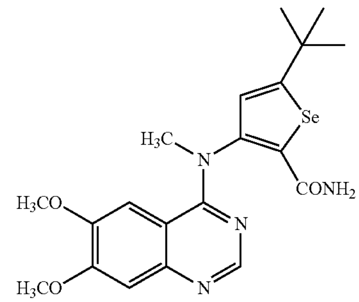 [SMILES: COc1cc2ncnc(N(C)c3cc(C(C)(C)C)[se]c3C(N)=O)c2cc1OC] |
| 22 | 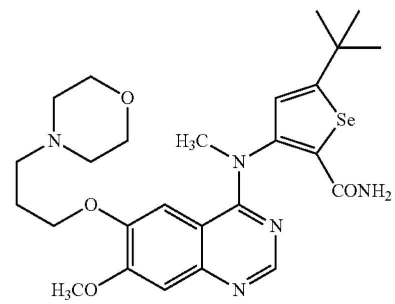 [SMILES: COc1cc2ncnc(N(C)c3cc(C(C)(C)C)[se]c3C(N)=O)c2cc1OCCCN1CCOCC1] |
| 23 | 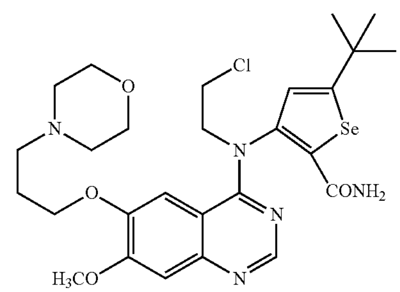 [SMILES: COc1cc2ncnc(N(CCCl)c3cc(C(C)(C)C)[se]c3C(N)=O)c2cc1OCCCN1CCOCC1] |

Synthesis of 2-substituted compounds

The synthesis of selenophene compounds of formula (I), more specifically the synthesis of 2-substituted analogs are achieved by the steps shown in scheme P.

Scheme P

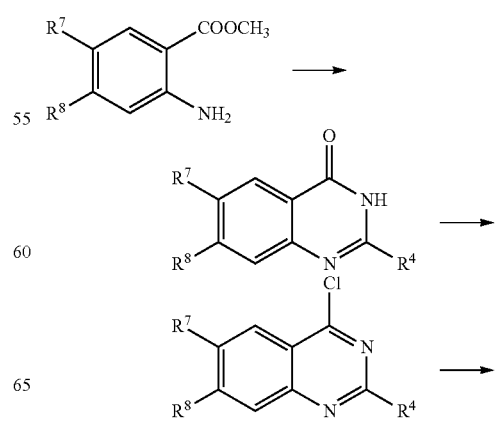

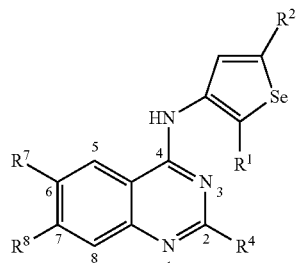

As shown in scheme P, substituted methyl 2-aminobenzoate is reacted with acetonitirle or chloroacetonitrile in presence of HCl to yield cyclised product (Zhang, X. et. al., *Green Chem.,* 2009, 11, 1881-1888; Walker, G. *J. Am. Chem. Soc.,* 1955, 77, 6698-6699; Li, H.-Z. et. al., *Molecules,* 2010, 15, 9473-9485) which is further treated with either phosphorous oxychloride or thionyl chloride to give 4-chlorocompound. 4-Chlorocompound is reacted with 3-aminoselenophene compound in the presence of DMF/NaOH to give 2-substituted analogs. Using this process, the following compounds were synthesized.

The synthesis of selenophene compounds of formula (I), more specifically the synthesis of 2-substituted analogs is achieved by the steps shown in scheme Q.

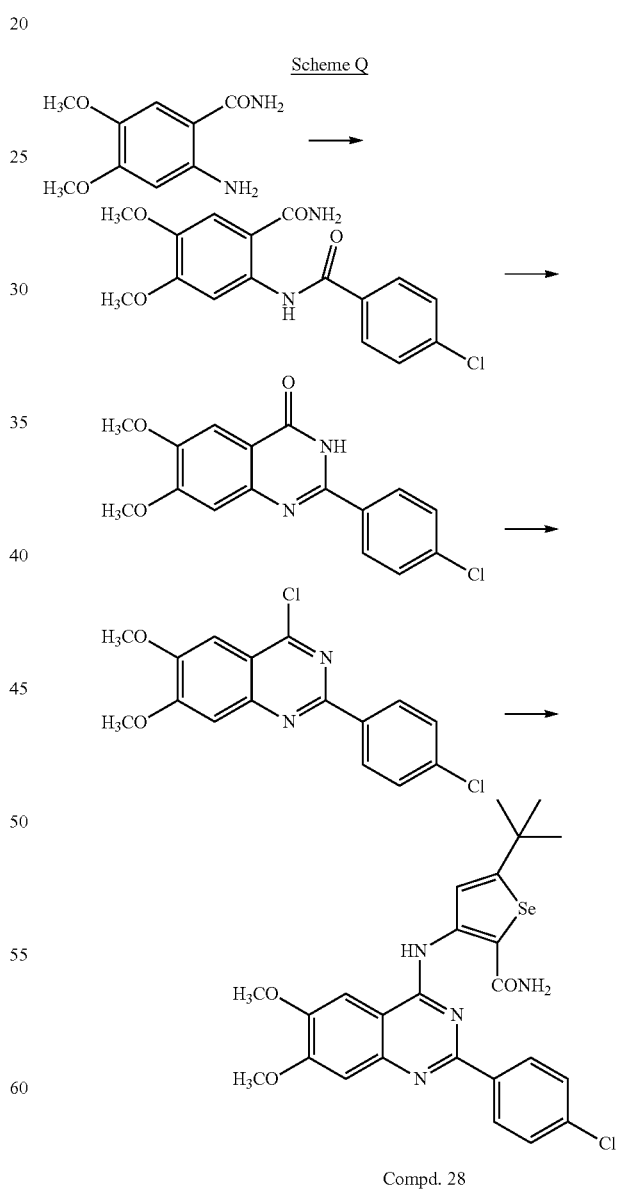

As shown in scheme Q, 2-amino-4,5-dimethoxybenzamide is reacted with 4-chlorobenzoyl chloride in presence of triethyl amine and THF to give 2-((4-chlorophenyl)carbonylamino)-4,5-dimethoxybenzamide. Which is cyclised using NaOH and then treated with thionyl chloride to give 4-chloro-2-(4-chlorophenyl)-6,7-dimethoxyquinazoline (McKee, R. L. et. al., *J. Am. Chem. Soc.*, 1946, 68, 1902-1903). The 4-chlorocompound is treated with 5-(tert-butyl)selenophene-2-carboxamide in the presence of NaOH/DMF to give 3-(2-(4-chlorophenyl)-6,7-dimethoxyquinazolin-4-ylamino)-5-tert-butylselenophene-2-carboxamide.

Synthesis of ether (X=O) Analogs

The synthesis of selenophene compounds of formula (I), more specifically the synthesis of ether analogs is achieved by the steps shown in scheme R.

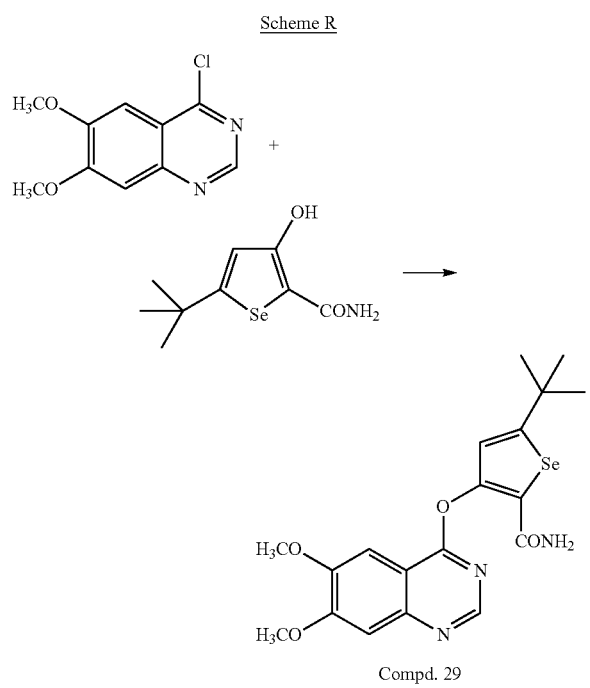

Compd. 29

As shown in scheme R, 4-chloro-6,7-dimethoxyquinazoline is reacted with 5-tert-butyl-3-hydroxyselenophene-2-carboxamide in presence of NaOH and DMF to give 3-(6,7-dimethoxyquinazolin-4-yloxy)-5-tert-butylselenophene-2-carboxamide. The 5-tert-butyl-3-hydroxyselenophene-2-carboxamide is prepared in five steps from pinacolone and is described in examples.

Synthesis of Aminoselenophenes

The synthesis of aminoselenophenes of formula (III), more specifically 3-amino-5-tert-butylselenophene-2-carboxamide and 3-amino-5-phenylselenophene-2-carboxamide is achieved by the steps shown in scheme S.

Scheme S

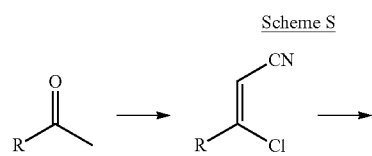

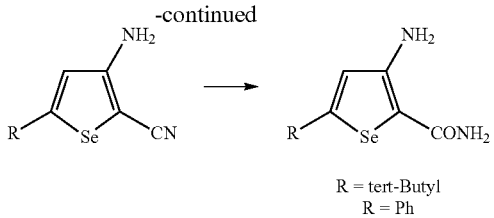

R = tert-Butyl
R = Ph

The 3-chloro-3-substituted prop-2-enenitrile is prepared starting from the corresponding ketone with DMF-phosphorous oxychloride followed by hydroxylamine hydrochloride.

The obtained products are reacted with sodium selenide, chloroacetonitrile in the presence of a base to provide 5-substituted 3-aminoselenophene-2-carbonitriles in good yields. Finally, nitrile group is hydrolysed using aqueous sodium hydroxide solution to provide 3-amino-5-tert-butylselenophene-2-carboxamide and 3-amino-5-phenylselenophene-2-carboxamide.

The synthesis of aminoselenophenes of formula (III), more specifically 3-amino-5-tert-butyl-2-nitroselenophene is achieved by the steps shown in scheme T.

Scheme T

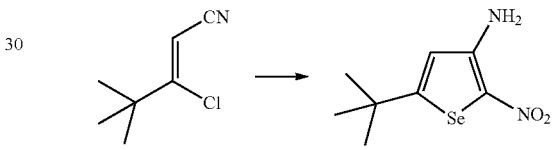

The 3-chloro-3-tert-butylprop-2-enenitrile is reacted with sodium selenide, bromonitromethane in the presence of a base to provide 3-amino-5-tert-butyl-2-nitroselenophene.

The synthesis of aminoselenophenes of formula (III), more specifically methyl 4-amino-5-methylselenophene-2-carboxylate is achieved by the steps shown in scheme U.

Scheme U

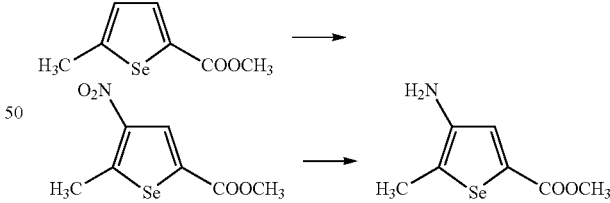

Nitration of methyl 5-methylselenophene-2-carboxylate (Tsuboni, S. et. al., *Tetrahedron Lett.*, 1986, 27, 2643-2644) provided methyl 5-methyl-4-nitroselenophene-2-carboxylate. The nitro functionality is reduced to amines using suitable reducing agents, for example, iron powder or any other nitro reducing agents in good yield.

Throughout this document, for the sake of simplicity, the use of singular language is given preference over plural language, but is generally meant to include the plural language if not otherwise stated. E.g., the expression "A method of treating a disease in a patient, comprising administering to a patient an effective amount of a compound of formula (I)" is meant to include the simultaneous treatment of more than one disease as well as the administration of more than one compound of formula (I).

Compositions

Various embodiments disclosed herein provide pharmaceutical compositions comprising a compound of formula (I) or a pharmaceutically acceptable salt or solvates or hydrates or stereoisomers thereof in combination with a pharmaceutically acceptable excipient(s) or carrier(s) or diluent(s);

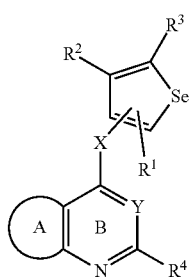

Formula (I)

wherein all the groups are as defined earlier.

The pharmaceutical compositions comprising a compound of formula (I) or a pharmaceutically acceptable salt or solvates or hydrate or stereoisomers thereof in combination with a pharmaceutically acceptable excipient(s) or carrier(s) or diluent(s); and the concentration of said compound of formula (I) is in the range of 0.01% to 99%.

The pharmaceutical compositions comprising a compound of formula (I) or a pharmaceutically acceptable salt or solvates or hydrates or stereoisomers thereof in combination with a pharmaceutically acceptable excipient(s) or carrier(s) or diluent(s); the said carrier or diluent or excipient is selected from the group consisting of glucose, fructose, sucrose, maltose, yellow dextrin, white dextrin, aerosol, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors and preservatives, distilled water, saline, aqueous glucose solution, alcohol (e.g. ethanol), propylene glycol and polyethylene glycol, various animal and vegetable oils, white soft paraffin, paraffin and wax.

When the compounds of the present disclosure are administered as pharmaceuticals, to humans and animals, they can be given per se or as a pharmaceutical composition containing, for example, 0.01 to 99.5% of a compound of formula (I) in combination with a pharmaceutically acceptable carrier or diluent.

In still another aspect, the disclosure provides a process for preparing a pharmaceutical composition. The process involves the step of combining at least one compound of formula (I) as defined above with at least one pharmaceutically acceptable carrier or diluent, and bringing the resulting combination into a suitable administration form.

In another aspect, the pharmaceutical compositions of the present disclosure may be in any form which allows for the composition to be administered to a subject. For example, the composition may be in the form of a solid, liquid or gas (aerosol). Typical routes of administration include, without limitation, topical, parenteral, sublingual, intraperitoneal (IP), intravenous (IV), oral (PO), intramuscular (IM), intracutaneous (IC), intradermal (ID), intrauterine and intrarectal. The term parenteral as used herein includes subcutaneous injections, intravenous, intramuscular, intrasternal injection or infusion techniques. Pharmaceutical compositions of the disclosure are formulated so as to allow the active ingredients contained therein to be bioavailable upon administration of the composition to a subject. Compositions that will be administered take the form of one or more dosage units, for example, a tablet may be a single dosage unit, and a container of formula (I) compound in topical form may hold a plurality of dosage units and also in the form of nanoparticles of different sizes in an emulsion to a warm blooded animal, in need thereof.

It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

Various embodiments disclosed herein provide the pharmaceutical compositions comprising at least one compound of formula (I) or a pharmaceutically acceptable salt or solvates or hydrates or stereoisomers thereof and at least one selected from pharmaceutically acceptable excipient, pharmaceutically acceptable diluent, and pharmaceutically acceptable carrier, and optionally further comprising attest one anti-tumor agent.

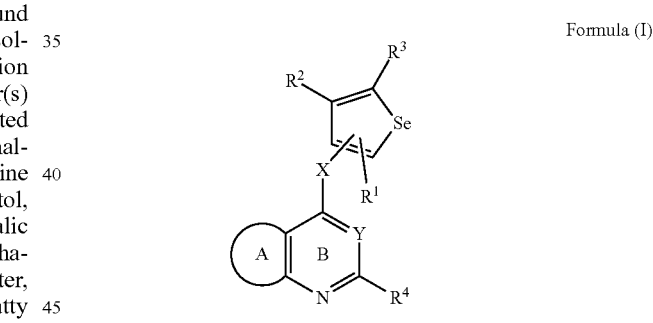

Formula (I)

wherein all the groups are as defined earlier.

The anti-tumor agent is selected from Alkylating agents, Anti-metabolites, Hormonal therapy agents, Cytotoxic topoisomerase inhibiting agents, Anti-angiogenic compounds, Antibodies, VEGF inhibitors, EGFR (HERB inhibitors, HER2 inhibitors, CDK inhibitors, Proteasome inhibitors, Serine/threonine kinase (Raf inhibitors), Tyrosine kinase inhibitors, Androgen receptor antagonists and Aromatase inhibitors. In this regard, the following is a non-limiting list of examples of secondary agents that may be used in combination with the compounds of the present disclosure:

Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, mitolactol, cisplatin, carboplatin, eptaplatin, lobaplatin, nedaplatin, oxaliplatin, and satraplatin.

Anti-metabolites include, but are not limited to, methotrexate, 6-mercaptopurineriboside, mercaptopurine, 5-fluorouracil, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosf[iota]te, disodium premetrexed, pentostatin, pelitrexol, raltitrexed, triapine, trimetrexate, vidarabine, vincristine, and vinorelbine;

Hormonal therapy agents include, but are not limited to, exemestane, Lupron, anastrozole, doxercalciferol, fadrozole, formestane, abiraterone acetate, finasteride, epristeride, tamoxifen citrate, fulvestrant, Trelstar, toremifene, raloxifene, lasofoxifene, letrozole, sagopilone, ixabepilone, epothilone B, vinblastine, vinflunine, docetaxel, and paclitaxel;

Cytotoxic topoisomerase inhibiting agents include, but are not limited to, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide;

Anti-angiogenic compounds include, but are not limited to, acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin.

Antibodies include, but are not limited to, trastuzumab, cetuximab, bevacizumab, rituximab, ticilimumab, ipilimumab, lumiliximab, catumaxomab, atacicept, oregovomab, and alemtuzumab.

VEGF inhibitor is selected from sorafenib, DAST, bevacizumab, sunitinib, recentin, axitinib, aflibercept, telatinib, brivanib alaninate, vatalanib, pazopanib, and ranibizumab.

EGFR (HERD inhibitor is selected from cetuximab, panitumumab, vectibix, gefitinib, erlotinib, and Zactima;

HER2 inhibitor is selected from lapatinib, tratuzumab, and pertuzumab; CDK inhibitor is selected from roscovitine and flavopiridol;

Proteasome inhibitor is selected from bortezomib and carfilzomib;

Serine/threonine kinase inhibitors including MEK inhibitors and Raf inhibitors such as sorafenib;

Tyrosine kinase inhibitor is selected from dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab and pertuzumab.

Androgen receptor antagonist is selected from nandrolone decanoate, fluoxymesterone, Android, Prostaid, andromustine, bicalutamide, flutamide, apocyproterone, apoflutamide, chlormadinone acetate, Androcur, Tabi, cyproterone acetate, and nilutamide.

Aromatase inhibitor is selected from anastrozole, letrozole, testolactone, exemestane, aminoglutethimide, and formestane.

Other anti-cancer agents including, e.g., alitretinoin, ampligen, atrasentan bexarotene, borte-zomib, bosentan, calcitriol, exisulind, fotemustine, ibandronic acid, miltefosine, mitoxantrone, 1-asparaginase, procarbazine, dacarbazine, hydroxycarbamide, pegaspargase, pentostatin, tazaroten, velcade, gallium nitrate, canfosfamide, darinaparsin, and tretinoin. In a preferred embodiment, the compounds of the present disclosure may be used in combination with chemotherapy (i.e. cytotoxic agents), anti-hormones and/or targeted therapies such as other kinase inhibitors, mTOR inhibitors and angiogenesis inhibitors.

The compounds of the present disclosure may also be employed in cancer treatment in conjunction with radiation therapy and/or surgical intervention. Furthermore, the compounds of formula (I) may be utilized, as such or in compositions, in research and diagnostics, or as analytical reference standards, and the like, which are well known in the art.

In still another aspect, the disclosure provides use of a compound of formula (I) as defined above for manufacturing a pharmaceutical composition for the treatment or prevention of a cell proliferative disorder. In certain embodiments, the cell proliferative disorder is cancer.

Regardless of the route of administration selected, the compounds of the disclosure, which may be used in a suitable hydrated form, and/or the pharmaceutical compositions of the present disclosure, are formulated into pharmaceutically acceptable dosage forms by conventional methods known to those of skill in the art.

Actual dosage levels and time course of administration of the active ingredients in the pharmaceutical compositions of the disclosure may be varied so as to obtain an amount of the active ingredient which is effective to achieve the desired therapeutic response for a particular patient, composition, and mode of administration, without being toxic to the patient. An exemplary dose range is from 0.01 to 100 mg/kg per day or 0.1 to 150 mg/kg per day.

In certain embodiments, the compound of the disclosure can be used in combination therapy with conventional cancer chemotherapeutics. Conventional treatment regimens for leukemia and for other tumors include radiation, drugs, or a combination of both.

Methods of Use

The compounds of the present disclosure may be used to inhibit the activity of tyrosine kinases, particularly including HER1 (EGFR), $HER^2$ and VEGF or to kill cancer cells. Therefore, the compounds of formula (I) are expected to be valuable as therapeutic agents. Accordingly, the present disclosure provides a method of treating or inhibiting or controlling a cell proliferative disorder in a patient in need of such treatment, comprising administering to the patient an effective amount of a compound of formula (I), or its pharmaceutical salt; or isomers or hydrates or solvates thereof;

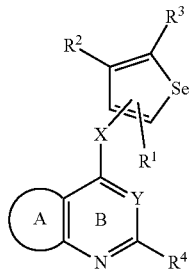

Formula (I)

wherein:
A ring is aryl or heteroaryl or heterocycloalkyl; the aryl is fused benzene ring and heteroaryl is 6-membered aromatic fused ring containing one, two or three nitrogen atoms; or the heteroaryl is 5-membered aromatic fused ring containing one or more heteroatoms selected from sulfur, oxygen, nitrogen and selenium, providing that no more than one oxygen or sulfur or selenium atom is present; such rings include pyridine, pyridazine, pyrazine, pyrimidine, thiophene, furan, pyrrole, selenophene, pyrazole, imidazole, oxazole, isoxazole, thiazole and isothiazole; heterocycloalkyl in general represents a mono- or bicyclic, saturated heterocyclic radical having a total number of 3 to 10 carbon atoms and up to 2 heteroatoms and/or heterogroups independently selected from the group consisting of N, O, S, SO and $SO_2$;

A ring is optionally substituted by one, two or more groups independently selected from hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondary-alkyl, $C_{1-6}$tertiary-alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino $C_{1-6}$alkyl, amino $C_{1-6}$alkoxy, $C_{1-6}$alkylamino$C_{1-6}$alkyl, di($C_{1-6}$alkyl)amino $C_{1-6}$alkyl, $C_{1-6}$alkylsulfinyl, $C_{1-6}$alkylsulfonyl, and a aryl, heteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$ alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino $C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl;

Y is N or C—$R^5$, wherein $R^5$ is selected from hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondary-alkyl, $C_{1-6}$tertiary-alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino $C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl;

X may be attached to either $2^{nd}$ or $3^{rd}$ position of the selenophene ring;

X is selected from $NR^6$, O, S, S(O), $S(O_2)$; wherein $R^6$ is selected from hydrogen, amino, $C_{1-6}$alkyl, halo$C_{1-6}$alkyl;

$R^1$, $R^2$, $R^3$, and $R^4$
selected from hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondary-alkyl, $C_{1-6}$tertiary-alkyl, $C_{2-6}$ alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl, and a aryl, heteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl) aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$ alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino $C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl.

Another aspect of the disclosure provides a method of treating or inhibiting or controlling a cell proliferative disorder in a patient in need of such treatment, comprising administering to the patient an effective amount of a composition comprising at least one selenophene compound of formula (I), or its pharmaceutical salt; or isomers or hydrates or solvates thereof; and at least one selected from pharmaceutically acceptable excipient, pharmaceutically acceptable diluent, and pharmaceutically acceptable carrier; and optionally further comprising at least one anti-tumor agent selected from Alkylating agents, Anti-metabolites, Hormonal therapy agents, Cytotoxic topoisomerase inhibiting agents, Anti-angiogenic compounds, Antibodies, VEGF inhibitors, EGFR (HERD inhibitors, HER2 inhibitors, CDK inhibitors, Proteasome inhibitors, Serine/threonine kinase (Raf inhibitors), Tyrosine kinase inhibitors, Androgen receptor antagonists and Aromatase inhibitors.

Another aspect of the present disclosure provides a method of treating or controlling tumor or cancer growth by blocking angiogenesis or by inhibiting vascular capillary formation with the administration of at least one selenophene compound of formula (I) or their salts or their compositions as defined above.

A method of treating or inhibiting, or controlling cell proliferative disorder, wherein the said administration comprises the routes selected from the group consisting of intraperitoneal (IP), intravenous (IV), oral (PO), intramuscular (IM), intracutaneous (IC), intradermal (ID), intrauterine, intratumoral and intrarectal.

In certain embodiments, the cell proliferative disorder is cancer. The term "treating" or "treatment" as stated throughout this document is used conventionally, e.g., the management or care of a subject for the purpose of combating, alleviating, reducing, relieving, improving the condition of a disease or disorder, such as a carcinoma or any malignancy.

The term "subject" or "patient" includes organisms which are capable of suffering from a cell proliferative disorder or who could otherwise benefit from the administration of a compound of the disclosure, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The term "cell proliferative disorder" includes disorders involving the undesired or uncontrolled proliferation of a cell. The compounds of the present disclosure can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this disclosure, or a pharmaceutically acceptable salt, isomer, polymorph, metabolite, hydrate or solvate thereof which is effective to treat or prevent the disorder. Cell proliferative or hyper-proliferative disorders in the context of this disclosure include, but are not limited to, e.g., psoriasis, keloids and other hyperplasias affecting the skin, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia (BPH), and solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Examples of breast cancer include, but are not limited to invasive ductal carcinoma, invasive lobular carcinoma, ductal carcinoma in situ, and lobular carcinoma in situ. Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, glioblastoma, medulloblastoma, ependymoma, as well as neuroectodermal and pineal tumor. Tumors of the male reproductive organs include, but are not limited to prostate and testicular cancer. Tumors of the female reproductive organs include, but are not limited to endometrial, cervical, ovarian, vaginal and vulvar cancer, as well as sarcoma of the uterus. Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers. Eye cancers include, but are not limited to intraocular melanoma and retinoblastoma. Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer. Head-and-neck cancers include, but are not limited to laryngeal, hypopharyngeal, nasopharyngeal, oropharyngeal cancer, lip and oral cavity cancer, and squamous cell cancer.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

Fibrotic proliferative disorders, i.e. the abnormal formation of extracellular matrices, that may be treated with the compounds and methods of the present disclosure include atherosclerosis, restenosis, hepatic cirrhosis, and mesangial cell proliferative disorders, including renal diseases such as glomerulonephritis, diabetic nephropathy, malignant nephrosclerosis, thrombotic microangiopathy syndromes, transplant rejection, and glomerulopathies.

Other conditions in humans or other mammals that may be treated by administering a compound of the present disclosure include tumor growth, retinopathy, including diabetic retinopathy, ischemic retinal-vein occlusion, retinopathy of prematurity and age-related macular degeneration, rheumatoid arthritis, psoriasis, and bullous disorders associated with subepidermal blister formation, including bullous pemphigoid, erythema multiforme and dermatitis herpetiformis.

The compounds of the present disclosure may also be used to prevent and treat diseases of the airways and the lung, diseases of the gastrointestinal tract as well as diseases of the bladder and bile duct.

The disorders mentioned above have been well characterized in humans, but also exist with a similar etiology in other animals, including mammals, and can be treated by administering a compound of formula (I) or their pharmaceutical compositions of the present disclosure.

The present disclosure is provided by the examples given below, which are provided by the way of illustration only, and should not be considered to limit the scope of the disclosure. Variation and changes, which are obvious to one skilled in the art, are intended to be within the scope and nature of the disclosure, which are defined in the appended claims.

EXAMPLES

Synthesis of Intermediates 1. 3-Amino-5-tert-butylselenophene-2-carboxamide

Step a

3-Chloro-4,4-dimethylpent-2-enenitrile

To an ice cold (0-5° C.) dimethylformamide (6.2 mL, 80 mmol) was added phosphorous oxychloride (3.75 mL, 40 mmol) dropwise with stirring for 15 min. To this cold mixture, tert-butyl methyl ketone (2.0 g, 20 mmol) was added dropwise maintaining the temperature of the reaction mixture between 45-55° C. for 10 min. The reaction mixture was slowly allowed to room temperature (rt) and stand for 30 min. To the reaction mixture, 1 mL of a total solution of hydroxylamine hydrochloride (5.56 g, 80 mmol) in dry DMF (8 mL) was added and the mixture was stirred at 70-80° C. for 5 min. Then the remaining solution of hydroxylamine hydrochloride in DMF was added thereafter at such a rate that the temperature of the reaction mixture rise above 145-155° C. After completion of the addition, the reaction mixture was allowed to rt for 30 min and diluted with cold water (200 mL). The solution was extracted with chloroform (3×100 mL) and the combined chloroform layer was washed with water, brine and dried over sodium sulfate. The solution was filtered and evaporated the solvent. The residue was chromatographed over silica gel using hexane-ethyl acetate (98:2) as eluent to give the product as a light green color oil (1.0 g, 35%). $^1$H NMR (400 MHz, CDCl$_3$): δ 5.56 (1H, s), 1.24 (9H, s).

Step b

Preparation of Sodium Selenide

Selenium (0.83 g) was added to a solution of sodium hydroxide (2.32 g) and sodium formaldehyde sulfoxylate (3.84 g) in water (11 mL). After stirring for 1 h at 50° C., the white precipitate was filtered under nitrogen atmosphere and rapidly used for the next step.

3-Amino-5-tert-butylselenophene-2-carbonitrile

To a suspension of sodium selenide (3.51 g, 27.87 mmol) in DMF (28 mL) was added a solution of 3-chloro-4,4-dimethylpent-2-enenitrile (4.0 g, 27.87 mmol) in DMF (10 mL) at rt for 5 min and stirred the mixture at 60-70° C. for 2 h. Then chloroacetonitrile (1.76 mL, 27.87 mmol) was added dropwise to the reaction mixture and again stirred at the same temperature for 2 h. Then, a solution of sodium methoxide (1.5 g, 27.87 mmol) in dry methanol (18 mL) was added dropwise and stirring was continued for 1 h. The mixture was allowed to rt and poured into cold water and stirred for 30 min. The precipitated solid was filtered and washed with water. The solid was recrystallized from chloroform-hexane to give the product as a brown color solid (5.06 g, 80%), mp 110-112° C. $^1$H NMR (400 MHz, CDCl$_3$): δ 6.59 (1H, s), 4.46 (2H, br s), 1.33 (9H, s); LC-MS (negative ion mode): m/z 225, 227 (M−H)$^-$.

Step c

3-Amino-5-(tert-butyl)selenophene-2-carboxamide

To a suspension of 3-amino-5-(tert-butyl)selenophene-2-carbonitrile (2.0 g) in aqueous sodium hydroxide solution (50 mL, 10%) was added ethanol (50 mL) and the mixture refluxed for 1 h. Ethanol was distilled off under vacuum (appr. 25 mL) and the mixture was allowed to cool to 5-10° C. The separated crystals were filtered off, washed with cold water and dried to give the product as a off-white color solid (1.8 g, 83%), mp 160-162° C. $^1$H NMR (400 MHz, CDCl$_3$): δ 6.58 (1H, s), 5.75 (2H, br s), 5.13 (2H, br s), 1.34 (9H, s).

2. 3-Amino-5-phenylselenophene-2-carboxamide

Step a

3-Chloro-3-phenylprop-2-enenitrile

The reaction of dimethylformamide, phosphorous oxychloride and acetophenone as described earlier gave the product as an oil (0.72 g, 53%). $^1$H NMR (400 MHz, CDCl$_3$): δ 7.64-7.67 (2H, m), 7.43-7.53 (3H, m), 6.02 (1H, s).

Step b

3-Amino-5-phenylselenophene-2-carbonitrile

The reaction of 3-chloro-3-phenylprop-2-enenitrile, sodium selenide and chloroacetonitrile as described earlier gave the product as a brown color solid (4.8 g, 53%), mp 162-164° C. (decomp). $^1$H NMR (400 MHz, CDCl$_3$): δ 7.46-7.49 (2H, m), 7.37-7.39 (3H, m), 7.01 (1H, s), 4.55 (2H, br s).

Step c

3-Amino-5-phenylselenophene-2-carboxamide

Hydrolysis of 3-amino-5-phenylselenophene-2-carbonitrile using aqueous sodium hydroxide solution as described earlier gave the product as golden yellow color solid (2.8 g, 67%), mp 184-186° C. $^1$H NMR (400 MHz, CDCl$_3$): δ 7.50-7.53 (2H, m), 7.36-7.38 (3H, m), 7.04 (1H, s), 5.84 (2H, br s), 5.12 (2H, br s).

3. 3-Amino-5-tert-butyl-2-nitroselenophene

The reaction of 3-chloro-4,4-dimethylpent-2-enenitrile, sodium selenide and bromonitromethane as described earlier gave the product as a yellow color solid, mp 112-114° C. $^1$H NMR (400 MHz, DMSO-d$_6$): δ 8.28 (2H, br s), 6.76 (1H, s), 1.28 (9H, s).

4. Methyl 4-amino-5-methylselenophene-2-carboxylate

Step a

Methyl 5-methyl-4-nitroselenophene-2-carboxylate

To an ice cold (0-10° C.) solution of methyl 5-methylselenophene-2-carboxylate (5.4 g, 26.6 mmol) in acetic anhydride (15 mL) was added an ice cold mixture of nitric acid (5.5 mL, 61.1 mmol, 70%) and acetic anhydride (10 mL) for 10 min. The reaction mixture was slowly allowed to rt for 1 h and stirred at room temperature (rt) for 16 h. The mixture was poured into ice cold water and stirred for 10 min. The solution was extracted with chloroform (3×100 mL) and the combined organic layer was washed with water, brine and dried over sodium sulfate. The solution was filtered and evaporated the solvent. The residue was chromatographed over silica gel column using hexane-ethyl acetate (90:10) as eluents to give the product as an pale yellow color solid (2.3 g, 35%), mp 90-92° C. $^1$H NMR (400 MHz, CDCl$_3$): δ 8.54 (1H, s), 3.90 (3H, s), 2.90 (3H, s).

Step b

Methyl 4-amino-5-methylselenophene-2-carboxylate

To a solution of methyl 5-methyl-4-nitroselenophene-2-carboxylate (2.3 g, 9.28 mmol) in a mixture of water (5 mL) and methanol (40 mL) was added conc. hydrochloric acid (1.0 mL). To the above solution was added iron powder (2.6 g, 46.4 mmol) followed by ammonium chloride (2.5 g, 46.4 mmol) at rt. The reaction mixture was refluxed for 1 h and was then allowed to cool to rt. The solution was filtered and basified with saturated sodium bicarbonate solution. The solution was extracted with ethyl acetate (4×100 mL) and the combined organic layer was dried over sodium sulfate and filtered. Solvent was evaporated and the residue was chromatographed over silica gel column using hexane-ethyl acetate (80:20) as eluent to give methyl 4-amino-5-methylselenophene-2-carboxylate (1.6 g, 79%), mp 66-68° C. $^1$H NMR (400 MHz, DMSO-d$_6$): δ 7.57 (1H, s), 4.72 (2H, br s), 3.73 (3H, s), 2.24 (3H, s).

5. 3-Hydroxy-5-tert-butylselenophene-2-carboxamide

Step a

3-Chloro-4,4-dimethylpent-2-enal

Phosphorous oxychloride (18.77 mL, 200 mmol) was added dropwise to DMF (30.8 mL, 400 mmol) at 0-5° C. for 30 min. Pinacolone (10 g, 100 mmol) was added dropwise to the reaction mixture at the same temperature for 30 min. The mixture was allowed to rt and stirred for 2 h. The reaction mixture was poured into ice cold water and basified with ammonia solution. The solution was extracted with chloroform (3×200 mL) and the combined chloroform layer was washed with water, brine and dried over sodium sulfate. The solution was filtered and evaporated the solvent. The residue was chromatographed over silica gel column using hexane-EtoAc (97:3) as eluents to give the product as a pale green color oil (11.7 g, 80%).

Step b

3-Chloro-4,4-dimethylpent-2-enoic acid

A solution of sodium hydroxide (1.09 g, 27.3 mmol) in water (10 mL) was added to a solution of silver nitrate (2.32 g, 13.65 mmol) in water (15 mL) at ice cold temperature for 15 min. 3-Chloro-4,4-dimethylpent-2-enal (1.0 g, 6.825 mmol) was added dropwise at the same temperature for 15 min. The reaction mixture was allowed to rt and stirred for 1 h. The reaction mixture was poured into ice cooled water and filtered through hyflowgel to remove black particles. The hyflowgel bed was washed with hot water and cooled. The solution was acidified with dil. HCl and the solution was extracted with chloroform (3×100 mL) and the combined organic layer was washed with brine and dried over sodium sulfate. The solution was filtered and evaporated the solvent to give the product a white color solid (1.0 g, 91%), mp 146-148° C. $^1$H NMR (400 MHz, CDCl$_3$): δ 8.02 (1H, br s), 6.11 (1H, s), 1.24 (9H, s); LC-MS (negative ion mode): m/z 161, 163 (M−H)$^-$.

Step c

Methyl 3-chloro-4,4-dimethylpent-2-enoate

To a solution of 3-chloro-4,4-dimethylpent-2-enoic acid (0.8 g, 4.92 mmol) in methanol (20 mL) was added thionyl chloride (0.714 mL, 9.846 mmol) drop wise under stirring at ice cold temperature. The reaction mixture was refluxed for 2 h and attained to rt. The mixture was poured into ice cooled water and stirred for 15 min. The solution was extracted with chloroform (3×100 mL) and the combined organic layer was washed with water, brine, dried over sodium sulfate and filtered. Solvent was evaporated and the residue was chromatographed over silica gel column using hexane-ethyl acetate (95:5) as eluents to give the product as a pale green color oil (750 mg, 87%). $^1$H NMR (400 MHz, CDCl$_3$): δ 6.08 (1H, s), 3.75 (3H, s), 1.24 (9H, s).

Step d

5-tert-Butyl-3-hydroxyselenophene-2-carbonitrile

To a suspension of sodium selenide (5.35 g, 42.49 mmol) in DMF (43 mL) was added a solution of methyl 3-chloro-4,4-dimethylpent-2-enoate (7.5 g, 42.49 mmol) in DMF (10 mL) at rt for 5 min and stirred the mixture at 60-70° C. for 2 h. Then chloroacetonitrile (2.785 mL, 42.49 mmol) was added dropwise to the reaction mixture and again stirred at 60-70° C. for 2 h. Then, a solution of sodium methoxide (2.29 g, 42.49 mmol) in dry methanol (26 mL) was added dropwise and stirring was continued for 1 h at the same temperature. The reaction mixture was poured into ice cold water and acidified with dil. HCl. The solution was extracted with chloroform (3×200 mL) and the combined chloroform layer was washed with water, brine and dried over sodium sulfate. The solution was filtered and evaporated the solvent. The residue was chromatographed over silica gel column using hexane-EtOAc (80:20) as eluents to give the product as a red color oil (7.5 g, 77%). $^1$H NMR (400 MHz, CDCl$_3$): δ 6.76 (1H, s), 1.35 (9H, s); LC-MS (negative ion mode): m/z 226, 228 (M−H)$^-$.

Step e

5-tert-Butyl-3-hydroxyselenophene-2-carboxamide

To an ice cold solution of 5-tert-butyl-3-hydroxyselenophene-2-carbonitrile (0.5 g) in trifluoroacetic acid (2 mL) was added H$_2$SO$_4$ (0.5 mL) dropwise for 15 min. The reaction mixture was allowed to rt and stirred for 6 h. The reaction mixture was poured into ice cold water extracted with chloroform (3×50 mL). The combined chloroform layer was washed with water, brine and dried over sodium sulfate. The solution was filtered and evaporated the solvent. The residue was chromatographed over silica gel column using hexane-EtOAc (75:25) as eluents to give the product as a brown color solid (460 mg, 86%), mp 164-168° C. $^1$H NMR (400 MHz, CDCl$_3$): δ 11.53 (1H, br s), 6.81 (1H, s), 5.35 (2H, s), 1.35 (9H, s); LC-MS (negative ion mode): m/z 244, 246 (M−H)$^-$.

Example 1

Synthesis of 3-(6,7-dimethoxyquinazolin-4-ylamino)-5-tert-butylselenophene-2-carboxamide (compd. 1)

Step a

3-(6,7-Dimethoxyquinazolin-4-ylamino)-5-tert-butylselenophene-2-carboxamide To a solution of 4-chloro-6,7-dimethoxyquinazoline (500 mg, 2.23 mmol) in DMF (20 mL) was added sequentially 3-amino-5-tert-butylselenophene-2-carboxamide (820 mg, 3.34 mmol), powdered NaOH (270 mg, 6.69 mmol) and catalytic amount of KI at rt and the mixture was stirred at rt for 16 h. The mixture was poured into ice cooled water and stirred for 10 min. The solid separated was filtered, washed with water and dried (730 mg, 76%). The crude product was further chromatographed and recrystallized from chloroform-methanol to give the product as a pale yellow color solid, mp 248-252° C. IR (KBr) v$_{max}$ 3470, 3134, 2960, 1626, 1577, 1469, 1385, 1238, 1211, 1133, 1010, 856, 750 cm$^{-1}$; $^1$H NMR (400 MHz, DMSO-d$_6$): δ 12.65 (1H, s, exchangeable with D$_2$O), 8.74 (1H, s), 8.62 (1H, s), 7.64 (2H, br s, exchangeable with D$_2$O), 7.36 (1H, s), 7.25 (1H, s), 3.96 (3H, s), 3.95 (3H, s), 1.42 (9H, s); $^{13}$C NMR (100 MHz, DMSO-d$_6$): δ 168.3, 167.5, 154.5, 153.8, 152.9, 149.4, 146.9, 146.1, 120.7, 111.8, 108.7, 107.5, 99.8, 55.9, 55.5, 36.5, 32.2; LC-MS (positive ion mode): m/z 433, 435 (M+H)$^+$.

Step b

HCl Salt

To a solution of 3-(6,7-dimethoxyquinazolin-4-ylamino)-5-tert-butylselenophene-2-carboxamide (100 mg) in dioxane (10 mL) was added HCl in dioxane until the pH paper showed red color (1 mL) at rt. The solution was stirred for 30 min and the separated salt was filtered, washed with dioxane and dried to give the product as a yellow color solid (80 mg), mp 234-238° C. LC-MS (positive ion mode): m/z 433, 435 (M−HCl+H)$^+$.

Example 2

Synthesis of 3-(6,7,8-trimethoxyquinazolin-4-ylamino)-5-tert-butylselenophene-2-carboxamide (Compd. 2)

Step a

3-(6,7,8-Trimethoxyquinazolin-4-ylamino)-5-tert-butylselenophene-2-carboxamide The reaction of 4-chloro-6,7,8-trimethoxyquinazoline with 3-amino-5-tert-butylselenophene-2-carboxamide in presence of DMF/NaOH as described in Example 1 gave the title compound as an off-white color solid, mp 218-220° C. $^1$H NMR (400 MHz, CDCl$_3$): δ 12.08 (1H, br s, exchangeable with D$_2$O), 8.87 (1H, s), 8.78 (1H, s), 7.20 (1H, s), 5.49 (2H, br s, exchangeable with D$_2$O), 4.15 (3H, s), 4.07 (3H, s), 4.06 (3H, s), 1.47 (9H, s); $^{13}$C NMR (100 MHz, CDCl$_3$): δ 169.0, 168.6, 154.7, 153.1, 152.6, 147.9, 147.6, 146.6, 142.0, 121.7, 112.0, 109.4, 95.9, 62.1, 61.3, 56.1, 37.2, 32.6; LC-MS (positive ion mode): m/z 463, 465 (M+H)$^+$.

Step b

HCl Salt 3-(6,7,8-Trimethoxyquinazolin-4-ylamino)-5-tert-butylselenophene-2-carboxamide is treated with HCl in dioxane as described in Example 1, gave the HCl salt as a pale yellow color solid, mp 184-186° C.

Example 3

Synthesis of 3-(6-(3-morpholinopropoxy)-7-methoxyquinazolin-4-ylamino)-5-tert-butylselenophene-2-carboxamide (Compd. 3)

Step a 3-(6-(3-morpholinopropoxy)-7-methoxyquinazolin-4-ylamino)-5-tert-butylselenophene-2-carboxamide The reaction of 4-chloro-7-methoxy-6-(3-morpholinopropoxy)quinazoline with 3-amino-5-tert-butylselenophene-2-carboxamide in the presence of DMF/NaOH as described in Example 1 gave title compound a pale yellow color solid, mp 208-212° C. IR (KBr) v$_{max}$ 3438, 3158, 2949, 1618, 1570, 1385, 1228, 1127, 1027, 859 cm$^{-1}$; $^1$H NMR (400 MHz, CDCl$_3$): δ 12.01 (1H, s, exchangeable with D$_2$O), 8.86 (1H, s), 8.72 (1H, s), 7.38 (1H, s), 7.23 (1H, s), 5.37 (2H, br s), 4.32 (2H, t, J=6.4 Hz), 4.01 (3H, s), 3.73 (4H, t, J=4.6 Hz), 2.65 (2H, t, J=7.2 Hz), 2.51-2.52 (4H, m), 2.14 (2H, pentet, J=7.0 Hz), 1.47 (9H, s); $^{13}$C NMR (100 MHz, CDCl$_3$): δ 168.9, 168.7, 155.2, 154.5, 153.4, 149.3, 148.2, 147.6, 121.8, 109.8, 109.2, 107.7, 101.4, 67.5, 67.0, 56.2, 55.5, 53.7, 37.2, 32.6, 26.2; LC-MS (negative ion mode): m/z 544, 546 (M–H)$^-$.

Step b

HCl Salt 3-(6-(3-Morpholinopropoxy)-7-methoxyquinazolin-4-ylamino)-5-tert-butylselenophene-2-carboxamide is treated with HCl in dioxane as described in Example 1, gave the HCl salt as an yellow color solid, mp 262-264° C. LC-MS (negative ion mode): m/z 544, 546 (M–HCl–H)$^-$.

Example 4

Synthesis of [5-(tert-butyl)-2-nitroselenophen-3-yl][7-methoxy-6-(3-morpholino-propoxy)quinazolin-4-yl]amine (Compd. 4)

Step a

[5-(tert-Butyl)-2-nitroselenophen-3-yl][7-methoxy-6-(3-morpholinopropoxy)quinazolin-4-yl]amine The reaction of 4-chloro-7-methoxy-6-(3-morpholinopropoxy)quinazoline with 5-(tert-butyl)-2-nitroselenophene-3-ylamine in the presence of DMF/NaOH as described in Example 1 gave title compound as a yellow color solid, mp 172-174° C. IR (KBr) v$_{max}$ 3431, 2942, 2860, 1616, 1436, 1309, 1281, 1197, 1121, 1025, 863 cm$^{-1}$; $^1$H NMR (400 MHz, CDCl$_3$): δ 11.67 (1H, s, exchangeable with D$_2$O), 8.90 (1H, s), 8.83 (1H, s), 7.30 (1H, s), 7.25 (1H, s), 4.30 (2H, t, J=6.2 Hz), 4.03 (3H, s), 3.73 (4H, t, J=4.4 Hz), 2.61 (2H, t, J=7.2 Hz), 2.51 (4H, br s), 2.14 (2H, pentet, J=6.6 Hz), 1.47 (9H, s); $^{13}$C NMR (100 MHz, CDCl$_3$): δ 176.6, 156.0, 153.4, 152.8, 150.3, 148.4, 144.9, 130.1, 120.1, 109.9, 107.8, 99.8, 67.5, 67.0, 56.3, 55.4, 53.8, 37.9, 32.0, 26.1; LC-MS (positive ion mode): m/z 548, 550 (M+H)$^+$.

Step b

HCl Salt

[5-(tert-Butyl)-2-nitroselenophen-3-yl][7-methoxy-6-(3-morpholinopropoxy)-quinazolin-4-yl]amine is treated with HCl in dioxane as described in Example 1, gave the HCl salt as an yellow color solid, mp 240-242° C.; LC-MS (positive ion mode): m/z 548, 550 (M–HCl+H)$^+$.

Example 5

Synthesis of 3-(7-(3-morpholinopropoxy)-6-methoxyquinazolin-4-ylamino)-5-tert-butylselenophene-2-carboxamide (Compd. 5)

Step a 3-(7-(3-Morpholinopropoxy)-6-methoxyquinazolin-4-ylamino)-5-tert-butylselenophene-2-carboxamide The reaction of 4-chloro-7-(3-morpholinopropoxy)-6-methoxyquinazoline with 3-amino-5-tert-butylselenophene-2-carboxamide in the presence of DMF/NaOH as described in Example 1 gave title compound as a pale yellow color solid, mp 216-220° C. IR (KBr) v$_{max}$ 3342, 3120, 2957, 2853, 1633, 1572, 1497, 1457, 1393, 1315, 1234, 1141, 1113, 1021, 903, 854, 798 cm$^{-1}$; $^1$H NMR (400 MHz, CDCl$_3$): δ 12.06 (1H, s, exchangeable with D$_2$O), 8.86 (1H, s), 8.71 (1H, s), 7.34 (1H, s), 7.25 (1H, s), 5.57 (2H, s, exchangeable with D$_2$O), 4.25 (2H, t, J=6.6 Hz), 4.06 (3H, s), 3.74 (4H, t, J=4.4 Hz), 2.59 (2H, t, J=7.2 Hz), 2.51 (4H, br s), 2.10-2.16 (2H, m), 1.46 (9H, s); $^{13}$C NMR (100 MHz, CDCl$_3$): δ 168.9, 168.6, 154.4, 154.3, 153.3, 150.1, 148.1, 147.4, 121.7, 109.6, 109.2, 108.3, 100.3, 67.3, 66.8, 56.2, 55.3, 53.7, 37.2, 32.6, 25.9; LC-MS (positive ion mode): m/z 546, 548 (M+H)$^+$.

Step b

HCl Salt 3-(7-(3-Morpholinopropoxy)-6-methoxyquinazolin-4-ylamino)-5-tert-butylselenophene-2-carboxamide is treated with HCl in dioxane as described in Example 1, gave the HCl salt as a pale yellow color solid, mp 262-264° C. LC-MS (positive ion mode): m/z 546, 548 (M–HCl+H)$^+$.

Example 6

Synthesis of 3-(6,7-bis(2-methoxyethoxy)quinazolin-4-ylamino)-5-tert-butylselenophene-2-carboxamide (Compd. 6)

Step a 3-(6,7-Bis(2-methoxyethoxy)quinazolin-4-ylamino)-5-tert-butylselenophene-2-carboxamide The reaction of 4-chloro-6,7-bis(2-methoxyethoxy) quinazoline with 3-amino-5-tert-butylselenophene-2-carboxamide in the presence of DMF/NaOH as described in Example 1 gave title compound as a pale yellow color solid, mp 198-204° C. IR (KBr) $v_{max}$ 3430, 3162, 2961, 1627, 1576, 1474, 1463, 1386, 1321, 1242, 1131, 1092, 937, 859 cm$^{-1}$; $^1$H NMR (400 MHz, CDCl$_3$): δ 12.63 (1H, s, exchangeable with D$_2$O), 8.67 (1H, s), 8.64 (1H, s), 7.66 (2H, br s, exchangeable with D$_2$O), 7.40 (1H, s), 7.28 (1H, s), 4.25-4.33 (4H, m), 3.75-3.80 (4H, m), 3.37 (3H, s), 3.36 (3H, s), 1.41 (9H, s); $^{13}$C NMR (100 MHz, CDCl$_3$): δ 168.2, 167.4, 153.9, 153.8, 153.0, 148.6, 147.0, 146.0, 120.8, 112.1, 108.7, 108.6, 101.5, 70.0 (2C), 68.2, 68.0, 58.4, 58.3, 36.5, 32.2; LC-MS (positive ion mode): m/z 521, 523 (M+H)$^+$.

Step b

HCl Salt 3-(6,7-Bis(2-methoxyethoxy)quinazolin-4-ylamino)-5-tert-butylselenophene-2-carboxamide is treated with HCl in dioxane as described in Example 1, gave the HCl salt as a yellow color solid, mp 224-226° C. LC-MS (positive ion mode): m/z 521, 523 (M–HCl+H)$^+$.

Example 7

Synthesis of 3-(6-(3-morpholinopropoxy)-7-methoxyquinazolin-4-ylamino)-5-phenyl-selenophene-2-carboxamide (Compd. 7)

Step a 3-(6-(3-Morpholinopropoxy)-7-methoxyquinazolin-4-ylamino)-5-phenyl-selenophene-2-carboxamide The reaction of 4-chloro-7-methoxy-6-(3-morpholinopropoxy)quinazoline with 3-amino-5-phenylselenophene-2-carboxamide in the presence of DMF/NaOH as described in Example 1 gave title compound as a yellow color solid, mp 236-240° C. IR (KBr) $v_{max}$ 34369, 3158, 2935, 1635, 1579, 1387, 1321, 1238, 1216, 1145, 1113, 902, 846 cm$^{-1}$; $^1$H NMR (400 MHz, DMSO-d$_6$): δ 12.50 (1H, s), 9.16 (1H, s), 8.65 (1H, s), 7.77 (2H, br s), 7.68-7.70 (2H, m), 7.44-7.52 (3H, m), 7.39 (1H, s), 7.26 (1H, s), 4.20 (2H, br s), 3.96 (3H, s), 3.58 (4H, br s), 2.50 (2H, br s), 2.40 (4H, br s), 2.00 (2H, pentet, J=6.5 Hz); LC-MS (positive ion mode): m/z 566, 568 (M+H)$^+$.

Step b

HCl Salt 3-(6-(3-Morpholinopropoxy)-7-methoxyquinazolin-4-ylamino)-5-phenyl-selenophene-2-carboxamide is treated with HCl in dioxane as described in Example 1, gave the HCl salt as a yellow color solid, mp 266-270° C. LC-MS (negative ion mode): m/z 564, 566 (M–HCl–H)—.

Example 8

Synthesis of 3-(6-aminoquinazolin-4-ylamino)-5-tert-butylselenophene-2-carboxamide (Compd. 8)

Step a 3-(6-Nitroquinazolin-4-ylamino)-5-tert-butylselenophene-2-carboxamide

To a solution of 4-chloro-6-nitroquinazoline (1.1 g, 5.2 mmol) in isopropanol (10 mL) was added 5-tert-butyl-3-amino-selenophene-2-carboxamide (2.58 g, 10.50 mmol) at rt and the mixture was stirred for 30 min. The mixture was poured into ice cold water and stirred for 15 min The precipitated solid was filtered, washed with water and dried to give the product as a pale yellow color solid (2.1 g, 95%), mp 280-282° C. $^1$H NMR (400 MHz, DMSO-d$_6$): δ 13.23 (1H, br s), 9.05 (1H, br s), 8.85 (1H, s), 8.56-8.60 (2H, m), 7.98 (1H, d, J=9.2 Hz), 7.80 (2H, br s), 1.43 (9H, s); LC-MS (negative ion mode): m/z 416, 418 (M–H)$^-$.

Step b 3-(6-Aminoquinazolin-4-ylamino)-5-tert-butyl selenophene-2-carboxamide

To a suspension of 3-(6-nitroquinazolin-4-ylamino)-5-tert-butylselenophene-2-carboxamide (1.0 g, 2.38 mmol) in methanol (18 mL) was added concentrated HCl (0.24 mL, 2.39 mmol) at rt. Iron powder (668 mg, 11.93 mmol) was added slowly for 10 min, followed by ammonium chloride (638 mg, 11.93 mmol). Water (5 mL) was added to the reaction mixture and stirred at the refluxing temperature for 1 h. The reaction mixture allowed to rt and filter to remove iron. The solution was poured into ice cold water and stirred for 15 min. The solution was extracted with ethyl acetate (3×100 mL) and the combined organic layer was washed with water, brine and dried over sodium sulfate. The solution was filtered and evaporated the solvent. The residue was chromatographed over silica gel column using hexane-ethyl acetate (80:20) as eluents to give the product as a yellow color solid (752 mg, 81%), mp 160-162° C. IR (KBr) $v_{max}$ 3430, 3340, 3222, 2961, 1631, 1598, 1569, 1390, 1314, 1262, 1185, 1130, 836 cm$^{-1}$; $^1$H NMR (400 MHz, DMSO-d$_6$): δ 12.29 (1H, br s, exchangeable with D$_2$O), 8.76 (1H, s), 8.44 (1H, s), 7.48-7.55 (3H, m), 7.26 (1H, br s), 6.96 (1H, br s), 5.85 (2H, br s, exchangeable with D$_2$O), 1.40 (9H, s); $^{13}$C NMR (100 MHz, DMSO-d$_6$): δ 166.4, 165.5, 151.9, 148.1, 146.6, 144.8, 141.2, 127.6, 122.5, 119.6, 115.0, 110.0, 97.3, 34.9, 30.7; LC-MS (positive ion mode): m/z 388, 390 (M+H)$^+$.

Step c

HCl Salt 3-(6-Aminoquinazolin-4-ylamino)-5-tert-butylselenophene-2-carboxamide is treated with HCl in dioxane as described in Example 1, gave the HCl salt as a yellow color solid, mp 170-172° C. LC-MS (positive ion mode): m/z 388, 390 (M–HCl+H)$^+$.

Example 9

Synthesis of 3-(6-(2-chloroacetamido)quinazolin-4-ylamino)-5-tert-butylselenophene-2-carboxamide (Compd. 9)

Step a 3-(6-(2-chloroacetamido)quinazolin-4-ylamino)-5-tert-butylselenophene-2-carboxamide To a solution of 3-(6-aminoquinazolin-4-ylamino)-5-tert-butylselenophene-2-carboxamide (510 mg, 1.31 mmol) in THF (10 mL) was added a solution of chloroacetyl chloride (0.105 mL, 1.31 mmol) in THF (1.0 mL) at rt. The mixture was stirred at rt for 30 min (solid separated). The solution was poured into ice cold water and stirred for 15 min. The separated solid was filtered, washed with water and dried to give the product as a yellow color solid (540 mg, 80%). This crude product was further chromatographed and recrystallized from chloroform-methanol. Mp 262-264° C.; IR (KBr) $v_{max}$ 3437, 3109, 2961, 1706, 1652, 1608, 1575, 1541, 1464, 1386, 1355, 1311, 1241, 1137, 1086, 858, 834, 790 cm$^{-1}$; $^1$H NMR (400 MHz, DMSO-d$_6$): δ 12.79 (1H, s, exchangeable with D$_2$O), 10.83 (1H, s, exchangeable with D$_2$O), 8.83 (1H, s), 8.73 (1H, s), 8.60 (1H, br s), 8.01-8.03 (1H, m), 7.89 (1H, d, J=8.8 Hz), 7.68 (2H, br s), 4.41 (2H, s), 1.47 (9H, s); $^{13}$C NMR (100 MHz, DMSO-d$_6$): δ 167.9, 167.2, 164.9, 154.9, 153.2, 146.3, 145.5, 137.2, 128.7, 126.7, 121.1, 115.2, 113.1, 110.0, 43.3, 36.5, 32.2; LC-MS (negative ion mode): m/z 462, 464, 466 (M−H)$^-$.

Step b

HCl Salt 3-(6-(2-Chloro acetamido)quinazolin-4-ylamino)-5-tert-butylselenophene-2-carboxamide is treated with HCl in dioxane as described in Example 1, gave the HCl salt as a yellow color solid, mp 276-278° C. LC-MS (negative ion mode): m/z 462, 464, 466 (M−HCl−H)$^-$.

Example 10

Synthesis of methyl 4-(6-(3-morpholinopropoxy)-7-methoxyquinazolin-4-ylamino)-5-methylselenophene-2-carboxylate (Compd. 10)

Step a

Methyl 4-(6-(3-morpholinopropoxy)-7-methoxyquinazolin-4-ylamino)-5-methylselenophene-2-carboxylate To a solution of 2-amino-4-methoxy-5-(3-morpholin-4-yl-propoxy)benzonitrile (1.0 g, 3.436 mmol) in toluene (15 mL) was added sequentially acetic acid (0.2 mL) and dimethyl formamide-dimethylacetal (1.03 mL, 7.216 mol). The reaction mixture was stirred at 105° C. for 3 h. While stirring, methanol was collected using the Dean-Stark apparatus. Toluene was evaporated under vacuum to give as a yellow color semi-solid. The residue was dissolved in acetic acid (20 mL) and methyl 4-amino-5-methylselenophene-2-carboxylate (750 mg, 4.12 mmol) was added. The reaction mixture was stirred at 125-130° C. for 3 h. The reaction mixture was attained to rt and poured into ice cooled water and extracted with chloroform (to remove impurities). The aqueous solution was basified with ammonia solution and extracted with chloroform (3×100 mL) and the combined organic layer was washed with water, brine and dried over sodium sulfate. The solution was filtered and evaporated the solvent. The residue was chromatographed over silica gel column using chloroform-methanol (95:5) as eluents to give the crude product (1.13 g, 68%). The crude product was further recrystallized from hexane-ethyl acetate to give the product as an off-white color solid, mp 172-174° C. IR (KBr) $v_{max}$ 3429, 2949, 1705, 1622, 1586, 1507, 1470, 1430, 1386, 1280, 1237, 1143, 1112, 1069, 1044, 850 cm$^{-1}$; $^1$H NMR (400 MHz, CDCl$_3$): δ 8.58 (1H, s), 8.11 (1H, s), 7.29 (1H, br s, exchangeable with D$_2$O), 7.22 (1H, s), 7.18 (1H, s), 4.12 (2H, t, J=6.6 Hz), 3.97 (3H, s), 3.84 (3H, s), 3.71 (4H, t, J=4.4 Hz), 2.54 (2H, t, J=7.0 Hz), 2.46 (7H, br s), 2.07 (2H, pentet, J=6.7 Hz); $^{13}$C NMR (100 MHz, CDCl$_3$): δ 163.4, 157.2, 155.3, 153.9, 148.9, 147.5, 145.3, 135.4, 134.7, 132.2, 108.6, 107.9, 101.3, 67.6, 66.9, 56.1, 55.3, 53.7, 52.2, 26.1, 15.5; LC-MS (positive ion mode): m/z 519, 520 (M+H)±.

Step b

HCl Salt

Methyl 4-(6-(3-morpholinopropoxy)-7-methoxyquinazolin-4-ylamino)-5-methylselenophene-2-carboxylate is treated with HCl in dioxane as described in Example 1, gave the HCl salt as an off-white color solid, mp 198-200° C. LC-MS (positive ion mode): m/z 519, 520 (M−HCl+H)$^+$.

Example 11

Synthesis of 4-(6-(3-morpholinopropoxy)-7-methoxyquinazolin-4-ylamino)-5-methylselenophene-2-carboxamide (Compd. 11)

Step a 4-(6-(3-Morpholinopropoxy)-7-methoxyquinazolin-4-ylamino)-5-methylselenophene-2-carboxamide A solution of compound 10 (1.0 g) in THF (20 mL) was added to a cooled solution of ammonia (100 mL) and stirred at rt for 5 days. The solution was poured into ice cooled water and extracted with chloroform (3×100 mL). The combined organic layer was washed with water, brine and dried over sodium sulfate. The solution was filtered and evaporated the solvent. The residue was chromatographed over silica gel column using chloroform-methanol (90:10) as eluents to give the product as an off-white color solid (690 mg, 71%), which was recrystallized from chloroform-methanol, mp 90-92° C. IR (KBr) $v_{max}$ 3342, 2954, 1655, 1588, 1506, 1473, 1391, 1330, 1221, 1115, 1066, 999, 857 cm$^{-1}$; $^1$H NMR (400 MHz, CDCl$_3$): δ 9.34 (1H, s, exchangeable with D$_2$O), 8.35 (1H, s), 7.97 (1H, s), 7.81 (1H, br s), 7.82 (1H, s), 7.29 (1H, br s), 7.17 (1H, s), 4.17 (2H, t, J=6.2 Hz), 3.94 (3H, s), 3.58-3.60 (4H, m), 2.52 (2H, br s), 2.38-2.42 (7H, br s), 1.98-2.02 (2H, m); $^{13}$C NMR (100 MHz, CDCl$_3$): δ 163.7, 157.6, 154.4, 153.3, 148.1, 146.6, 142.5, 139.2, 135.1, 131.5, 108.5, 107.2, 102.9, 67.1, 66.1, 55.8, 54.9, 53.4, 25.8, 15.0; LC-MS (negative ion mode): m/z 502, 504 (M−H)$^-$.

Step b

HCl Salt 4-(6-(3-Morpholinopropoxy)-7-methoxyquinazolin-4-ylamino)-5-methylselenophene-2-carboxamide is treated with HCl in dioxane as described in Example 1, gave the HCl salt as a pale yellow color solid, mp 252-254° C. LC-MS (negative ion mode): m/z 502, 504 (M−HCl−H)−.

Example 12

Synthesis of 5-tert-butyl-3-(pyridino[2,3-d]pyrimidin-4-ylamino)selenophene-2-carboxamide (Compd. 12)

Step a 5-tert-Butyl-3-(pyridino[2,3-d]pyrimidin-4-ylamino)selenophene-2-carboxamide The reaction of 4-chloropyridino[2,3-d]pyrimidine with 3-amino-5-tert-butylselenophene-2-carboxamide in the presence of DMF/NaOH as described in Example 1 gave title compound as a yellow color solid, mp 222-224° C. IR (KBr) $v_{max}$ 3310, 3180, 2961, 1616, 1572, 1383, 1332, 1316, 1280, 1245, 1226, 1090 cm$^{-1}$; $^1$H NMR (400 MHz, CDCl$_3$+ DMSO-d$_6$): δ 9.10 (1H, dd, J=4.4, 1.6 Hz), 8.96 (1H, s), 8.81 (1H, s), 8.55 (1H, dd, J=8.4, 1.6 Hz), 7.54 (1H, dd, J=8.4, 4.4 Hz), 6.50 (2H, br s), 1.48 (9H, s); $^{13}$C NMR (100 MHz, CDCl$_3$+DMSO-d$_6$): 168.6, 168.3, 158.6, 157.9, 156.5, 155.8, 146.1, 131.3, 121.9, 121.1, 111.7, 110.3, 36.8, 32.2; LC-MS (negative ion mode): m/z 372, 374 (M−H)−.

Step b

HCl Salt 5-tert-Butyl-3-(pyridino[2,3-d]pyrimidin-4-ylamino)selenophene-2-carboxamide is treated with HCl in dioxane as described in Example 1, gave the HCl salt as a yellow color solid, mp 242-244° C. LC-MS (negative ion mode): m/z 372, 374 (M−HCl−H)−.

Example 13

Synthesis of 3-(5-ethyl-6-methylthiopheno[2,3-d]pyrimidin-4-ylamino)-5-tert-butylselenophene-2-carboxamide (Compd. 13)

Step a

2-Amino-4-ethyl-5-methylthiophene-3-carbonitrile

To a solution of diethyl ketone (3 g, 34.88 mmol) in ethanol (30 mL) was added sequentially malononitrile (2.3 g, 34.88 mmol), sulfur powder (1.1 g, 34.88 mmol) and triethyl amine (36.4 mL, 348.8 mmol) at rt. The reaction mixture was refluxed for 1 h. The reaction mixture was allowed to rt and powered into ice cold water. The solution was stirred for 15 min and extracted with ethyl acetate (3×100 mL). The combined EtOAc layer was washed with water, brine and dried over sodium sulfate. The residue was chromatographed over silica gel column using hexane-ethyl acetate (95:5) as eluents to give the product as an off-white color solid (700 mg, 12%), mp 100-105° C. $^1$H NMR (400 MHz, CDCl$_3$): δ 4.54 (2H, br s), 2.48 (2H, q, J=6.8 Hz), 2.17 (3H, s), 1.15 (3H, t, J=7.6 Hz); LC-MS (negative ion mode): m/z 165 (M−H)−.

Step b

5-Ethyl-6-methyl-3-hydrothiopheno[2,3-d]pyrimidin-4-one

To an ice cold solution of 2-amino-4-ethyl-5-methylthiophene-3-carbonitrile (0.5 g) in formic acid (5 mL) was added concentrated sulfuric acid (2 mL) slowly for 10 min. The mixture was stirred at 90-100° C. for 2 h and allowed to rt. The mixture was poured into ice cold water and stirred for 15 min. The precipitated solid was filtered, washed with ice cold water and dried. The product was chromatographed over silica gel column using hexane-ethyl acetate (70:30) as eluents to give the product as an off-white color solid (400 mg, 68%), mp 182-184° C. $^1$H NMR (400 MHz, CDCl$_3$): δ 11.97 (1H, br s), 7.96 (1H, s), 2.98 (2H, q, J=7.5 Hz), 2.44 (3H, s), 1.20 (3H, t, J=7.4 Hz); LC-MS (negative ion mode): m/z 193 (M−H)−.

Step c

4-Chloro-5-ethyl-6-methylthiopheno[2,3-d]pyrimidine

A mixture of 5-ethyl-6-methyl-3-hydrothiopheno[2,3-d]pyrimidin-4-one (0.5 g), thionyl chloride (5 mL) and catalytic amount of DMF (0.2 mL) was refluxed for 1 h. Solvents were removed under vacuum and the mixture was diluted with ice cold water and stirred for 10 min. The solution was extracted with chloroform (3×100 mL) and the combined chloroform layer was washed with water, brine and dried over sodium sulfate. The solution was filtered and evaporated the solvent. The residue was triturated with hexane to give the product as a dark brown color solid (400 mg, 73%), mp 52-56° C. $^1$H NMR (400 MHz, CDCl$_3$): δ 8.73 (1H, s), 3.05 (2H, q, J=7.5 Hz), 2.55 (3H, s), 1.24 (3H, t, J=7.6 Hz).

Step d 3-(5-Ethyl-6-methylthiopheno[2,3-d]pyrimidin-4-ylamino)-5-tert-butylselenophene-2-carboxamide The reaction of 4-chloro-5-ethyl-6-methylthieno[2,3-d]pyrimidine with 3-amino-5-tert-butylselenophene-2-carboxamide in the presence of DMF/NaOH as described in Example 1 gave title compound as an off-white color solid, mp 234-236° C. IR (KBr) $v_{max}$ 3332, 3154, 2962, 1665, 1585, 1362, 1221, 1048, 927, 838, 778 cm$^{-1}$; $^1$H NMR (400 MHz, CDCl$_3$): δ 11.04 (1H, s, exchangeable with D$_2$O), 8.64 (1H, s), 8.56 (1H, s), 5.34 (2H, br s, exchangeable with D$_2$O), 3.15 (2H, q, J=7.5 Hz), 2.49 (3H, s), 1.45 (9H, s), 1.25 (3H, t, J=7.6 Hz); $^{13}$C NMR (100 MHz, CDCl$_3$): δ 168.0, 167.3, 167.0, 152.7, 151.7, 146.9, 131.0, 130.9, 122.8, 117.7, 110.6, 37.1, 32.5, 20.8, 15.6, 13.4; LC-MS (negative ion mode): m/z 419, 421 (M−H)−.

Step e

HCl Salt 3-(5-Ethyl-6-methylthiopheno[2,3-d]pyrimidin-4-ylamino)-5-tert-butyl-selenophene-2-carboxamide is treated with HCl in dioxane as described in Example 1, gave the HCl salt as a pale yellow color solid, mp 258-260° C. LC-MS (positive ion mode): m/z 421, 423 (M−HCl+H)+.

Example 14

Synthesis of 3-(6-(methylthio)thiopheno[3,2-d]pyrimidin-4-ylamino)-5-tert-butyl-selenophene-2-carboxamide (Compd. 14)

Step a 6-(Methylthio)thieno[3,2-d]pyrimidin-4(3H)-one

A mixture of ethyl 3-amino-5-(methylthio)-thiophene-2-carboxylate (2 g) and formamide (20 mL) was stirred at 150-160° C. for 6 h. The reaction mixture was allowed to rt and poured into ice cold water. The solution was stirred for 15 min. and the precipitated solid was filtered, washed with ice cold water and dried to give the product as a light brown color solid (1.2 g, 61%), mp 216-218° C. $^1$H NMR (400 MHz, DMSO-d$_6$): δ 12.45 (1H, s), 8.11 (1H, s), 7.26 (1H, s), 2.68 (3H, s); LC-MS (negative ion mode): m/z 197 (M–H)$^-$.

Step b

4-Chloro-6-(methylthio)thieno[3,2-d]pyrimidine

A mixture of 6-(methylthio)thieno[3,2-d]pyrimidin-4(3H)-one (900 mg) and phosphorous oxychloride (10 mL) was refluxed for 3 h. The reaction mixture was attained to rt and poured into ice cold water and stirred for 10 min. The precipitated solid was filtered, washed with water and dried to give the product as an off-white color solid (800 mg, 81%), mp 138-140° C. $^1$H NMR (400 MHz, CDCl$_3$): δ 8.87 (1H, s), 7.25 (1H, s), 2.72 (3H, s).

Step c 3-(6-(Methylthio)thiophenono[3,2-d]pyrimidin-4-ylamino)-5-tert-butyl-selenophene-2-carboxamide The reaction of 4-chloro-6-(methylthio)thieno[3,2-d]pyrimidine with 3-amino-5-tert-butylselenophene-2-carboxamide in the presence of DMF/NaOH as described in Example 1 gave title compound as an off-white color solid, mp 260-262° C. IR (KBr) v$_{max}$ 3333, 3110, 2956, 1658, 1603, 1387, 1274, 1089, 849, 788 cm$^{-1}$; $^1$H NMR (400 MHz, CDCl$_3$): δ 11.38 (1H, s, exchangeable with D$_2$O), 8.72 (1H, s), 8.71 (1H, s), 7.21 (1H, s), 5.50 (2H, br s, exchangeable with D$_2$O), 2.67 (3H, s), 1.45 (9H, s); $^{13}$C NMR (100 MHz, CDCl$_3$): δ 168.9, 168.4, 161.1, 154.8, 152.0, 149.5, 147.5, 122.6, 121.8, 117.0, 109.4, 37.2, 32.6, 18.8; LC-MS (negative ion mode): m/z 423, 425 (M–H)$^-$.

Example 15

Synthesis of 3-(6-phenylfuro[2,3-d]pyrimidin-4-ylamino)-5-tert-butylselenophene-2-carboxamide (Compd. 15)

Step a

6-Phenylfuro[2,3-d]pyrimidin-4(3H)-one

To an ice cold solution of 2-amino-5-phenylfuran-3-carbonitrile (2.0 g) in formic acid (20 mL) was added acetic anhydride (20 mL) slowly for 10 min. The reaction mixture was stirred at 0-10° C. for 1 h and allowed to rose the temperature to 100° C. At this temperature, the mixture was stirred for 16 h and allowed to rt. The mixture was poured into ice cold water and stirred for 15 min. The precipitated solid was filtered, washed with ice cold water and dried to give the product as a brown color solid (1.6 g, 69%), mp 320-322° C. $^1$H NMR (400 MHz, DMSO-d$_6$): δ 12.64 (1H, br s), 8.14 (1H, s), 7.86 (2H, d, J=6.4 Hz), 7.30-7.59 (4H, m); LC-MS (negative ion mode): m/z 211 (M–H)$^-$.

Step b

4-Chloro-6-phenylfuro[2,3-d]pyrimidine

A mixture of 6-phenylfuro[2,3-d]pyrimidin-4(3H)-one (1.0 g) and POCl$_3$ (10 mL) was stirred at 55-65° C. for 3 h. The reaction mixture was poured into ice cold water and stirred for 10 min. The solution was extracted with chloroform (3×100 mL) and the combined chloroform layer was washed with aq. NaHCO$_3$ solution, water, brine and dried over sodium sulfate. The residue was chromatographed over silica gel column using hexane-EtOAc (95:5) as eluents to give the product as a white color solid (800 mg, 74%), mp 136-138° C. $^1$H NMR (400 MHz, CDCl$_3$): δ 8.74 (1H, s), 7.90-7.93 (2H, m), 7.45-7.54 (3H, m), 7.08 (1H, s).

Step c 3-(6-phenylfuro[2,3-d]pyrimidin-4-ylamino)-5-tert-butylselenophene-2-carboxamide The reaction of 4-chloro-6-phenylfuro[2,3-d]pyrimidine with 3-amino-5-tert-butylselenophene-2-carboxamide in the presence of DMF/NaOH as described in Example 1 gave title compound as a pale yellow color solid, mp 280-282° C. IR (KBr) v. 3326, 3188, 2953, 1624, 1386, 1358, 1324, 1283, 1150, 1089, 1016, 921, 822, 778, 755 cm$^{-1}$; $^1$H NMR (400 MHz, DMSO-d$_6$): δ 11.94 (1H, s, exchangeable with D$_2$O), 8.53 (1H, s), 8.50 (1H, s), 7.96 (2H, d, J=7.2 Hz), 7.43-7.55 (5H, m), 7.32 (1H, s), 1.40 (9H, s); $^{13}$C NMR (100 MHz, DMSO-d$_6$): δ 167.4, 167.1, 166.2, 153.3, 152.5, 152.3, 144.7, 129.3, 129.1, 128.6, 124.7, 121.1, 113.3, 104.4, 97.4, 36.4, 32.2; LC-MS (negative ion mode): m/z 437, 439 (M–H)$^-$.

Example 16

Synthesis of 3-(6-tert-butylfuro[2,3-d]pyrimidin-4-ylamino)-5-tert-butylselenophene-2-carboxamide (Compd. 16)

Step a 6-tert-Butylfuro[2,3-d]pyrimidin-4(3H)-one

To an ice cold solution of 5-tert-butyl-2-aminofuran-3-carbonitrile (2.0 g) in formic acid (20 mL) was added acetic anhydride (20 mL) slowly for 10 min. The reaction mixture was stirred at 0-10° C. for 1 h and allowed to rose the temperature to 100° C. At this temperature, the mixture was stirred for 16 h and allowed to rt. The mixture was poured into ice cold water and stirred for 15 min. The solution was extracted with ethyl acetate (3×100 mL) and the combined organic layer was washed with water, brine and dread over sodium sulfate. The solution was filtered and evaporated the solvent. The residue was triturate with hexane and the solid was filtered and dried to give the product as a brown color solid (1.1 g, 47%), mp 198-200° C. 1H NMR (400 MHz, DMSO-d$_6$): δ 12.46 (1H, br s), 8.31 (1H, s), 6.53 (H, s), 1.30 (9H, s); LC-MS (negative ion mode): m/z 191 (M–H)$^-$.

Step b 6-tert-Butyl-4-chlorofuro[2,3-d]pyrimidine

A mixture of 6-tert-butylfuro[2,3-d]pyrimidin-4(3H)-one (1.0 g) and POCl$_3$ (10 mL) was stirred at 55-65° C. for 3 h. The reaction mixture was poured into ice cold water and stirred for 10 min. The solution was extracted with chloroform (3×100 mL) and the combined chloroform layer was washed with aq. NaHCO$_3$ solution, water, brine and dried over sodium sulfate. The solution was filtered and evaporated the solvent. The residue was chromatographed over silica gel column using hexane-EtOAc (90:10) as eluents to give the product as a white color solid (800 mg, 73%), mp 72-74° C. $^1$H NMR (400 MHz, CDCl$_3$): δ 8.69 (1H, s), 6.48 (1H, s), 1.42 (9H, s).

Step c 3-(6-tert-Butylfuro[2,3-d]pyrimidin-4-ylamino)-5-tert-butylselenophene-2-carboxamide The reaction of 4-chloro-6-tert-butylfuro[2,3-d]pyrimidine with 3-amino-5-tert-butylselenophene-2-carboxamide in the presence of DMF/NaOH as described in Example 1 gave title compound as an off-white color solid, mp 288-290° C. IR (KBr) v$_{max}$ 3491, 3325 2964, 1593, 1388, 1354, 1314, 1287, 1149, 1119, 1089, 936, 806, 773 cm$^{-1}$; $^1$H NMR (400 MHz, DMSO-d$_6$): δ 10.80 (1H, s, exchangeable with D$_2$O), 8.46 (2H, s), 7.48 (2H, br s, exchangeable with D$_2$O), 6.41 (1H, s), 1.39 (9H, s), 1.36 (9H, s); $^{13}$C NMR (100 MHz, DMSO-d$_6$): δ 167.4, 167.1, 166.0, 164.1, 152.6, 152.3, 144.9, 121.0, 113.1, 103.3, 94.8, 36.4, 32.7, 32.2, 28.23; LC-MS (negative ion mode): m/z 417, 419 (M–H)$^-$.

Example 17

Synthesis of methyl 4-(5,6-dimethyl-7H-pyrrolo[2,3-d]pyrimidin-4-ylamino)-5-methylselenophene-2-carboxylate (Compd. 17)

The reaction of 2-amino-4,5-dimethyl-1H-pyrrole-3-carbonitrile with dimethylformamide-dimethylacetal and methyl 4-amino-5-methylselenophene-2-carboxylate as described in the example 10, gave title compound as a pale brown color solid, mp 238-240° C. $^1$H NMR (400 MHz, CDCl$_3$): δ 8.74 (1H, br s, exchangeable with D$_2$O), 7.95 (1H, s), 7.37 (1H, s), 3.86 (3H, s), 2.43 (3H, s), 2.32 (3H, s), 2.25 (3H, s); LC-MS (positive ion mode): m/z 363, 365 (M+H)$^+$.

Example 18

Synthesis of 3-(6-tert-butylselenopheno[3,2-d]pyrimidin-4-ylamino)-5-tert-butylselenophene-2-carboxamide (Compd. 18)

Step a 6-tert-Butylselenopheno[3,2-d]pyrimidin-4(3H)-one

To a solution of 3-amino-5-(tert-butyl)selenophene-2-carboxamide (1 g) in formic acid (10 mL) was added concentrated sulfuric acid (5 mL) slowly for 10 min at rt. The mixture was refluxed for 1.5 h and allowed to rt. The mixture was poured into ice cold water and basified with ammonia solution. The solution was extracted with chloroform (3×200 mL) and the combined chloroform layer was washed with water, brine and dried over sodium sulfate. The solution was filtered and evaporated the solvent to give the product as a yellow color solid (900 mg, 80%), mp 240-242° C. $^1$H NMR (400 MHz, CDCl$_3$): δ 12.61 (1H, br s), 8.16 (1H, s), 7.34 (1H, s), 1.46 (9H, s); LC-MS (negative ion mode): m/z 253, 255 (M–H)$^-$.

Step b

4-Chloro-6-tert-butylselenopheno[3,2-d]pyrimidine

A mixture of 6-(tert-butyl)-3-hydroselenopheno[3,2-d]pyrimidin-4-one (550 mg), thionyl chloride (6 mL) and catalytic amount of DMF (0.5 mL) was refluxed for 2 h. Solvents were removed under vacuum and the mixture was diluted with chloroform. Again the solvents were removed under vacuum and this procedure repeated twice (yellow color solid). The residue was diluted with ice cold water and basified with 10% aqueous sodium bicarbonate. The solution was extracted with chloroform (3×100 mL) and the combined chloroform layer was washed with water, brine and dried over sodium sulfate. The solution was filtered and evaporated the solvent to give the product as a pale yellow color solid (520 mg, 88%), mp 78-80° C. $^1$H NMR (400 MHz, CDCl$_3$): δ 8.91 (1H, s), 7.51 (1H, s), 1.49 (9H, s).

Step c 3-(6-tert-Butylselenopheno[3,2-d]pyrimidin-4-ylamino)-5-tert-butylselenophene-2-carboxamide The reaction of 4-chloro-6-(tert-butyl)selenopheno[3,2-d]pyrimidine with 3-amino-5-tert-butylselenophene-2-carboxamide in the presence of DMF/NaOH as described in Example 1 gave title compound as a white color solid, mp 260-262° C. IR (KBr) v$_{max}$ 3439, 3173, 2960, 1666, 1605, 1564, 1503, 1458, 1381, 1330, 1244, 1086, 1038, 848, 773 cm$^{-1}$; $^1$H NMR (400 MHz, CDCl$_3$): δ 11.32 (1H, s, exchangeable with D$_2$O), 8.75 (1H, s), 8.73 (1H, s), 7.37 (1H, s), 5.34 (2H, br s, exchangeable with D$_2$O), 1.47 (9H, s), 1.46 (9H, s); $^{13}$C NMR (100 MHz, CDCl$_3$): δ 171.9, 168.8, 168.5, 164.4, 154.8, 147.8, 122.7, 121.6, 118.4, 108.9, 37.3, 37.1, 32.5, 32.4; LC-MS (positive ion mode): m/z 481, 483, 485 (M+H)$^+$.

Step d

HCl Salt 3-(6-tert-Butylselenopheno[3,2-d]pyrimidin-4-ylamino)-5-tert-butylseleno-phene-2-carboxamide is treated with HCl in dioxane as described in Example 1, gave the HCl salt as a yellow color solid, mp 212-214° C. LC-MS (positive ion mode): m/z 481, 483, 485 (M–HCl+H)$^+$.

Example 19

Synthesis of 3-(5-ethyl-6-methylselenopheno[2,3-d]pyrimidin-4-ylamino)-5-tert-butylselenophene-2-carboxamide (Compd. 19)

Step a

2-Amino-4-ethyl-5-methylselenophene-3-carbonitrile

To a solution of diethyl ketone (2 g, 23.24 mmol) in ethanol (20 mL) was added sequentially malononitrile (1.53 g, 23.24 mmol), selenium powder (1.86 g, 23.24 mmol) and triethyl amine (24.24 mL, 232.5 mmol) at rt. The reaction mixture was refluxed for 2 h. The reaction mixture was allowed to rt and powdered into ice cold water. The solution was stirred for 15 min and extracted with ethyl acetate (3×100 mL). The combined EtOAc layer was washed with water, brine and dried over sodium sulfate. The residue was chromatographed over silica gel column using hexane-ethyl acetate (95:5) as eluents to give the product as an off-white color solid (3.0 g, 60%), mp 126-128° C. $^1$H NMR (400 MHz, CDCl$_3$): δ 4.95 (2H, br s), 2.45 (2H, q, J=7.6 Hz), 2.26 (3H, s), 1.14 (3H, t, J=7.6 Hz); $^{13}$C NMR (100 MHz, CDCl$_3$): δ 164.2, 137.2, 121.5, 116.6, 91.7, 22.0, 14.3, 14.2; LC-MS (negative ion mode): m/z 211, 213 (M−H)⁻.

Step b

5-Ethyl-6-methylselenopheno[2,3-d]pyrimidin-4(3H)-one

To an ice cold solution of 2-amino-4-ethyl-5-methylselenophene-3-carbonitrile (0.4 g) in formic acid (5 mL) was added concentrated sulfuric acid (2 mL) slowly for 10 min. The mixture was stirred at 90-100° C. for 1 h and allowed to rt. The mixture was poured into ice cold water and stirred for 15 min. The precipitated solid was filtered, washed with ice cold water and dried to give the product as a brown color solid (320 mg, 71%), mp 180-182° C. $^1$H NMR (400 MHz, CDCl$_3$): δ 12.14 (1H, br s), 7.94 (1lH, s), 2.98 (2H, q, J=7.4 Hz), 2.52 (3H, s), 1.18 (3H, t, J=7.4 Hz); LC-MS (negative ion mode): m/z 239, 241 (M−H)⁻.

Step c

4-Chloro-5-ethyl-6-methylselenopheno[2,3-d]pyrimidine

A mixture of 5-ethyl-6-methylselenopheno[2,3-d]pyrimidin-4(3H)-one (300 mg) and phosphorous oxychloride (5 mL) was refluxed for 1 h. The reaction mixture was attained to rt and poured into ice cold water and stirred for 10 min. The precipitated solid was filtered, washed with water and dried to give the product as a brown color solid (260 mg, 81%), mp 58-60° C. $^1$H NMR (400 MHz, CDCl$_3$): δ 8.68 (1H, s), 3.06 (2H, q, J=7.5 Hz), 2.62 (3H, s), 1.23 (3H, t, J=7.4 Hz).

Step d

3-(5-Ethyl-6-methylselenopheno[2,3-d]pyrimidin-4-ylamino)-5-tert-butylselenophene-2-carboxamide The reaction of 4-chloro-5-ethyl-6-methylselenopheno[2,3-d]pyrimidine with 3-amino-5-tert-butylselenophene-2-carboxamide in the presence of DMF/NaOH as described in Example 1 gave title compound as a pale yellow color solid, mp 258-260° C. IR (KBr) ν$_{max}$ 3321, 3149, 2960, 1666, 1582, 1384, 1356, 1224, 1187, 1129, 1042, 1020, 925, 838, 810 cm⁻¹; $^1$H NMR (400 MHz, CDCl$_3$): δ 10.96 (1H, s, exchangeable with D$_2$O), 8.51 (1H, s), 8.49 (1H, s), 5.44 (2H, br s, exchangeable with D$_2$O), 3.13 (2H, q, J=7.6 Hz), 2.57 (3H, s), 1.44 (9H, s), 1.24 (3H, t, J=7.6 Hz); $^{13}$C NMR (100 MHz, CDCl$_3$): δ 172.1, 167.9, 167.1, 153.4, 151.2, 146.9, 135.6, 133.4, 122.8, 120.8, 110.6, 37.0, 32.6, 21.8, 15.8, 15.3; LC-MS (negative ion mode): m/z 465, 467, 469 (M−H)⁻.

Step e

HCl Salt 3-(5-Ethyl-6-methylselenopheno[2,3-d]pyrimidin-4-ylamino)-5-tert-butylselenophene-2-carboxamide is treated with HCl in dioxane as described in Example 1, gave the HCl salt as a pale yellow color solid, mp 278-280° C. LC-MS (positive ion mode): m/z 467, 469, 471 (M−HCl+H)⁺.

Example 20

Synthesis of 3-(2-(methylthio)thiazolo[4,5-d]pyrimidin-7-ylamino)-5-tert-butylseleno-phene-2-carboxamide (Compd. 20)

Step a

2-(Methylthio)thiazolo[4,5-d]pyrimdin-7-(6H)-one

To a solution of 4-amino-2-(methylthio)thiazole-5-carbonitrile (800 mg) in formic acid (8 mL) was added concentrated sulfuric acid (3.2 mL) dropwise for 15 min. The reaction mixture was stirred at 90-100° C. for 1 h and allowed to rt. The reaction mixture was poured into ice cooled water and stirred for 15 min. The precipitated solid was filtered, washed with water and dried to give the product as a white color solid (820 mg, 88%), mp 260-262° C. $^1$H NMR (400 MHz, DMSO-d$_6$): δ 12.83 (1H, br s), 8.25 (1H, s), 2.80 (3H, s); LC-MS (negative ion mode): m/z 198 (M−H)⁻.

Step b

7-Chloro-2-(methylthio)thiazolo[4,5-d]pyrimidine

A mixture of 2-(methylthio)thiazolo[4,5-d]pyrimdin-7-(6H)-one (800 mg) and phosphorous oxychloride (8 mL) was refluxed for 2 h. Solvents were removed under vacuum and the mixture was diluted with chloroform. Again the solvents were removed under vacuum and this procedure repeated twice (yellow color solid). The residue was diluted with ice cold water and basified with 10% aqueous sodium bicarbonate. The solution was extracted with chloroform (3×100 mL) and the combined chloroform layer was washed with water, brine and dried over sodium sulfate. The solution was filtered and evaporated the solvent. The residue was chromatographed over silica gel column using hexane-ethyl acetate (95:5) as eluents to give the product as a white color solid (750 mg, 86%), mp 148-150° C. $^1$H NMR (400 MHz, CDCl$_3$): δ 8.95 (1H, s), 2.90 (3H, s); LC-MS (positive ion mode): m/z 218, 220 (M+H)⁺.

Step c

3-(2-(Methylthio)thiazolo[4,5-d]pyrimidin-7-ylamino)-5-tert-butyl selenophene-2-carboxamide The reaction of 7-chloro-2-(methylthio)thiazolo[4,5-d]pyrimidine with 3-amino-5-tert-butylselenophene-2-carboxamide in the presence of DMF/NaOH as described in Example 1 gave title compound as a pale color solid, mp 280-282° C. $^1$H NMR (400 MHz, DMSO-d$_6$): δ 12.16 (1H, br s, exchangeable with D$_2$O), 8.77 (1H, s), 8.15 (1H, s), 7.61 (2H, br s, exchangeable with D$_2$O), 2.69 (3H, s), 1.39 (9H, s); LC-MS (positive ion mode): m/z 426, 428 (M+H)⁺.

Example 21

Synthesis of 3-(N-(6,7-dimethoxyquinazolin-4-yl)-N-methylamino)-5-tert-butylseleno-phene-2-carboxamide (Compd. 21)

To an ice cold solution of compound 1 (1.0 g, 2.30 mmol) in DMF (15 mL) was added successively iodomethane (0.144 mL, 2.30 mmol) and K$_2$CO$_3$ (0.63 g, 4.61 mmol). The reaction mixture was stirred at rt for 6 h, poured into ice cold water and stirred for 10 min. The solution was extracted with EtOAc (3×100 mL) and the combined EtOAc layer was washed water, brine and dried over sodium sulfate. The solution was filtered and evaporated the solvent. The residue was chromatographed over silica gel column using chloroform-methanol (99:1) as eluents to give the product (750 mg, 72%), which was recrystallized from chloroform-methanol as an yellow color solid, mp 256-258° C. IR (KBr) $v_{max}$ 3210, 2958, 1616, 1528, 1277, 1209, 1057, 1034, 1010, 961, 847, 812, 765 cm$^{-1}$; $^1$H NMR (400 MHz, DMSO-d$_6$): δ 8.39 (1H, br s), 8.17 (1H, s), 7.57 (1H, s), 7.52 (1H, s), 7.20 (1H, br s), 6.98 (1H, s), 3.97 (3H, s), 3.86 (3H, s), 3.71 (3H, s), 1.32 (9H, s); $^{13}$C NMR (100 MHz, DMSO-d$_6$): δ 165.3, 162.8, 153.7, 153.4, 150.4, 150.2, 148.2, 134.1, 126.1, 123.9, 112.7, 105.7, 98.4, 56.2, 55.7, 36.8, 36.0, 32.2; LC-MS (positive ion mode): m/z 447, 449 (M+H)$^+$.

Example 22

Synthesis of 3-(N-(6-(3-morpholinopropoxy)-7-methoxyquinazolin-4-yl)-N-methylamino)-5-tert-butylselenophene-2-carboxamide (Compd. 22)

Step a 3-(N-(6-(3-Morpholinopropoxy)-7-methoxyquinazolin-4-yl)-N-methylamino)-5-tert-butylselenophene-2-carboxamide To an ice cold solution of compound 3 (800 mg, 1.46 mmol) in acetone (20 mL) was added dimethyl sulfate (0.14 mL, 1.46 mmol). The reaction mixture was stirred at rt for 16 h, poured into ice cold water and stirred for 10 min. The solution was extracted with EtOAc (3×100 mL) and the combined EtOAc layer was washed water, brine and dried over sodium sulfate. The solution was filtered and evaporated the solvent. The residue was chromatographed over silica gel column using chloroform-methanol (99:1) as eluents to give the product (420 mg, 51%), which was recrystallized from chloroform-methanol as yellow color solid, mp 228-230° C. IR (KBr) v. 3424, 2955, 2851, 1616, 1277, 1116, 1055, 1013, 860, 763 cm$^{-1}$; $^1$H NMR (400 MHz, DMSO-d$_6$): δ 8.31 (1H, s), 8.17 (1H, s), 7.59 (1H, s), 7.48 (1H, s), 7.24 (1H, br s), 6.70 (1H, br s), 4.08 (2H, t, J=6.2 Hz), 3.97 (3H, s), 3.71 (3H, s), 3.57 (4H, br s), 2.45 (2H, br s), 2.38 (4H, br s), 1.91-1.96 (2H, m), 1.32 (9H, s); LC-MS (positive ion mode): m/z 560, 562 (M+H)$^+$.

Step b

HCl Salt 3-(N-(6-(3-Morpholinopropoxy)-7-methoxyquinazolin-4-yl)-N-methylamino)-5-tert-butylselenophene-2-carboxamide is treated with HCl in dioxane as described in Example 1, gave the HCl salt as a pale yellow color solid, mp 254-256° C. LC-MS (positive ion mode): m/z 560, 562 (M+H−HCl)$^+$.

Example 23

Synthesis of 3-(N-(6-(3-morpholinopropoxy)-7-methoxyquinazolin-4-yl)-N-(2-chloroethyl)amino)-5-tert-butylselenophene-2-carboxamide (Compd. 23)

Step a 3-(N-(6-(3-Morpholinopropoxy)-7-methoxyquinazolin-4-yl)-N-(2-chloroethyl)amino)-5-tert-butylselenophene-2-carboxamide To a solution of compound 3 (800 mg, 1.46 mmol) in DMF (15 mL) was added potassium carbonate (400 ng, 2.92 mmol), followed by dropwise addition of bromochloroethane (0.122 g, 1.46 mmol) for 5 min at rt. The reaction mixture was stirred for 16 h, poured into ice cold water and stirred for 10 min. The solution was extracted with chloroform (3×100 mL) and the combined chloroform layer was washed water, brine and dried over sodium sulfate. The solution was filtered and evaporated the solvent. The residue was chromatographed over silica gel column using chloroform-methanol (96:4) as eluents to give the product as an yellow color solid, which was recrystallized from chloroform-hexane (450 mg, 51%), mp 198-200° C. $^1$H NMR (400 MHz, CDCl$_3$): δ 8.38 (1H, br s), 7.82 (1H, s), 7.77 (1H, s), 7.39 (1H, s), 6.55 (1H, s), 5.66 (1H, br s), 4.30 (2H, br s), 4.17 (2H, t, J=6.4 Hz), 3.98 (3H, s), 3.86 (2H, t, J=5.6 Hz), 3.72 (4H, br s), 2.52 (2H, t, J=6.6 Hz), 2.47 (4H, br s), 2.04-2.07 (2H, m), 1.38 (9H, s); $^{13}$C NMR (100 MHz, DMSO-d$_6$): δ 164.4, 162.3, 153.0, 152.5, 149.8, 149.4, 146.8, 131.8, 125.6, 123.0, 112.0, 106.4, 97.7, 66.1, 65.4, 55.7, 54.0, 52.6, 49.1, 41.7, 35.3, 31.4, 24.9; LC-MS (positive ion mode): m/z 608, 610, 612 (M+H)$^+$.

Step b

HCl Salt 3-(N-(6-(3-Morpholinopropoxy)-7-methoxyquinazolin-4-yl)-N-(2-chloroethyl)amino)-5-tert-butylselenophene-2-carboxamide is treated with HCl in dioxane as described in Example 1, gave the HCl salt as a pale yellow color solid, mp 190-192° C.; LC-MS (positive ion mode): m/z 608, 610, 612 (M−HCl+H)$^+$.

Example 24

Synthesis of 3-(6,7-dimethoxy-2-methylquinazolin-4-ylamino)-5-tert-butylselenophene-2-carboxamide (Compd. 24)

Step a 6,7-Dimethyl-2-methylquinazolin-4(3H)-one

Dry HCl gas was passed (until the clear solution observed) to a solution of methyl 2-amino-4,5-dimethoxybenzoate (3.0 g, 14.21 mmol) in acetonitrile (72 mL) for 30 min at rt. The reaction mixture was refluxed for 3 h and attained to rt. The solid precipitated was filtered and the solid was dissolved in water. The solution was neutralized with 10% aqueous NaHCO$_3$ and the precipitated solid was filtered, washed with ice cold water and dried to give the product as an off-white color solid (2.5 g, 80%), mp 310-312° C. $^1$H NMR (400 MHz, DMSO-d$_6$): δ 7.40 (1H, s), 7.06 (1H, s), 3.88 (3H, s), 3.85 (3H, s), 2.31 (3H, s); LC-MS (positive ion mode): m/z 221 (M+H)$^+$.

Step b

4-Chloro-6,7-dimethoxy-2-methylquinazoline

A mixture of 6,7-dimethoxy-2-methylquinazolin-4(3H)-one (1.0 mg) and phosphorous oxychloride (20 mL) was refluxed for 3 h. The reaction mixture was attained to rt and poured into ice cold water and stirred for 10 min. The solution was extracted with chloroform (3×100 mL) and the combined CHCl$_3$ layer was washed water, brine and dried over sodium sulfate. The solution was filtered and evaporated the solvent to give the product as a yellow color solid (1.0 g, 92%), mp 182-184° C. $^1$H NMR (400 MHz, CDCl$_3$): δ 7.36 (1H, s), 7.30

(1H, s), 4.06 (6H, s), 2.81 (3H, s); LC-MS (positive ion mode): m/z 239, 241 (M+H)+.

Step c 3-(6,7-Dimethoxy-2-methylquinazolin-4-ylamino)-5-tert-butylselenophene-2-carboxamide The reaction of 4-chloro-6,7-dimethoxy-2-methylquinazoline with 3-amino-5-tert-butylselenophene-2-carboxamide in the presence of DMF/NaOH as described in Example 1 gave title compound as an off-white color solid, mp 266-268° C. $^1$H NMR (400 MHz, CDCl$_3$): δ 11.95 (1H, br s, exchangeable with D$_2$O), 8.97 (1H, s), 7.32 (1H, s), 7.19 (1H, s), 5.38 (2H, br s, exchangeable with D$_2$O), 4.08 (3H, s), 4.01 (3H, s), 2.70 (3H, s), 1.47 (9H, s); $^{13}$C NMR (100 MHz, CDCl$_3$): δ 168.63, 168.60, 162.1, 154.8, 154.5, 149.2, 148.2, 148.1, 121.9, 109.0, 107.4, 107.1, 100.1, 56.2, 56.1, 37.1, 32.5, 26.3; LC-MS (negative ion mode): m/z 445, 447 (M−H)−.

Step d

HCl Salt 3-(6,7-Dimethoxy-2-methylquinazolin-4-ylamino)-5-tert-butylselenophene-2-carboxamide is treated with HCl in dioxane as described in Example 1, gave the HCl salt as a pale yellow color solid, mp 282-284° C. LC-MS (negative ion mode): m/z 445, 447 (M−HCl−H)−.

Example 25

Synthesis of methyl 4-(6,7-dimethoxy-2-methylquinazolin-4-ylamino)-5-methylselenophene-2-carboxylate (Compd. 25)

Step a

Methyl 4-(6,7-dimethoxy-2-methylquinazolin-4-ylamino)-5-methylselenophene-2-carboxylate To a solution of 4-chloro-6,7-dimethoxy-2-methylquinazoline (From example 24; 700 mg, 2.93 mmol) in isopropanol (20 mL) was added 4-amino-5-methylselenophene-2-carboxylate (1.3 g, 5.8 mmol) at rt and the mixture was stirred at rt for 16 h. The mixture was poured into ice cooled water and stirred for 10 min. The solution was extracted with EtOAc (3×100 mL) and the combined layer was washed with water, brine and dried over sodium sulfate. The solution was filtered and evaporated the solvent. The residue was chromatographed over silica gel column using chloroform-methanol (98:2) as eluents to give the product (700 mg, 57%) as a brown color solid, mp 200-204° C. $^1$H NMR (400 MHz, CDCl$_3$): δ 8.18 (1H, s), 7.19 (1H, s), 7.00 (1H, s), 3.98 (3H, s), 3.92 (3H, s), 3.85 (3H, s), 2.58 (3H, s), 2.46 (3H, s); $^{13}$C NMR (100 MHz, CDCl$_3$): δ 163.5, 162.8, 156.9, 154.8, 148.7, 148.2, 144.0, 135.3, 135.1, 131.8, 107.3, 106.4, 99.8, 56.2, 56.1, 52.2, 26.2, 15.5; LC-MS (positive ion mode): m/z 420, 422 (M+H)+.

Step b

HCl Salt

Methyl 4-(6,7-dimethoxy-2-methylquinazolin-4-ylamino)-5-methylselenophene-2-carboxylate is treated with HCl in dioxane as described in Example 1, gave the HCl salt as a pale yellow color solid, mp 276-280° C. LC-MS (positive ion mode): m/z 420, 422 (M−HCl+H)+.

Example 26

Synthesis of 3-(6-(3-morpholinopropoxy)-7-methoxy-2-methylquinazolin-4-ylamino)-5-tert-butylselenophene-2-carboxamide (Compd. 26)

Step a 6-(3-Morpholinopropoxy)-7-methoxy-2-methylquinazolin-4(3H)-one

Dry HCl gas was passed (until the clear solution observed) to a solution of methyl 5-(3-morpholinopropoxy)-2-amino-4-methoxy-benzoate (1.0 g, 3.0 mmol) in acetonitrile (16 mL) for 30 min at rt. The reaction mixture was refluxed for 3 h and attained to rt. The solution was poured into ice cooled water and basified with ammonia solution. The solution was extracted with EtOAc (3×100 mL) and the combined EtOAc layer was washed water, brine and dried over sodium sulfate. The solution was filtered and evaporated the solvent to give the product as an off-white color solid (1.0 g, 98%), mp 236-238° C. $^1$H NMR (400 MHz, CDCl$_3$): δ 11.60 (1H, br s), 7.59 (1H, s), 7.08 (1H, s), 4.23 (2H, t, J=6.6 Hz), 3.97 (3H, s), 3.73 (4H, t, J=4.6 Hz), 2.56 (2H, t, J=7.0 Hz), 2.56 (3H, s), 2.48 (4H, t, J=4.4 Hz), 2.09 (2H, pentet, J=6.8 Hz); LC-MS (positive ion mode): m/z 334 (M+H)+.

Step b 6-(3-Morpholinopropoxy)-4-chloro-7-methoxy-2-methylquinazoline

A mixture of 6-(3-morpholinopropoxy)-7-methoxy-2-methylquinazolin-4(3H)-one (600 mg), thionyl chloride (20 mL) and DMF (0.5 mL) was refluxed for 3 h. The reaction mixture was attained to rt and poured into ice cold water and stirred for 10 min. The solution was basified with ammonia solution and extracted with chloroform (3×100 mL). The combined CHCl$_3$ layer was washed water, brine and dried over sodium sulfate. The solution was filtered and evaporated the solvent to give the product as a yellow color solid (500 mg, 79%), mp 116-118° C. $^1$H NMR (400 MHz, CDCl$_3$): δ 7.36 (1H, s), 7.25 (1H, s), 4.25 (2H, t, J=6.6 Hz), 4.03 (3H, s), 3.73 (4H, t, J=4.6 Hz), 2.79 (3H, s), 2.58 (2H, t, J=7.2 Hz), 2.49 (4H, t, J=4.4 Hz), 2.12 (2H, pentet, J=6.8 Hz); LC-MS (positive ion mode): m/z 352, 354 (M+H)±.

Step c 3-(6-(3-Morpholinopropoxy)-7-methoxy-2-methylquinazolin-4-ylamino)-5-tert-butylselenophene-2-carboxamide The reaction of 6-(3-morpholinopropoxy)-4-chloro-7-methoxy-2-methylquinazoline with 3-amino-5-tert-butylselenophene-2-carboxamide in the presence of DMF/NaOH as described in Example 1 gave title compound as a brown color solid, mp 204-206° C. $^1$H NMR (400 MHz, CDCl$_3$): δ 11.92 (1H, br s), 8.95 (1H, s), 7.34 (1H, s), 7.18 (1H, s), 5.37 (2H, br s), 4.29 (2H, t, J=6.0 Hz), 3.98 (3H, s), 3.73 (4H, t, J=4.4 Hz), 2.70 (3H, s), 2.61 (2H, t, J=7.2 Hz), 2.50 (4H, br s), 2.11-2.14 (2H, m), 1.47 (9H, s); LC-MS (positive ion mode): m/z 560, 562 (M+H)+.

Step d

HCl Salt 3-(6-(3-Morpholinopropoxy)-7-methoxy-2-methylquinazolin-4-ylamino)-5-tert-butylselenophene-2-carboxamide is treated with HCl in dioxane as described in Example 1, gave the HCl salt as a pale yellow color solid, mp 236-238° C.

Example 27

Synthesis of (3-ethynylphenyl)-5,6,7,8-tetrahydropyrimidino[5',6'-5,4]selenopheno[2,3-c]pyridin4-ylamine (Compd. 27)

Step a 2-(Chloromethyl)-6,7-dimethoxyluinazolin-4-(3H)-one

Dry HCl gas was passed (until the clear solution observed) to a solution of methyl 2-amino-4,5-dimethoxybenzoate (1.0 g, 4.73 mmol) in chloroacetonitrile (34 mL) for 30 min at rt. The reaction mixture was refluxed for 1 h and attained to rt. The solid precipitated was filtered and the solid was dissolved in water. The solution was neutralized with 10% aqueous $NaHCO_3$ and the precipitated solid was filtered, washed with ice cold water and dried to give the product as an off-white color solid (950 mg, 79%), mp 268-272° C. $^1$H NMR (400 MHz, $CDCl_3$): δ 12.41 (1H, s), 7.45 (1H, s), 7.17 (1H, s), 4.52 (2H, s), 3.91 (3H, s), 3.88 (3H, s); LC-MS (positive ion mode): m/z 277, 279 (M+Na)$^+$.

Step b 2-((Dimethylamino)methyl)-6,7-dimethoxyquinazolin-4-(3H)-one

To a solution of 2-(chloromethyl)-6,7-dimethoxyluinazolin-4-(3H)-one (100 mg, 0.392 mmol) in DMF (5 mL) was added dimethylamine (0.13 mL, 1.176 mmol) at rt. The reaction mixture was stirred at 70-80° C. for 2 h and allowed to rt. The reaction mixture was poured into ice cooled water and extracted with chloroform (3×200 mL). The combined organic layer was washed with water, brine and dried over sodium sulfate. The solution was filtered and evaporated the solvent to give the product as an off-white color solid (80 mg, 78%), mp 210-212° C. $^1$H NMR (400 MHz, $CDCl_3$): δ 7.61 (1H, s), 7.08 (1H, s), 4.00 (3H, s), 3.99 (3H, s), 3.50 (2H, s), 2.37 (6H, s); LC-MS (positive ion mode): m/z 264 (M+H)$^+$.

Step c (4-Chloro-6,7-dimethoxyquinazolin-2-yl)-N,N-dimethylmethanamine

A mixture of 2-((dimethylamino)methyl)-6,7-dimethoxyquinazolin-4-(3H)-one (100 mg) and phosphorous oxychloride (10 mL) was refluxed for 2 h. Excess of $POCl_3$ was evaporated under vacuum and the reaction mixture was attained to rt. The mixture was poured into ice cold water and basified with aqueous ammonia solution. The solution was extracted with chloroform (3×100 mL) and the combined $CHCl_3$ layer was washed water, brine and dried over sodium sulfate. The solution was filtered and evaporated the solvent to give the product as an off-white color solid (100 mg, 93%), mp 78-80° C. $^1$H NMR (400 MHz, $CDCl_3$): δ 7.41 (1H, s), 7.38 (1H, s), 4.05 (6H, s), 3.82 (2H, s), 2.42 (6H, s); LC-MS (positive ion mode): m/z 282, 284 (M+H)$^+$.

Step d (3-Ethynylphenyl)-5,6,7,8-tetrahydropyrimidino[5',6'-5,4]selenopheno[2,3-c]pyridin4-ylamine The reaction of (4-chloro-6,7-dimethoxyquinazolin-2-yl)-N,N-dimethylmethanamine with 3-amino-5-tert-butylselenophene-2-carboxamide in the presence of DMF/NaOH as described in Example 1 gave title compound as an off-white color solid, mp 186-190° C. $^1$H NMR (400 MHz, $CDCl_3$): δ 12.02 (1H, s, exchangeable with $D_2O$), 9.03 (1H, s), 7.32 (1H, s), 7.31 (1H, s), 5.60 (2H, s, exchangeable with $D_2O$), 4.07 (3H, s), 4.01 (3H, s), 3.73 (2H, s), 2.44 (6H, s), 1.46 (9H, s); $^{13}$C NMR (100 MHz, $CDCl_3$): δ 168.7, 168.6, 161.8, 154.7, 154.5, 149.5, 148.2, 148.1, 122.1, 109.0, 108.0, 107.7, 100.0, 66.6, 56.2, 56.1, 45.9, 37.1, 32.5; LC-MS (positive ion mode): m/z 490, 492 (M+H)$^+$.

Step e

HCl Salt (3-Ethynylphenyl)-5,6,7,8-tetrahydropyrimidino[5',6'-5,4]selenopheno[2,3-c]pyridin4-ylamine is treated with HCl in dioxane as described in Example 1, gave the HCl salt as a pale yellow color solid, mp 226-228° C. LC-MS (positive ion mode): m/z 490, 492 (M−HCl+H)$^+$.

Example 28

Synthesis of 3-(2-(4-chlorophenyl)-6,7-dimethoxyquinazolin-4-ylamino)-5-tert-butylselenophene-2-carboxamide (Compd. 28)

Step a 2-((4-Chlorophenyl)carbonylamino)-4,5-dimethoxybenzamide

To a solution of 2-amino-4,5-dimethoxybenzamide (2.0 g, 10.47 mmol) in THF (15 mL) and triethyl amine (3 mL, 20.91 mol) was added solution of 4-chlorobenzoyl chloride (2.2 g, 12.57 mol) in THF (5.0 mL) at rt for 10 min. The reaction mixture was stirred at rt 16 h. The solution was poured into ice cold water and stirred for 10 min. The separated solid was filtered, washed with ice cold water and dried to the product as a pale yellow color solid (2.9 g, 85%), mp 120-122° C. $^1$H NMR (400 MHz, DMSO-$d_6$): δ 13.38 (1H, s), 8.48 (1H, br s), 8.33 (1H, br s), 7.94 (2H, d, J=8.0 Hz), 7.66 (1H, s), 7.65 (2H, d, J=8.0 Hz), 7.46 (1H, s), 3.84 (3H, s), 3.81 (3H, s); LC-MS (negative ion mode): m/z 333, 335 (M−H)$^−$.

Step b 2-(4-Chlorophenyl)-6,7-dimethoxyquinazolin-4(3H)-one

To a solution of 2-((4-chlorophenyl)carbonylamino)-4,5-dimethoxybenzamide (1.0 g, 2.99 mmol) in ethanol (10 mL) was added aqueous NaOH solution (15 mL) at rt for 10 min. The reaction mixture was refluxed for 10 min and allowed to rt. The mixture was poured into ice cold water and stirred for 10 min EtOAc (20 mL) was added to the solution and stirred for 5 min. The separated solid was filtered, washed with ice cold water and dried to the product as a white color solid (900 mg, 95%), mp>360° C. $^1$H NMR (400 MHz, DMSO-$d_6$): δ 12.47 (1H, s), 8.19 (2H, d, J=8.6 Hz), 7.62 (2H, d, J=8.6 Hz), 7.50 (1H, s), 7.23 (1H, s), 3.94 (3H, s), 3.90 (3H, s); LC-MS (positive ion mode): m/z 317, 319 (M+H)±.

Step c

4-Chloro-2-(4-chlorophenyl)-6,7-dimethoxyquinazoline

A mixture of 2-(4-chlorophenyl)-6,7-dimethoxyquinazolin-4(3H)-one (200 mg), thionyl chloride (10 mL) and DMF (0.3 mL) was refluxed for 2 h. Solvents were removed under vacuum. The mixture was poured into ice cold water and stirred for 10 min. The solution was basified with ammonia and stirred for 5 min. The solution was extracted with chloroform (3×100 mL) and the combined chloroform layer was washed with water, brine and dried over sodium sulfate. The solution was filtered and evaporated the solvent to give the product as an yellow color solid (180 mg, 86%), mp 204-206° C. $^1$H NMR (400 MHz, DMSO-$d_6$): δ 8.47 (2H, d, J=8.4 Hz), 7.66 (2H, d, J=8.4 Hz), 7.52 (1H, s), 7.44 (1H, s), 4.08 (3H, s), 4.05 (3H, s).

Step d 3-(2-(4-Chlorophenyl)-6,7-dimethoxyquinazolin-4-ylamino)-5-tert-butylselenophene-2-carboxamide The reaction of 4-chloro-2-(4-chlorophenyl)-6,7-dimethoxyquinazoline with 3-amino-5-tert-butylselenophene-2-carboxamide in the presence of DMF/NaOH as described in Example 1 gave title compound as a white color solid, mp 268-270° C. $^1$H NMR (400 MHz, CDCl$_3$): δ 12.03 (1H, s, exchangeable with D$_2$O), 9.05 (1H, s), 8.49 (2H, d, J=8.4 Hz), 7.45 (2H, d, J=8.4 Hz), 7.37 (1H, s), 7.32 (1H, s), 5.37 (2H, s, exchangeable with D$_2$O), 4.11 (3H, s), 4.06 (3H, s), 1.52 (9H, s); $^{13}$C NMR (100 MHz, CDCl$_3$): δ 168.6, 168.5, 158.1, 155.0, 154.8, 149.9, 148.5, 148.1, 137.7, 136.0, 129.4, 128.5, 122.0, 109.3, 108.4, 108.0, 100.3, 56.3, 56.2, 37.3, 32.7; LC-MS (negative ion mode): m/z 541, 543, 545 (M-H)$^-$.

Example 29

Synthesis of 3-(6,7-dimethoxyquinazolin-4-yloxy)-5-tert-butylselenophene-2-carboxamide (Compd. 29)

To a solution of 4-chloro-6,7-dimethoxyquinazoline (200 mg, 0.89 mmol) in DMF (5 mL) was added sequentially 5-tert-butyl-3-hydroxyselenophene-2-carboxamide (220 mg, 0.89 mmol), powdered NaOH (147 mg, 3.568 mmol) and catalytic amount of KI at rt and the mixture was stirred at rt for 3 h. The mixture was poured into ice cooled water, neutralized with dil. HCl and stirred for 15 min. The precipitated solid was filtered, washed with water and dried. The crude product was chromatographed over silica gel column using chloroform-methanol (95:5) as eluents to give the product as an yellow color solid (245 mg, 63%), mp 220-224° C. $^1$H NMR (400 MHz, CDCl$_3$): δ 15.16 (1H, br s, exchangeable with D$_2$O), 13.63 (1H, br s, exchangeable with D$_2$O), 8.17 (1H, s), 7.51 (1H, s), 7.21 (1H, s), 6.87 (1H, s), 4.05 (6H, s), 1.38 (9H, s); $^{13}$C NMR (100 MHz, CDCl$_3$): δ 175.5, 172.0, 164.8, 156.6. 155.1, 150.7, 145.9, 139.9, 118.7, 113.1, 112.7, 108.4, 103.3, 56.5, 56.3, 37.1, 32.2; LC-MS (positive ion mode): m/z 434, 436 (M+H)$^+$.

Anti-Cancer Activity

Example 30

MTT Based Cell Proliferation Assay

MTT [3-(4,5-dimethylthiazol-2-yl)-2,5-diphenyltetrazolium bromide] incorporation based cell proliferation assay was performed using standard procedure. The cytotoxic efficacy of the test compounds (Compound nos. 1 to 29) was evaluated in either human lung carcinoma A549 cells or human colorectal carcinoma HT29 cells or human prostate DU145 cells or human breast carcinoma (estrogen receptor negative) MDA-MB-231 cells or human cervical carcinoma HeLa cells by MTT cell proliferation assay kit (Roche Applied Sciences, Germany). The assay was carried out according to the instructions provided by the vendor. Briefly, equal numbers of cells was plated in 96-well flat-bottomed plates and were incubated with 4-selenophenylaminopyrimidine compounds of formula (I) or gefitinib (Iressa) at different concentrations for a period of three days. Vehicle control culture wells received only a maximum of 0.5% DMSO. Thereafter, 0.5 mg/ml of MTT reagent was added to each well and the microplate was incubated further for 4 h at 37° C. in presence of 5% CO$_2$. Finally, the cells were solubilized by adding solubilizing solution and allowed to incubate at 37° C. overnight. After complete solubilization of the formazan crystals the absorbance was read at 540 nm in a microplate reader (BioRad, USA). The results (mean OD±SD) obtained from quadruplicate wells were used in calculation to determine the inhibition of cell proliferation (50% of inhibitory concentration, IC$_{50}$) of the test compounds.

The evaluation of cell proliferation inhibitory activities of the compounds was done in two phases—(1) Screening, and (2) half-maximal inhibitory concentration (IC50) determination. In the screening phase, the cells were treated with three different concentrations e.g. 1, 5 and 10 µg/ml. Thereafter, the best active test compounds were selected for IC50 determination. The cell proliferation inhibitory potentials of the test Compounds (1 to 29) at 10 µg/ml (the highest dose tested in screening assays) and the IC50s on different cell lines are summarized in Table 1. Results are presented in micromolar concentrations of the tested compounds. The cell proliferation inhibitory activities of Gefitinib (Iressa) are presented for comparison.

TABLE 1

Tumor cell Proliferation inhibitory activities of Compound 1 to Compound 29

| | Cell Proliferation Inhibition in | | |
|---|---|---|---|
| Compounds | A549 (Lung carcinoma) | DU145 (Prostate carcinoma) | HT29 (Colon carcinoma) |
| Compound 1 | IC50 at 9.08 µM | IC50 at 3.60 µM | IC50 at 5.12 µM |
| Compound 2 | IC50 at 31.08 µM | IC50 at 5.98 µM | IC50 at 19.3 µM |
| Compound 3 | IC 50 at 6.71 µM | IC50 at 7.39 µM | IC50 at 5.124 µM |
| Compound 4 | 10.37% at 17.08 µM | 9.85% at 17.08 µM | IC50 at 19.3 µM |
| Compound 5 | IC50 at 4.6 µM | IC50 at 3.9 µM | IC50 at 4.07 µM |

TABLE 1-continued

Tumor cell Proliferation inhibitory activities of Compound 1 to Compound 29

| Compounds | Cell Proliferation Inhibition in | | |
|---|---|---|---|
| | A549 (Lung carcinoma) | DU145 (Prostate carcinoma) | HT29 (Colon carcinoma) |
| Compound 6 | 5.09% at 17.9 μM | 39.7% at 17.9 μM | 86.4% at 17.9 μM |
| Compound 7 | IC50 at 6.08 μM | IC50 at 5.84 μM | 85.8% at 17.9 μM |
| Compound 8 | 7.6% at 23.5 μM | 15.67% at 23.5 μM | 81.94% at 23.5 μM |
| Compound 9 | 0.19% at 19.9 μM | IC50 at 8.51 μM | IC50 at 9.24 μM |
| Compound 10 | 10.32% at 17.97 μM | 21.38% at 17.97 μM | 6.11% at 17.97 μM |
| Compound 11 | 16% at 18.47 μM | 5.15% at 18.47 μM | 7.41% at 18.47 μM |
| Compound 12 | 7.0% at 24.3 μM | 9.18% at 24.3 μM | 6.75% at 24.3 μM |
| Compound 13 | 5.68% at 21.81 μM | 8.49% at 21.81 μM | 30.22% at 21.81 μM |
| Compound 14 | 3.54% at 21.62 μM | 7.81% at 21.62 μM | 53.49% at 21.62 μM |
| Compound 15 | 5.87% at 22.73 μM | 3.44% at 22.73 μM | 25.45% at 22.73 μM |
| Compound 16 | 1.60% at 23.81 μM | 2.81% at 23.81 μM | 20.28% at 23.81 μM |
| Compound 17 | 2.66% at 27.47 μM | 7.62% at 27.47 μM | 4.54% at 27.47 μM |
| Compound 18 | 2.18% at 19.21 μM | 7.87% at 19.21 μM | 36.4% at 19.21 μM |
| Compound 19 | 7.86% at 19.74 μM | 6.68% at 19.74 μM | 43.91% at 19.74 μM |
| Compound 20 | 1.28% at 23.42 μM | IC50 at 17.87 μM | IC50 at 9.54 μM |
| Compound 21 | IC50 at 3.59 μM | IC50 at 3.95 μM | IC50 at 3.88 μM |
| Compound 22 | 3.93% at 16.74 μM | 14.65% at 16.74 μM | 34.28% at 16.74 μM |
| Compound 23 | 3.28% at 15.48 μM | 22.44% at 15.48 μM | 40.72% at 15.48 μM |
| Compound 24 | 15.11% at 20.64 μM | 87.72% at 20.64 μM | IC50 at 10.56 μM |
| Compound 25 | 2.95% at 21.86 μM | 2.59% at 21.86 μM | 11.85% at 21.86 μM |
| Compound 26 | IC50 at 11.73 μM | IC50 at 6.78 μM | IC50 at 4.28 μM |
| Compound 27 | IC50 at 3.58 μM | IC50 at 2.97 μM | IC50 at 2.86 μM |
| Compound 28 | 9% at 18.35 μM | 10.42% at 18.35 μM | 2.69% at 18.35 μM |
| Compound 29 | 15.55% at 22.99 μM | 42.98% at 22.99 μM | 44.64% at 22.99 μM |
| Gefitinib (Iressa) | IC50 at 16.6 μM | IC50 at 18.3 μM | IC50 at 17.1 μM |

Next, based on the consistency and the highest anti-cell proliferation activities in A549, DU145 and HT-29 cells, two compounds viz. compound 21 and 27 were selected further for evaluating their inhibitory activities on cell proliferation in some other cancer cells such as human prostate DU145 cells or human breast carcinoma (estrogen receptor negative) MDA-MB-231 cells or human cervical carcinoma HeLa cells (Table 2). The cell proliferation inhibitory activities of Gefitinib (Iressa) are presented for comparison.

TABLE 2

Tumor cell proliferation inhibitory activities of selected compounds

| Compounds | Cell proliferation inhibition (IC50) in | | |
|---|---|---|---|
| | MDA-MB-231 (Breast Carcinoma) | HepG2 (Hepatocellular Carcinoma) | HeLa (Cervical Carcinoma) |
| Compound 21 | 2.86 μM | 2.33 μM | 2.97 μM |
| Compound 27 | 3.09 μM | 2.34 μM | 2.88 μM |
| Gefitinib (Iressa) | 45.40 μM | 35.53 μM | 50.12 μM |

Example 31

In Vitro Endothelial Capillary Formation Assay

In vitro capillary formation assay was performed with Human umbilical vein endothelial cells (HUVEC), cultured on 10 mg/ml basement membrane extract (BME—Cultrex®, R&D Systems, USA) bed. Four hundred microliters of Cultrex was coated at 4° C. in each well of 24-well culture plate and allowed to gel at 37° C. for 1 h. HUVECs were plated at a density of $1\times10^5$ cells per well with 400 μl of EGM-2 medium (Lonza Walkersville Inc. Walkersville, Md.). The cells were then treated with either 10 ng/ml of Human recombinant Fibroblast Growth Factor (FGF, R&D Systems, Minneapolis, Minn.)) alone or concurrently with different concentrations of Compound 27 for 16 hours. Vehicle control cultures received only 0.1% DMSO. Pictures were taken under a Nikon Eclipse TS 100 microscope equipped with a Nikon Coolpix camera. Compound 27 inhibited FGF induced capillary formation in a dose dependent manner. In contrast, FGF promoted human endothelial capillary formation in vitro (FIG. 1).

What is claimed is:
1. A selenophene compound of formula (I), a salt thereof, a solvate or hydrate thereof, or a stereoisomer thereof:

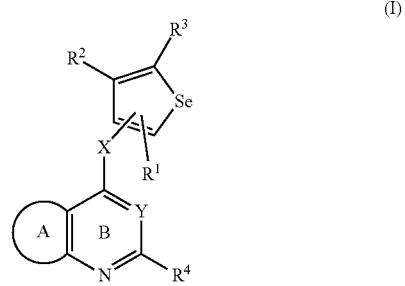

(I)

wherein:
ring A is a 6-membered aromatic fused ring, optionally containing one, two or three nitrogen atoms; a 5-membered heteroaromatic fused ring containing at least one heteroatom selected from the group consisting of sulfur, oxygen, nitrogen and selenium, with the proviso that no more than one oxygen or sulfur or selenium atom is present; or a mono- or bicyclic saturated heterocyclic fused ring having 3 to 10 carbon atoms and at least one ring member selected from the group consisting of N, O, S, SO and $SO_2$;
wherein ring A is optionally substituted by at least one group independently selected from the group consisting of hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondary-alkyl, $C_{1-6}$tertiary-alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl, and a aryl, heteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$-alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, and $C_{1-6}$alkylsulfonyl;

Y in ring B is N or C—$R^5$, wherein $R^5$ is selected from hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondary-alkyl, $C_{1-6}$tertiary-alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl;

X is attached to the C2 carbon of the selenophene ring or to the C3 carbon of the seleneophene ring, and X is selected from the group consisting of $NR^6$, O, S, S(O), and $S(O)_2$; wherein $R^6$ is selected from hydrogen, amino, $C_{1-6}$alkyl, and halo$C_{1-6}$alkyl;

$R^1$, $R^2$, $R^3$ and $R^4$ are independently selected from the group consisting of hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondary-alkyl, $C_{1-6}$tertiary-alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino $C_{1-6}$alkoxy, $C_{1-6}$alkyl amino $C_{1-6}$alkyl, di($C_{1-6}$alkyl)amino $C_{1-6}$alkyl, $C_{1-6}$alkylsulfinyl, $C_{1-6}$alkylsulfonyl, and a aryl, heteroaryl and heterocycloalkyl ring; aryl, heteroaryl and heterocycloalkyl ring optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, and $C_{1-6}$alkylsulfonyl.

2. A selenophene compound of formula (I) as claimed in claim 1, wherein X is attached to the C2 carbon of the seleneophene ring.

3. A selenophene compound of formula (I) as claimed in claim 1, wherein X is attached to the C3 carbon of the seleneophene ring.

4. A selenophene compound of formula (I) as claimed in claim 1, wherein X is $NR^6$ or O, and wherein $R^6$ is selected from the group consisting of hydrogen, amino, $C_{-1-6}$alkyl, and halo$C_{1-6}$alkyl.

5. A selenophene compound of formula (I) as claimed in claim 4, wherein the selenophene compound has a formula selected from the group consisting of Ia, Ib, Ic, and Id:

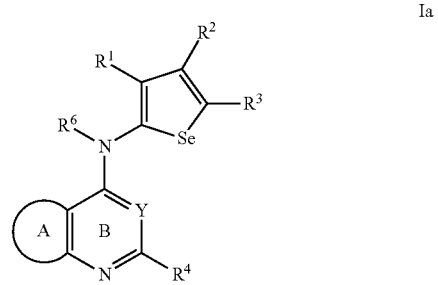

Ia

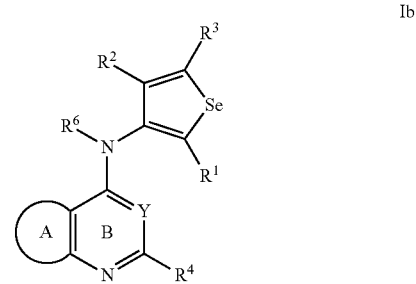

Ib

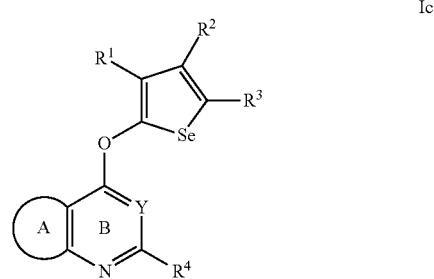

Ic

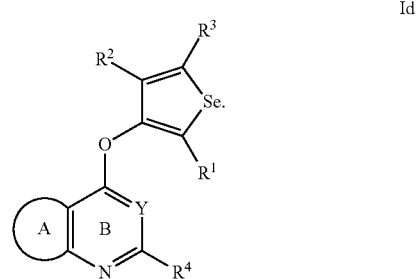

Id

6. A selenophene compound of formula (I) as claimed in claim 1, wherein Y is N or $CR^5$, and wherein the selenophene compound has a formula selected from the group consisting of Ie, If, Ig, and Ih:

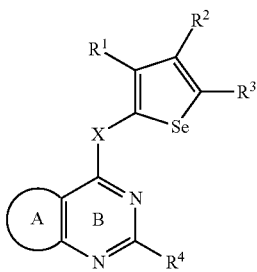
Ie

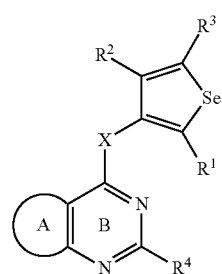
If

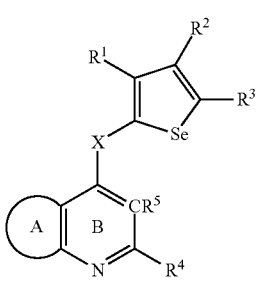
Ig

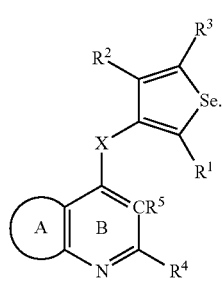
Ih

7. A selenophene compound as claimed in claim 1, wherein ring A is a 6-membered aromatic fused ring; said selenophene compound having formula (VI):

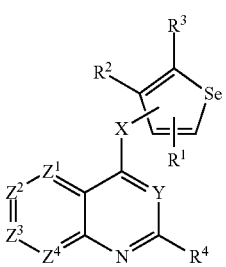
VI wherein:
$Z^1$, $Z^2$, $Z^3$, and $Z^4$ are independently selected from the group consisting of N and C—$R^7$, wherein each $R^7$ is independently selected from the group consisting of hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondary-alkyl, $C_{1-6}$tertiary-alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, $C_{1-6}$alkylsulfonyl, phenyl, benzyl, a five-membered heteroaromatic ring containing at least one heteroatom selected from the group consisting of sulfur, oxygen, nitrogen and selenium, and a group having the following formula:

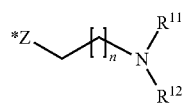

wherein n is 0 to 5;
* indicates a point of attachment to the benzene ring;
Z is selected from the group consisting of $CH_2$, O, S, or NH; and
$R^{11}$ and $R^{12}$ are independently selected from the group consisting of hydrogen, $C_{1-6}$alkyl, halo$C_{1-6}$alkyl, halo$C_{1-6}$alkoxy, and $C_{3-7}$cycloalkyl; or $R^{11}$ and $R^{12}$, together with the nitrogen atom to which they are attached, form a 5- to 7-membered heterocycloalkyl ring;
wherein phenyl and said five-membered heteroaromatic ring are optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$alkyl)amino$C_{1-6}$alkyl, $C_{1-6}$alkylsulfinyl, or $C_{1-6}$alkylsulfonyl; and
wherein said five-membered heteroaromatic ring contains no more than one oxygen or sulfur or selenium atom.

8. A selenophene compound of formula (VI) as claimed in claim 7, wherein $Z^1$, $Z^2$, $Z^3$, and $Z^4$ are each C—$R^7$.

9. A selenophene compound of formula (VI) as claimed in claim 7, wherein $Z^1$, $Z^2$, $Z^3$, and $Z^4$ are independently selected from the group consisting of N and C—$R^7$, with the proviso that at least one of $Z^1$, $Z^2$, $Z^3$, and $Z^4$ is N.

10. A selenophene compound of formula (VI) as claimed in claim 7, wherein $Z^1$, $Z^2$, $Z^3$, and $Z^4$ are independently selected from the group consisting of N and C—$R^7$, with the proviso that two of $Z^1$, $Z^2$, $Z^3$, and $Z^4$ are N.

11. A selenophene compound of formula (VI) as claimed in claim 7, wherein $Z^1$, $Z^2$, $Z^3$, and $Z^4$ are independently selected from the group consisting of N and C—$R^7$, with the proviso that $Z^1$ and $Z^4$ are N.

12. A selenophene compound of formula (VI) as claimed in claim 7, wherein $Z^1$, $Z^2$, $Z^3$, and $Z^4$ are independently selected from the group consisting of N and C—$R^7$, with the proviso that either $Z^1$ and $Z^3$ or $Z^2$ and $Z^4$ are N.

13. A selenophene compound of formula (VI) as claimed in claim 7, wherein $Z^1$, $Z^2$, $Z^3$, and $Z^4$ are independently selected from the group consisting of N and C—$R^7$, with the proviso that:
$Z^1$ and $Z^2$ are N;
$Z^2$ and $Z^3$ are N; or
$Z^3$ and $Z^4$ are N.

14. A selenophene compound as claimed in claim 1, wherein ring A is a 5-membered heteroaromatic fused ring; said selenophene compound having formula (VII):

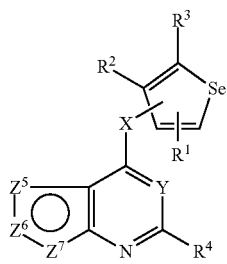

VII wherein:
$Z^5$, $Z^6$, and $Z^7$ are independently selected from the group consisting of N, NH, S, Se and C—$R^7$, wherein each $R^7$ is independently selected from the group consisting of hydrogen, halogen, hydroxy, formyl, carboxylic acid, amino, nitro, cyano, sulfonic acid, thiole, trihalomethyl, sulfonamide, $C_{1-6}$alkyl, $C_{1-6}$secondary-alkyl, $C_{1-6}$tertiary-alkyl, $C_{2-6}$alkenyl, $C_{2-6}$alkynyl, $C_{1-4}$alkylcarbonyl, $C_{1-4}$-alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$ alkyl, di($C_{1-6}$alkyl)amino$C_{1-6}$alkyl, $C_{1-6}$alkylsulfinyl, $C_{1-6}$alkylsulfonyl, phenyl, benzyl, a second five-membered heteroaromatic ring containing at least one heteroatom selected from the group consisting of sulfur, oxygen, nitrogen and selenium, and a group having the following formula:

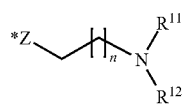

wherein n is 0 to 5;
* indicates a point of attachment to the benzene ring;
Z is selected from the group consisting of $CH_2$, O, S, or NH; and
$R^{11}$ and $R^{12}$ are independently selected from the group consisting of hydrogen, $C_{1-6}$alkyl, halo$C_{1-6}$alkyl, halo$C_{1-6}$alkoxy, and $C_{3-7}$cycloalkyl; or $R^{11}$ and $R^{12}$, together with the nitrogen atom to which they are attached, form a 5- to 7-membered heterocycloalkyl ring;
wherein phenyl and said second five-membered heteroaromatic ring are optionally substituted by halogen, hydroxy, formyl, carboxylic acid, amino, nitro, cyano, sulfonic acid, thiole, trihalomethyl, sulfonamide, $C_{1-6}$alkyl, $C_{2-6}$alkenyl, $C_{2-6}$alkynyl, $C_{1-4}$alkylcarbonyl, $C_{1-4}$alkoxycarbonyl, aminocarbonyl, $C_{1-6}$alkylaminocarbonyl, di($C_{1-6}$alkyl)aminocarbonyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{1-6}$alkylamino, di($C_{1-6}$alkyl)amino, amino$C_{1-6}$alkyl, amino$C_{1-6}$alkoxy, $C_{1-6}$alkylamino$C_{1-6}$alkyl, di($C_{1-6}$ alkyl)amino$C_{1-6}$alkyl, $C_{1-6}$alkylsulfinyl, or $C_{1-6}$alkylsulfonyl; and
wherein said second five-membered heteroaromatic ring contains no more than one oxygen or sulfur or selenium atom.

15. A selenophene compound of formula (VII) as claimed in claim 14, wherein $Z^5$, $Z^6$, and $Z^7$ are independently selected from the group consisting of S and C—$R^7$,
with the proviso that one of $Z^5$, $Z^6$, and $Z^7$ is S.

16. A selenophene compound of formula (VII) as claimed in claim 14, wherein $Z^5$, $Z^6$, and $Z^7$ are independently selected from the group consisting of O and C—$R^7$,
with the proviso that one of $Z^5$, $Z^6$, and $Z^7$ is O.

17. A selenophene compound of formula (VII) as claimed in claim 14, wherein $Z^5$, $Z^6$, and $Z^7$ are independently selected from the group consisting of NH and C—$R^7$,
with the proviso that one of $Z^5$, $Z^6$, and $Z^7$ is NH.

18. A selenophene compound of formula (VII) as claimed in claim 14, wherein $Z^5$, $Z^6$, and $Z^7$ are independently selected from the group consisting of Se and C—$R^7$,
with the proviso that one of $Z^5$, $Z^6$, and $Z^7$ is Se.

19. A selenophene compound of formula (VII) as claimed in claim 14, wherein $Z^5$ is oxygen or nitrogen, $Z^6$ is C—$R^7$, and $Z^7$ is oxygen or nitrogen;
wherein $Z^5$ and $Z^7$ are not both nitrogen or both oxygen.

20. A selenophene compound of formula (VII) as claimed in claim 14, wherein one of $Z^5$, $Z^6$, and $Z^7$ is O; one of $Z^5$, $Z^6$, and $Z^7$ is N; and one of $Z^5$, $Z^6$, and $Z^7$ is C—$R^7$,
with the proviso that the ring contains an N—O bond.

21. A selenophene compound of formula (VII) as claimed in claim 14, wherein $Z^5$ is N or NH, $Z^6$ is C—$R^7$, and $Z^7$ is N or NH;
wherein $Z^5$ and $Z^7$ are not both N or both NH.

22. A selenophene compound of formula (VII) as claimed in claim 14, wherein one of $Z^5$, $Z^6$, and $Z^7$ is N; one of $Z^5$, $Z^6$, and $Z^7$ is NH; and one of $Z^5$ and $Z^7$ is C—$R^7$,
with the proviso that the ring contains an N—NH bond.

23. A selenophene compound of formula (VII) as claimed in claim 14, wherein one of $Z^5$ and $Z^7$ is N; one of $Z^5$ and $Z^7$ is S; and $Z^6$ is C—$R^7$,
with the proviso that the ring contains both S and N.

24. A selenophene compound of formula (VII) as claimed in claim 14, wherein one of $Z^5$, $Z^6$, and $Z^7$ is S; one of $Z^5$, $Z^6$, and $Z^7$ is N; and one of $Z^5$ and $Z^7$ is C—$R^7$,
with the proviso that the ring contains an S—N bond.

25. A selenophene compound selected from the group consisting of:
3-(6,7-Dimethoxyquinazolin-4-ylamino)-5-tert-butylselenophene-2-carboxamide;
3-(6,7,8-Trimethoxyquinazolin-4-ylamino)-5-tert-butylselenophene-2-carboxamide;
3-(6-(3-Morpholinopropoxy)-7-methoxyquinazolin-4-ylamino)-5-tert-butylselenophene-2-carboxamide;
[5-(tert-Butyl)-2-nitroselenophen-3-yl][7-methoxy-6-(3-morpholinopropoxy)quinazolin-4-yl]amine;
3-(7-(3-Morpholinopropoxy)-6-methoxyquinazolin-4-ylamino)-5-tert-butylselenophene-2-carboxamide;
3-(6,7-Bis(2-methoxyethoxy)quinazolin-4-ylamino)-5-tert-butylselenophene-2-carboxamide;
3-(6-(3-Morpholinopropoxy)-7-methoxyquinazolin-4-ylamino)-5-phenyl-selenophene-2-carboxamide;

3-(6-Aminoquinazolin-4-ylamino)-5-tert-butylselenophene-2-carboxamide;
3-(6-(2-Chloroacetamido)quinazolin-4-ylamino)-5-tert-butylselenophene-2-carboxamide;
Methyl 4-(6-(3-morpholinopropoxy)-7-methoxyquinazolin-4-ylamino)-5-methyl-selenophene-2-carboxylate;
4-(6-(3-Morpholinopropoxy)-7-methoxyquinazolin-4-ylamino)-5-methylselenophene-2-carboxamide;
5-tert-Butyl-3-(pyridino[2,3-d]pyrimidin-4-ylamino)selenophene-2-carboxamide;
3-(5-Ethyl-6-methylthiopheno[2,3-d]pyrimidin-4-ylamino)-5-tert-butylselenophene-2-carboxamide;
3-(6-(Methylthio)thiopheno[3,2-d]pyrimidin-4-ylamino)-5-tert-butyl-selenophene-2-carboxamide;
3-(6-Phenylfuro[2,3-d]pyrimidin-4-ylamino)-5-tert-butylselenophene-2-carboxamide;
3-(6-tert-Butylfuro[2,3-d]pyrimidin-4-ylamino)-5-tert-butylselenophene-2-carboxamide;
Methyl 4-(5,6-dimethyl-7H-pyrrolo[2,3-d]pyrimidin-4-ylamino)-5-methylselenophene-2-carboxylate;
3-(6-tert-Butylselenopheno[3,2-d]pyrimidin-4-ylamino)-5-tert-butylselenophene-2-carboxamide;
3-(5-Ethyl-6-methylselenopheno[2,3-d]pyrimidin-4-ylamino)-5-tert-butylselenophene-2-carboxamide;
3-(2-(Methylthio)thiazolo[4,5-d]pyrimidin-7-ylamino)-5-tert-butylseleno-phene-2-carboxamide;
3-(N-(6,7-Dimethoxyquinazolin-4-yl)-N-methylamino)-5-tert-butylseleno-phene-2-carboxamide;
3-(N-(6-(3-Morpholinopropoxy)-7-methoxyquinazolin-4-yl)-N-methylamino)-5-tert-butylselenophene-2-carboxamide;
3-(N-(6-(3-Morpholinopropoxy)-7-methoxyquinazolin-4-yl)-N-(2-chloroethyl)amino)-5-tert-butylselenophene-2-carboxamide;
3-(6,7-Dimethoxy-2-methylquinazolin-4-ylamino)-5-tert-butylselenophene-2-carboxamide;
Methyl 4-(6,7-dimethoxy-2-methylquinazolin-4-ylamino)-5-methylselenophene-2-carboxylate;
3-(6-(3-Morpholinopropoxy)-7-methoxy-2-methylquinazolin-4-ylamino)-5-tert-butylselenophene-2-carboxamide;
(3-Ethynylphenyl)-5,6,7,8-tetrahydropyrimidino[5',6'-5,4]selenopheno[2,3-c]pyridin4-ylamine;
3-(2-(4-Chlorophenyl)-6,7-dimethoxyquinazolin-4-ylamino)-5-tert-butylselenophene-2-carboxamide; and
3-(6,7-Dimethoxyquinazolin-4-yloxy)-5-tert-butylselenophene-2-carboxamide.

26. A process for the preparation of a selenophene compound of formula (I) according to claim 1 or a salt thereof;

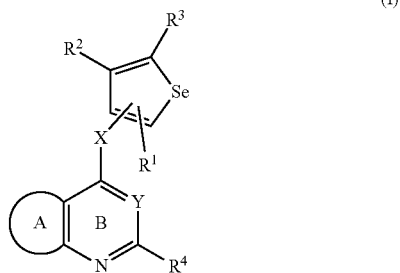
(I)

wherein said process comprises a step selected from the group consisting of:

[A] reacting a compound of formula II with a compound of formula III in the presence of a solvent and optionally in the presence of a base selected from the group consisting of organic and inorganic bases;

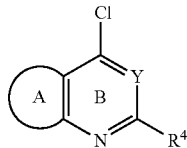
Formula II

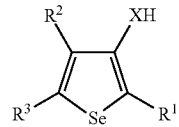
Formula III

[B] reacting a compound of formula II with a compound of formula IV in the presence of a solvent and optionally in the presence of a base selected from the group consisting of organic and inorganic bases;

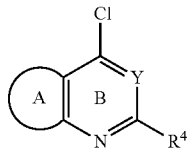
Formula II

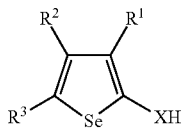
Formula IV

[C] reacting a compound of formula V with dimethylformamide-dimethylacetal or triethylorthoformate or trimethylorthoformate in the presence of a protic solvent; and further reacting with a compound of formula IIIa;

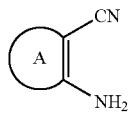
Formula V

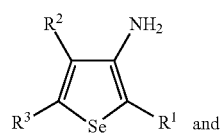
Formula IIIa and

[D] reacting a compound of formula V with dimethylformamide-dimethylacetal or triethylorthoformate or trimethylorthoformate in the presence of a protic solvent; and further reacting with a compound of formula IVa;

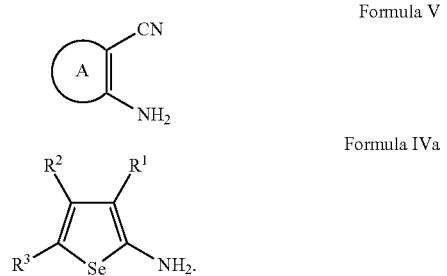

Formula V

Formula IVa

27. A process for the preparation of selenophene compound of formula (I) as claimed in claim 26, wherein the selenophene compound of formula (I) is prepared from a compound of formula II,
wherein Y in formula II is N or $CR^5$ and ring A in formula II is selected from the group consisting of benzene, pyridine, pyrazine, pyrimidine, pyridazine, thiophene, furan, pyrrole, selenophene, oxazole, isoxazole, imidazole, pyrazole, thiazole, and isothiazole.

28. A process for the preparation of selenophene compound of formula (I) as claimed in claim 26, wherein the selenophene compound of formula (I) is prepared from a compound of formula V,
wherein ring A in formula V is selected from the group consisting of benzene, pyridine, pyrazine, pyrimidine, pyridazine, thiophene, furan, pyrrole, selenophene, oxazole, isoxazole, imidazole, pyrazole, thiazole, and isothiazole.

29. A process for the preparation of selenophene compound of formula (I) as claimed in claim 26,
wherein the selenophene compound of formula (I) is prepared from a compound of formula II, and
wherein X is NH or O.

30. A pharmaceutical composition comprising:
at least one selenophene compound of formula (I) according to claim 1, a pharmaceutically acceptable salt thereof, a solvate or hydrate thereof, or a stereoisomer thereof; and
at least one additive selected from the group consisting of a pharmaceutically acceptable excipient, a pharmaceutically acceptable diluent, and a pharmaceutically acceptable carrier.

31. The pharmaceutical composition as claimed in claim 30, further comprising at least one anti-tumor agent selected from the group consisting of an Alkylating agent, an Anti-metabolite, a Hormonal therapy agent, a Cytotoxic topoisomerase inhibiting agent, a Anti-angiogenic compound, an Antibody, a VEGF inhibitor, an EGFR (HER1) inhibitor, a HER2 inhibitor, a CDK inhibitor, a Proteasome inhibitor, a Serine/threonine kinase (Raf) inhibitor, a Tyrosine kinase inhibitor, an Androgen receptor antagonist and an Aromatase inhibitor.

32. A pharmaceutical composition as claimed in claim 30, wherein said additive is selected from the group consisting of glucose, fructose, sucrose, maltose, yellow dextrin, white dextrin, aerosol, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors, preservatives, distilled water, saline, aqueous glucose solution, alcohol (e.g. ethanol), propylene glycol, polyethylene glycol, animal and vegetable oils, white soft paraffin, paraffin and wax.

33. A pharmaceutical composition as claimed in claim 31, wherein:
the Alkylating agent is selected from the group consisting of nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, mitolactol, cisplatin, carboplatin, eptaplatin, lobaplatin, nedaplatin, oxaliplatin, and satraplatin;
the Anti-metabolite is selected from the group consisting of methotrexate, 6-mercaptopurineriboside, mercaptopurine, 5-fluorouracil, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosf[iota]te, disodium premetrexed, pentostatin, pelitrexol, raltitrexed, triapine, trimetrexate, vidarabine, vincristine, and vinorelbine;
the Hormonal therapy agent is selected from the group consisting of exemestane, Lupron, anastrozole, doxercalciferol, fadrozole, formestane, abiraterone acetate, finasteride, epristeride, tamoxifen citrate, fulvestrant, Trelstar, toremifene, raloxifene, lasofoxifene, letrozole, sagopilone, ixabepilone, epothilone B, vinblastine, vinflunine, docetaxel, and paclitaxel;
the Cytotoxic topoisomerase inhibiting agent is selected from the group consisting of aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide;
the Anti-angiogenic compound is selected from the group consisting of acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin;
the Antibody is selected from the group consisting of trastuzumab, cetuximab, bevacizumab, rituximab, ticilimumab, ipilimumab, lumiliximab, catumaxomab, atacicept, oregovomab, and alemtuzumab;
the VEGF inhibitor is selected from the group consisting of sorafenib, DAST, bevacizumab, sunitinib, recentin, axitinib, aflibercept, telatinib, brivanib alaninate, vatalanib, pazopanib, and ranibizumab;
the EGFR (HER1) inhibitor is selected from the group consisting of cetuximab, panitumumab, vectibix, gefitinib, erlotinib, and Zactima;
the HER2 inhibitor is selected from the group consisting of lapatinib, tratuzumab, and pertuzumab;
the CDK inhibitor is selected from the group consisting of roscovitine and flavopiridol;
the Proteasome inhibitor is selected from the group consisting of bortezomib and carfilzomib; Serine/threonine kinase (Raf) inhibitor is sorafenib;
the Tyrosine kinase inhibitor is selected from the group consisting of dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab and pertuzumab;

the Androgen receptor antagonist is selected from the group consisting of nandrolone decanoate, fluoxymesterone, Android, Prostaid, andromustine, bicalutamide, flutamide, apocyproterone, apoflutamide, chlormadinone acetate, Androcur, Tabi, cyproterone acetate, and nilutamide; and the Aromatase inhibitor is selected from the group consisting of anastrozole, letrozole, testolactone, exemestane, aminoglutethimide, and formestane.

34. A method of treating or inhibiting, or controlling cell proliferative disorder in a warm blooded animal in need thereof, wherein said method comprises administering to the said warm blooded animal a therapeutically effective amount of at least one selenophene compound of formula (I) as claimed in claim 1.

35. A method of treating or inhibiting, or controlling cell proliferative disorder in a warm blooded animal in need thereof, wherein said method comprises administering to the said warm blooded animal a therapeutically effective amount of at least one composition as claimed in claim 30.

36. A method of treating or inhibiting, or controlling cell proliferative disorder in a warm blooded animal in need thereof, wherein said method comprises administering to the said warm blooded animal a therapeutically effective amount of at least one composition as claimed in claim 31.

37. A method according to claim 34, wherein said cell proliferative disorder is selected from the group consisting of psoriasis, keloids, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia (BPH), and solid tumors.

38. A method of treating or controlling tumor or cancer growth by blocking angiogenesis or by inhibiting vascular capillary formation with the administration of at least one selenophene compound of formula (I) as claimed in claim 1, a pharmaceutically acceptable salt thereof, a solvate or hydrate thereof, or a stereoisomer thereof.

39. A method of treating or inhibiting, or controlling cell proliferative disorder as claimed in claim 34, wherein said administering comprises administering by a route selected from the group consisting of intraperitoneal (IP), intravenous (IV), oral (PO), intramuscular (IM), intracutaneous (IC), intradermal (ID), intrauterine, intratumoral and intrarectal.

* * * * *